US008216783B2

(12) United States Patent
Khan et al.

(10) Patent No.: US 8,216,783 B2
(45) Date of Patent: Jul. 10, 2012

(54) OVER-EXPRESSION AND MUTATION OF A TYROSINE KINASE RECEPTOR FGFR4 IN TUMORS

(75) Inventors: Javed Khan, Derwood, MD (US); James G. Taylor, VI, Fairfax, VA (US); Tai Cheuk, Germantown, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 424 days.

(21) Appl. No.: 12/423,750

(22) Filed: Apr. 14, 2009

(65) Prior Publication Data

US 2009/0258369 A1    Oct. 15, 2009

Related U.S. Application Data

(60) Provisional application No. 61/044,875, filed on Apr. 14, 2008.

(51) Int. Cl.
  *C12Q 1/68* (2006.01)
  *C12P 19/34* (2006.01)
  *G01N 33/53* (2006.01)

(52) U.S. Cl. .......................... 435/6.1; 435/91.2; 435/7.1

(58) Field of Classification Search ........................ None
See application file for complete search history.

(56) References Cited

U.S. PATENT DOCUMENTS

| 5,866,323 | A | 2/1999 | Markowitz et al. |
| 7,135,311 | B1 | 11/2006 | David et al. |
| 2004/0009154 | A1 | 1/2004 | Khan et al. |
| 2004/0067885 | A1 | 4/2004 | Ullrich et al. |
| 2006/0084142 | A1 | 4/2006 | Heinrich et al. |
| 2008/0113986 | A1 | 5/2008 | Ren et al. |

FOREIGN PATENT DOCUMENTS

| WO | WO 2008/052796 | 5/2008 |
| WO | WO 2008/052798 | 5/2008 |

OTHER PUBLICATIONS

Bange, et al., "Cancer Progression and Tumor Cell Motility Are Associated with the FGFR4 Arg[388] Allele," *Cancer Research*, vol. 62, pp. 840-847, 2002.
Baselga, "Targeting Tyrosine Kinases in Cancer: The Second Wave," *Science*, vol. 312, pp. 1175-1178, 2006.
Chen, et al., "A Molecular Brake in the Kinase Hinge Region Regulates the Activity of Receptor Tyrosine Kinases," *Molecular Cell*, vol. 27, pp. 717-730, 2007.
Corless, et al., "PDGFRA Mutations in Gastrointestinal Stromal Tumors: Frequency, Spectrum and In Vitro Sensitivity to Imatinib," *Journal of Clinical Oncology*, vol. 23, No. 23, pp. 5357-5364, 2005.
Ezzat, et al., "Targeted expression of a human pituitary tumor-derived isoform of FGF receptor-4 recapitulates pituitary tumorigenesis," *Journal of Clinical Investigation*, vol. 109, No. 1, pp. 69-78, 2002.
Ezzat, et al., "Targeting N-Cadherin through Fibroblast Growth Factor Receptor-4: Distinct Pathogenetic and Therapeutic Implications," *Molecular Endocrinology*, vol. 20, No. 11, pp. 2965-2975, 2006.
Gowardhan, et al., "Evaluation of the fibroblast growth factor system as a potential target for therapy in human prostate cancer," *British Journal of Cancer*, vol. 92, No. 2, pp. 320-327, 2005.
Greenman, et al., "Patterns of somatic mutation in human cancer genomes," *Nature*, vol. 446, pp. 153-158, 2007.
Greenman, et al., "Patterns of somatic mutation in human cancer genomes," *Nature*, vol. 446, pp. 153-158, 2007 Supplemental Information, http://www.nature.com/nature/journal/v446/n7132/suppinfo/nature05610.html.
Jang, et al., "Mutations in *Fibroblast Growth Factor Receptor 2* and *Fibroblast Growth Factor Receptor 3* Genes Associated with Human Gastric and Colorectal Cancers," *Cancer Research*, vol. 61, pp. 3541-3543, 2001.
Khan, et al., "Classification and diagnostic prediction of cancers using gene expression profiling and artificial neural networks," *Nature Medicine*, vol. 7, No. 6, pp. 673-679, 2001.
Khanna and Hunter, "Modeling metastasis in vivo," *Carcinogenesis*, vol. 26, No. 3, pp. 513-523, 2005.
Mohammadi, et al., "Crystal structure of an angiogenesis inhibitor bound to the FGF receptor tyrosine kinase domain," *EMBO Journal*, vol. 17, No. 29, pp. 5896-5904, 1998.
Morimoto, et al., "Single Nucleotide Polymorphism in Fibroblast Growth Factor Receptor 4 at Codon 388 is Associated with Prognosis in High-Grade Soft Tissue Sarcoma," *Cancer*, vol. 98, No. 10, pp. 2245-2250, 2003.
Pollock, et al., "Frequent activating FGFR2 mutations in endometrial carcinomas parallel germline mutations associated with craniosynostosis and skeletal dysplasia syndromes," *Oncogene*, vol. 26, pp. 7158-7162, 2007.
Rand, et al., "Sequence survey of receptor tyrosine kinases reveals mutations in glioblastomas," *Proc. Natl. Acad. Sci. USA*, vol. 102, No. 40, pp. 14344-14349, 2005.
Rosty, et al., "Clinical and biological characteristics of cervical neoplasias with FGFR3 mutation," *Molecular Cancer*, vol. 4:15, 2005.
Sahadevan, et al., "Selective over-expression of fibroblast growth factor receptors 1 and 4 in clinical prostate cancer," *Journal of Pathology*, vol. 213, pp. 82-90, 2007.
Shah, et al., "*FGFR4* overexpression in pancreatic cancer is mediated by an intronic enhancer activated by HNF1α," *Oncogene*, vol. 21, pp. 8251-8261, 2002.
Spinola, et al., "Functional FGFR4 Gly388Arg Polymorphism Predicts Prognosis in Lung Adenocarcinoma Patients," *Journal of Clinical Oncology*, vol. 23, No. 29, pp. 7307-7311, 2005.
Takeda, et al., "AZD2171 Shows Potent Antitumor Activity Against Gastric Cancer Over-Expressing Fibroblast Growth Factor Receptor 2/Keratinocyte Growth Factor Receptor," *Clinical Cancer Research*, vol. 13, No. 10, pp. 3051-3057, 2007.

(Continued)

*Primary Examiner* — Stephen Kapushoc
(74) *Attorney, Agent, or Firm* — Klarquist Sparkman, LLP

(57) ABSTRACT

This disclosure provides tyrosine kinase protein and nucleic acid variants, particularly FGFR4 variants, which are linked to increased risk of tumor metastasis. The disclosure further provides methods of diagnosis and prognosis, and development of new therapeutic agents using these molecules and fragments thereof, and kits for employing these methods and compositions.

18 Claims, 28 Drawing Sheets

OTHER PUBLICATIONS

Taylor, et al., "Identification of activating mutations of the fibroblast growth factor receptor 4 in rhabdomyosarcoma," 2008 AACR Annual Meeting, Abstract No. 3748, 2008.

Thussbas, et al., "FGFR4 Arg388 Allele is Associated With Resistance to Adjuvant Therapy in Primary Breast Cancer," *Journal of Clinical Oncology*, vol. 24, No. 23, pp. 3747-3755, 2006.

Torkamani and Schork, "Prediction of Cancer Driver Mutations in Protein Kinases," *Cancer Research*, vol. 68, No. 6, pp. 1675-1682, 2008.

Torkamani and Schork, "Prediction of Cancer Driver Mutations in Protein Kinases," *Cancer Research*, vol. 68, No. 6, 2008, Supplemental Information, http://cancerres.aacrjournals.org/cgi/content/full/68/6/1675/DC1.

Wang, et al., "The Fibroblast Growth Factor Receptor-4 Arg$^{388}$ Allele is Associated with Prostate Cancer Initiation and Progression," *Clinical Cancer Research*, vol. 10, pp. 6169-6178, 2004.

Xin, et al., "CHIR-258 is Efficacious in a Newly Developed Fibroblast Growth Factor Receptor 3—Expressing Orthotopic Multiple Myeloma Model in Mice," *Clinical Cancer Research*, vol. 12, No. 16, pp. 4908-4915, 2006.

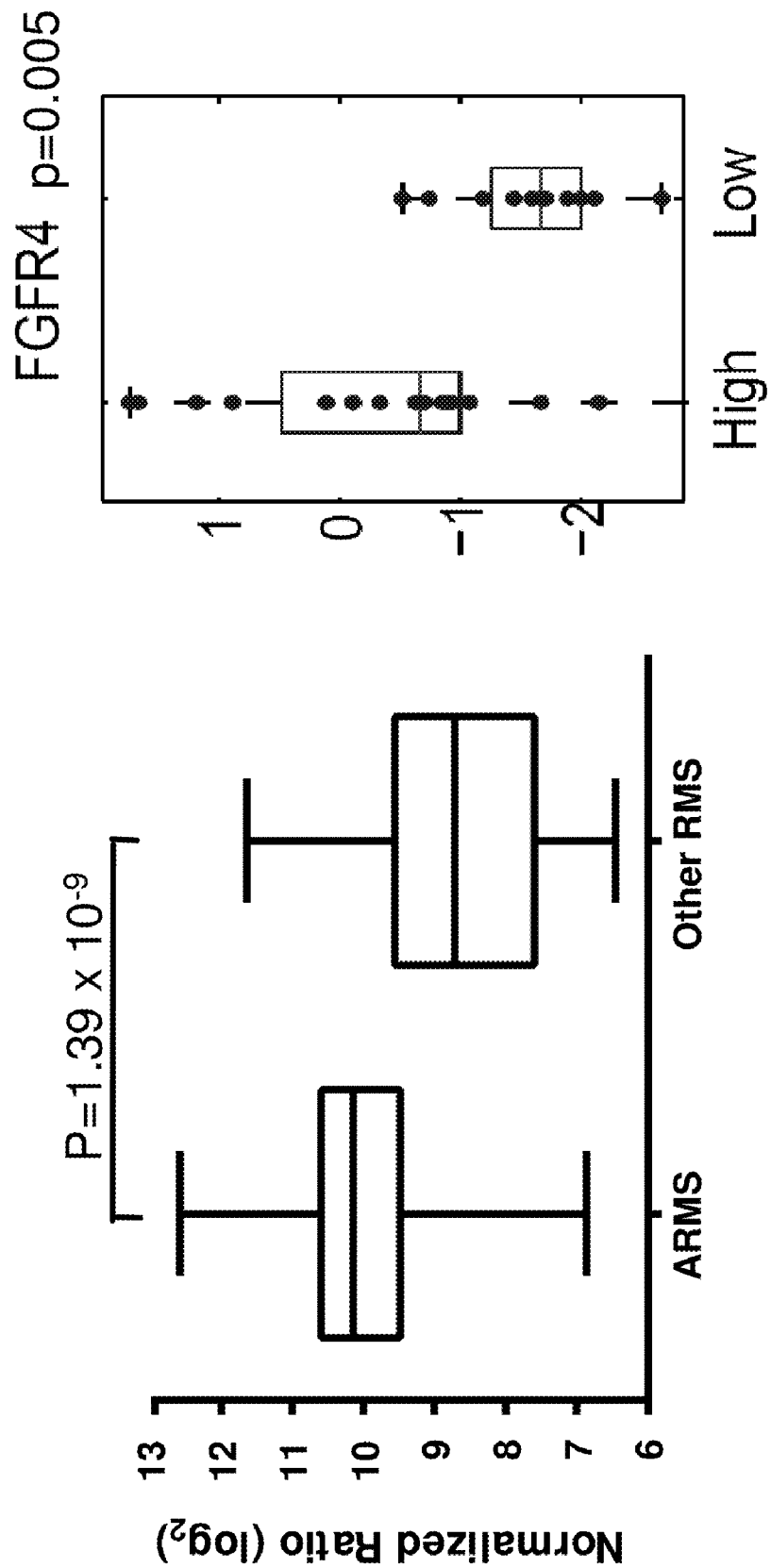

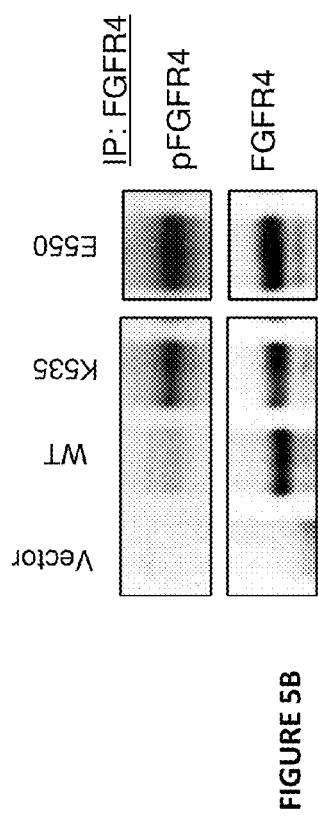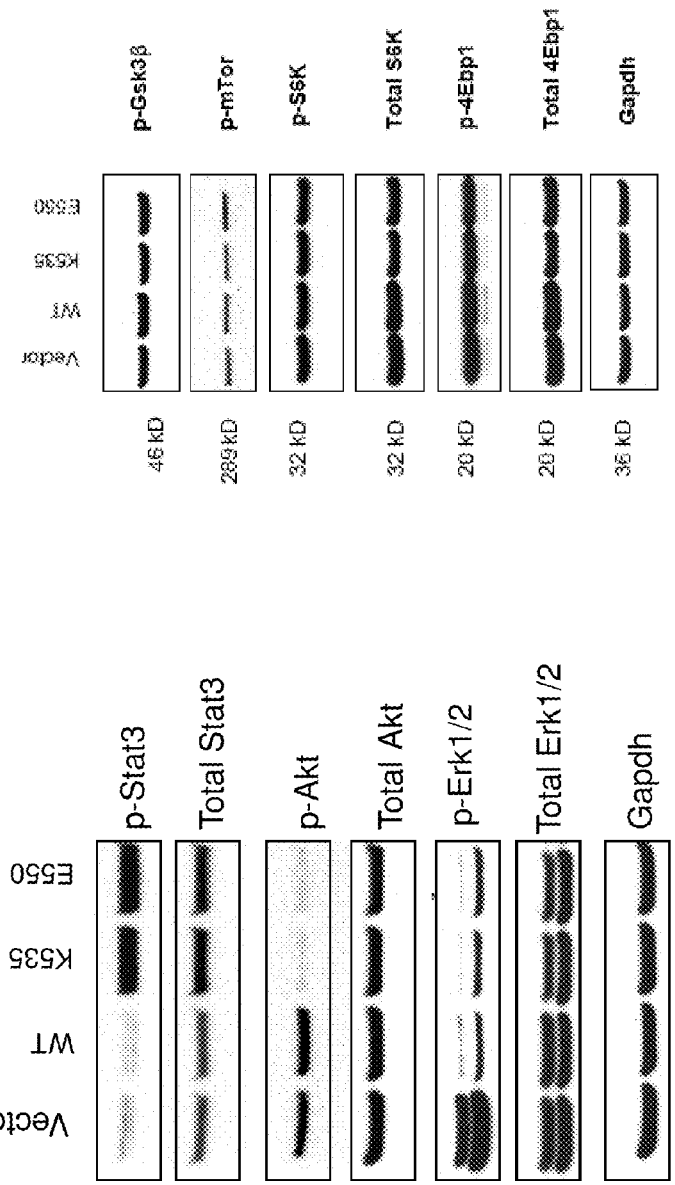

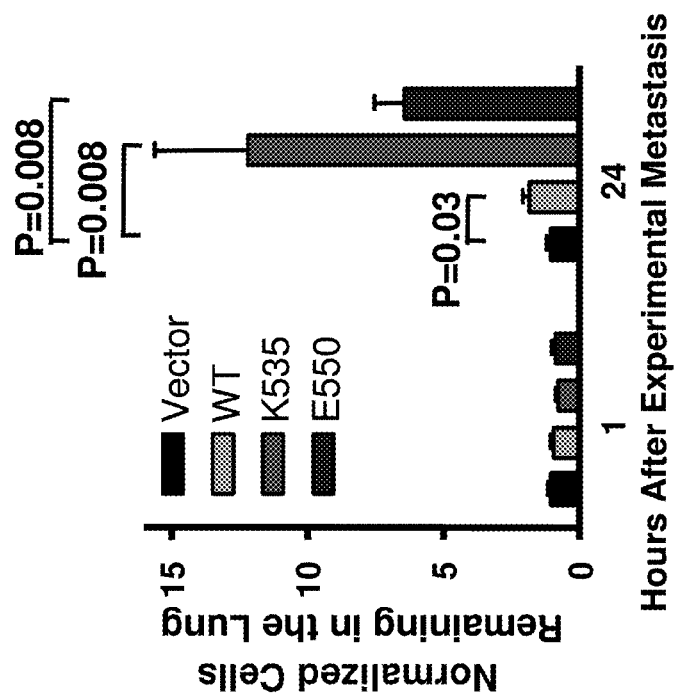
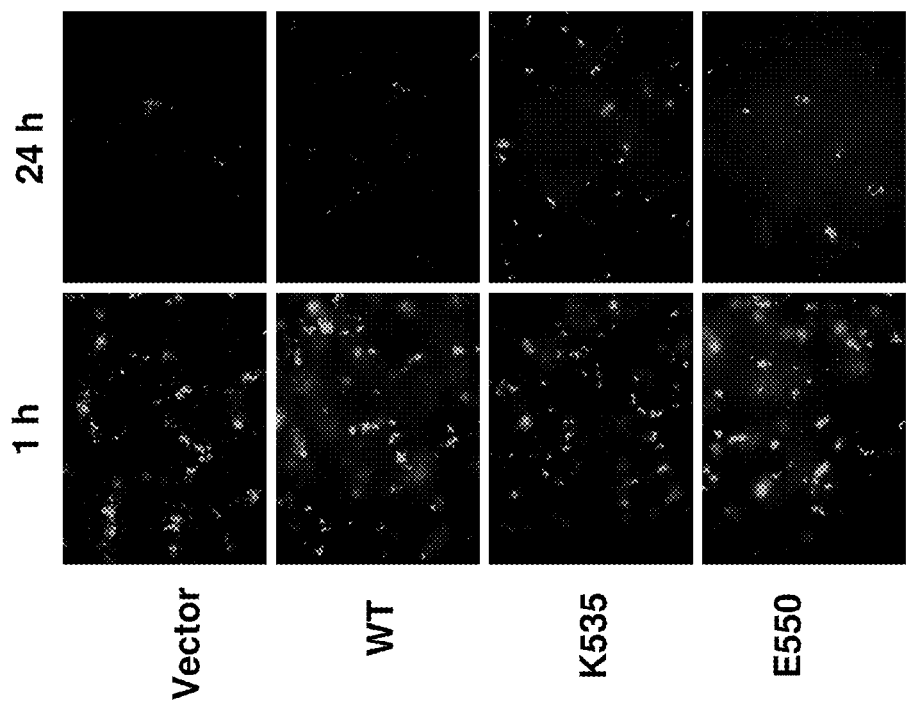

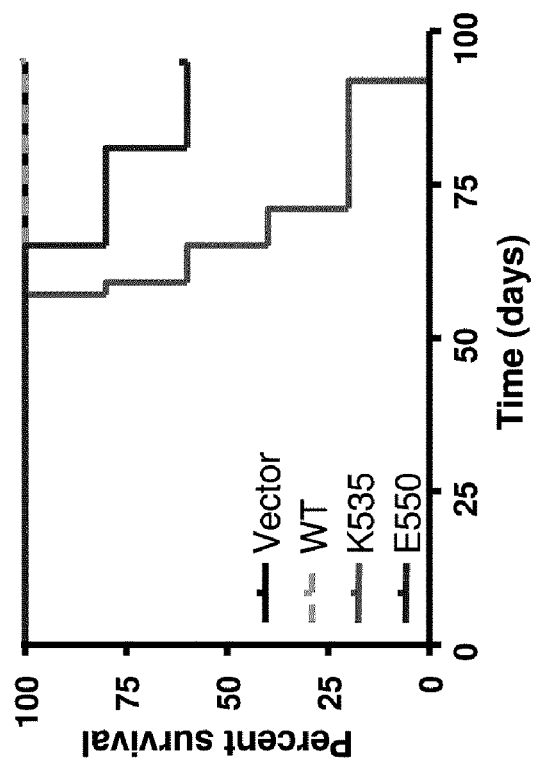
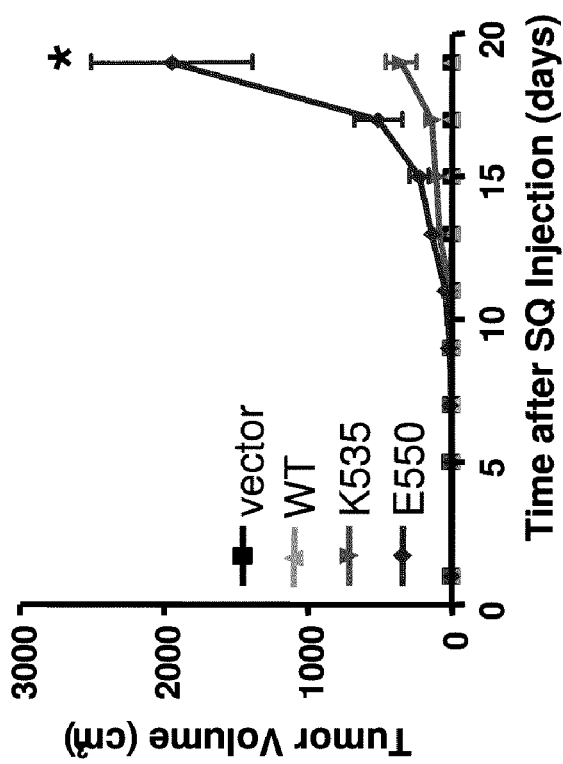
FIGURE 8A
FIGURE 8B

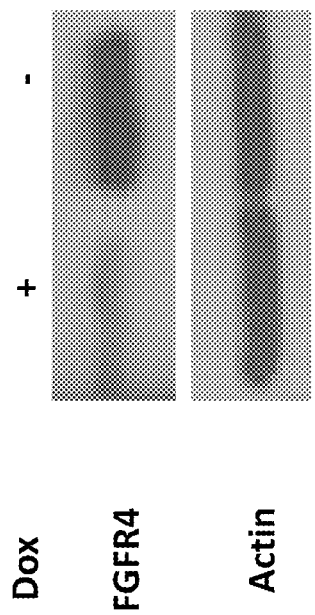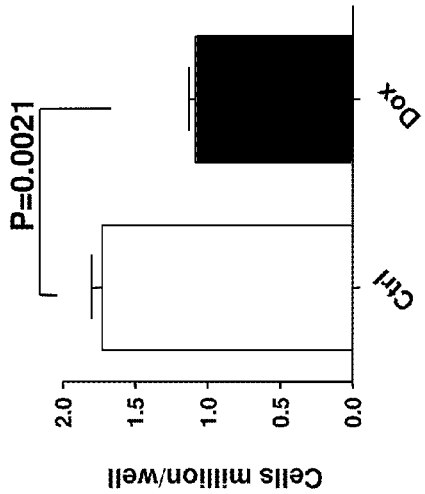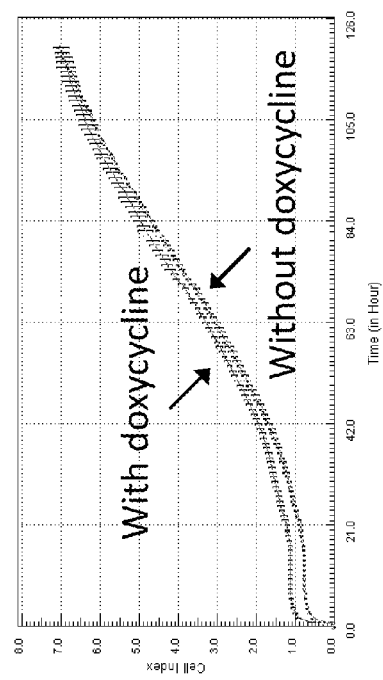
FIGURE 13A
FIGURE 13B
FIGURE 13C

OVER-EXPRESSION AND MUTATION OF A TYROSINE KINASE RECEPTOR FGFR4 IN TUMORS

CROSS REFERENCE TO RELATED APPLICATION

This application claims the benefit of U.S. Provisional Application No. 61/044,875, filed Apr. 14, 2008, which is incorporated herein in its entirety.

FIELD

This disclosure relates to tyrosine kinases, particularly receptor tyrosine kinases with one or more variants. Further, it relates to methods of using these molecules in screens and analyses, including diagnoses, prognoses, and systems for identification and/or selection of pharmaceutical compounds.

BACKGROUND

Rhabdomyosarcoma (RMS) is a rare pediatric soft tissue sarcoma grouped into alveolar (ARMS), embryonal (ERMS), and other histological subtypes. ARMS is associated with older patients and chromosomal translocations encoding a fusion gene involving FKHR on chromosome 13 and members of the PAX gene family. Embryonal RMS is characterized by a younger age at diagnosis, loss of heterozygosity and altered patterns of genomic imprinting. An important determinant of long term survival in all subtypes is the absence of metastatic disease, although a third of patients either present or relapse with metastases, succumbing to this fatal stage of malignancy. A major deficit in the present understanding of cancer pathophysiology is the identity of the genetic events controlling development of tumor metastases.

Fibroblast growth factor receptors (FGFRs) are of great interest in cancer biology as they regulate essential processes including cellular survival, motility, development, and angiogenesis. In humans, FGFRs have a highly conserved amino acid sequence across family members including FGFR1, FGFR2, FGFR3, and FGFR4. These cell surface receptors consist of extracellular immunoglobulin-like domains, a transmembrane domain, and an intracellular tyrosine kinase (TK) domain. FGFR4 has been shown to be overexpressed in a variety of cancers, including rhabdomyosarcoma, prostate cancer, breast cancer, and lung cancer (Khan et al., *Nat. Med.* 7:673-679, 2001; Sahadevan et al., *J. Pathol.* 213:82-90, 2007; Bange et al., *Cancer Res.* 62:840-847, 2002).

Metastasis, the spread of a tumor from its primary site to other parts of the body, continues to be the most significant problem in the field of cancer. Patients who present with metastatic disease or those who develop metastases after successful management of the primary tumor carry a universally poor prognosis.

SUMMARY

There is a need to identify genes that contribute to tumor metastasis and to develop compounds that inhibit metastasis. Disclosed herein are methods for identifying a subject as a candidate for treatment with an inhibitor of fibroblast growth factor receptor 4 (FGFR4) to induce tumor cell death, inhibit tumor growth, or decrease risk of metastasis of a tumor. In certain embodiments, the method includes determining the presence of at least one variant in a FGFR4 gene in a sample from the subject. In additional embodiments, the method includes determining whether a sample from the subject has altered expression of a FGFR4 molecule including at least one variant in a FGFR4 gene, compared to a control sample. In particular examples, the sample is a tumor sample (such as a rhabdomyosarcoma).

In particular examples, the variant is an amino acid substitution at amino acid position(s) 10, 56, 72, 122, 136, 175, 234, 535, 550, 554, or 576 of SEQ ID NO: 2, or a combination thereof. In some examples the variant is in that portion of the FGFR4 gene that encodes the tyrosine kinase (TK) domain of FGFR4. In particular examples, the variant includes a variant at amino acid position 535, 550, 554, and/or 576 of the FGFR4 protein.

Also disclosed are methods for decreasing risk of tumor metastasis in a subject. The method includes determining the presence of at least one FGFR4 variant in a sample from a subject and administering a therapeutically effective amount of an inhibitor of FGFR4 to the subject having the variant.

Methods for identifying a compound that induces tumor cell death, inhibits tumor growth, or inhibits tumor metastasis are disclosed herein. In one embodiment, the method includes contacting a test compound with a FGFR4 polypeptide comprising at least one variant which increases risk of tumor metastasis. The method further includes determining whether the test compound inhibits an activity of the FGFR4 variant (such as tyrosine kinase activity), wherein inhibition of the FGFR4 activity in the presence of the test compound as compared to in the absence of the test compound identifies the test compound as a compound that induces tumor cell death, inhibits tumor growth, and/or inhibits tumor metastasis.

Kits are also provided for carrying out the methods provided herein. In some examples, the kits include primers or probes to detect one or more variants of a FGFR4 gene.

The foregoing and other objects, features, and advantages of the invention will become more apparent from the following detailed description, which proceeds with reference to the accompanying figures.

BRIEF DESCRIPTION OF THE DRAWINGS

FIG. 1E shows FGFR4 expression in alveolar RMS compared to all other histologic RMS subtypes.

FIG. 1F shows FGFR4 gene expression in high or low metastatic RMS tumor cell lines derived from Ink4a/Arf deficient mice. Murine RMS cell lines with high metastatic potential have significantly higher FGFR4 mRNA levels than non-metastatic RMS cell lines (P=0.005).

FIG. 5A shows Western blots for FGFR4 and phospho-FGFR4 in RMS772 cells expressing vector only, wild type FGFR4 (WT), FGFR4 N535K (K535), or V550E (E550) mutants.

FIG. 5B shows Western blots for total and phosphorylated forms of Stat3, Akt, and Erk1/2 in RMS772 cells expressing human FGFR4 wild type or mutant proteins. Gapdh is a loading control.

FIG. 5C shows Western blots for phospho-Gsk3β, phospho-mTOR, and total and phosphorylated forms of S6K and 4Ebp1 in RMS772 cells expressing human FGFR4 wild type or mutant proteins. Gapdh is a loading control.

FIG. 7D is a series of photographs from intravital videomicroscopy (IVVM) in nude mice following tail vein injection of fluorescently labeled RMS772 cells expressing vector only, wild type FGFR4 (WT), FGFR4 N535K (K535), or FGFR4 V550E (E550) showing cells present in the lungs at 1 hour and 24 hours following injection.

FIG. 7E shows cell counts of fluorescently labeled RMS772 cells expressing vector only, wild type FGFR4 (WT), FGFR4 N535K (K535), or FGFR4 V550E (E550) present in the lungs at 1 hour, 4 hours, and 24 hours following intravenous injection of cells in nude mice (normalized to vector control).

FIG. 8A shows tumor volume in nude mice following subcutaneous injection of NIH3T3 cells expressing vector only, wild type FGFR4 (WT), FGFR4 N535K (K535), or FGFR4 V550E (E550).

FIG. 8B is a Kaplan-Meier plot showing survival in nude mice intravenously injected with NIH3T3 cells expressing vector only, wild type FGFR4 (WT), FGFR4 N535K (K535), or FGFR4 V550E (E550). N=5 mice per group.

FIG. 13A is a Western blot showing FGFR4 expression in RH30 TRB H11.5 cells treated with (+) or without (−) 25 nM doxycycline (dox) for 48 hours.

FIG. 13B is a plot of RH30 TRB H11.5 cell growth with or without 25 nM dox for 120 hours.

FIG. 13C is a plot of RH30TRB H11.5 cell number 13 days after treatment with or without 25 nM dox.

SEQUENCE LISTING

Figure 1B:
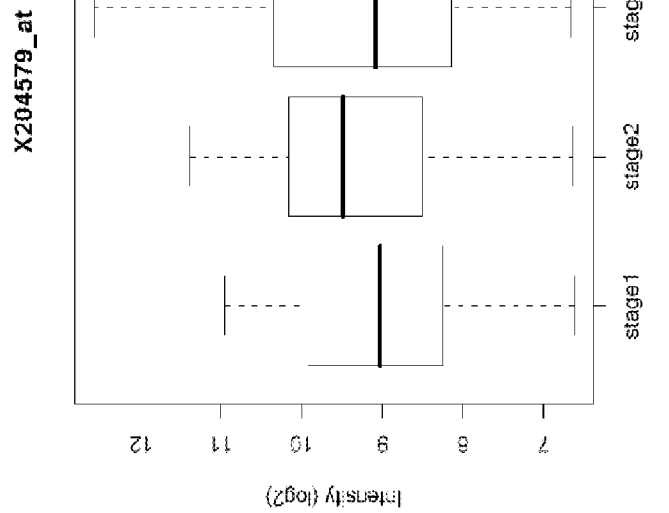
FIG. 1B shows expression of FGFR4 by tumor stage in primary pretreatment RMS tumors.

Any nucleic acid and amino acid sequences listed herein or in the accompanying sequence listing are shown using standard letter abbreviations for nucleotide bases, and three letter code for amino acids, as defined in 37 C.F.R. 1.822. In at least some cases, only one strand of each nucleic acid sequence is shown, but the complementary strand is understood as included by any reference to the displayed strand.

SEQ ID NOs: 1 and 2 show the nucleic acid and amino acid sequences, respectively, of an exemplary human FGFR4.

SEQ ID NO: 3 and 4 show forward and reverse primers, respectively, used to amplify FGFR4 exon 2.

SEQ ID NO: 5 and 6 show forward and reverse primers, respectively, used to amplify FGFR4 exon 3.

SEQ ID NO: 7 and 8 show forward and reverse primers, respectively, used to amplify FGFR4 exon 4.

SEQ ID NO: 9 and 10 show forward and reverse primers, respectively, used to amplify FGFR4 exon 5.

SEQ ID NO: 11 and 12 show forward and reverse primers, respectively, used to amplify FGFR4 exon 6.

SEQ ID NO: 13 and 14 show forward and reverse primers, respectively, used to amplify FGFR4 exon 7.

SEQ ID NO: 15 and 16 show forward and reverse primers, respectively, used to amplify FGFR4 exon 8.

SEQ ID NO: 17 and 18 show forward and reverse primers, respectively, used to amplify and sequence FGFR4 exons 9 and 10.

SEQ ID NO: 19 and 20 show forward and reverse primers, respectively, used to amplify FGFR4 exon 11.

SEQ ID NO: 21 and 22 show forward and reverse primers, respectively, used to amplify FGFR4 exon 12.

SEQ ID NO: 23 and 24 show forward and reverse primers, respectively, used to amplify FGFR4 exon 13.

SEQ ID NO: 25 and 26 show forward and reverse primers, respectively, used to amplify FGFR4 exon 14.

SEQ ID NO: 27 and 28 show forward and reverse primers, respectively, used to amplify FGFR4 exon 15.

SEQ ID NO: 29 and 30 show forward and reverse primers, respectively, used to amplify FGFR4 exon 16.

SEQ ID NO: 31 and 32 show forward and reverse primers, respectively, used to amplify FGFR4 exon 17.

SEQ ID NO: 33 and 34 show forward and reverse primers, respectively, used to amplify FGFR4 exon 18.

SEQ ID NO: 35 and 36 show forward and reverse M13 primers, respectively, used to sequence FGFR4 exons.

SEQ ID NO: 37 shows a 3′ FOXO1 primer for RT-PCR.

SEQ ID NO: 38 and 39 show forward and reverse primers, respectively, used for real-time PCR copy number determination of FGFR4 exons 9 and 10.

SEQ ID NO: 40 shows a probe used for real-time PCR copy number determination of FGFR4 exons 9 and 10.

SEQ ID NO: 41 and 42 show forward and reverse primers, respectively, used for real-time PCR copy number determination of FGFR4 exons 3 and 4.

SEQ ID NO: 43 shows a probe used for real-time PCR copy number determination of FGFR4 exons 3 and 4.

SEQ ID NO: 44 shows a FGFR4 shRNA.

SEQ ID NO: 45 shows amino acids 524-559 of a FGFR4 protein.

SEQ ID NO: 46 shows amino acids 535-570 of a FGFR1 protein.

SEQ ID NO: 47 shows amino acids 538-573 of a FGFR2 protein.

SEQ ID NO: 48 shows amino acids 529-5564 of a FGFR3 protein.

SEQ ID NO: 49 shows amino acids 778-813 of a Ret protein.

DETAILED DESCRIPTION

I. Abbreviations

ARMS: alveolar RMS
Dox: doxycycline
ERMS: embryonal histological RMS
FGFR: fibroblast growth factor receptor
FGFR4: fibroblast growth factor receptor 4
IVVM: intravital videomicroscopy
RMS: rhabdomyosarcoma
TK: tyrosine kinase domain
TKI: tyrosine kinase inhibitor

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), Molecular *Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Control: A "control" refers to a sample or standard used for comparison with an experimental sample. In some embodiments, the control is a sample obtained from a healthy subject or a non-tumor tissue sample obtained from a patient diagnosed with cancer. In other embodiments, a control sample is a sample from a tumor that does not include a variant FGFR4 molecule. In some embodiments, the control is a historical control or standard reference value or range of values (such as a previously tested control sample, such as a group of cancer patients with a particular tumor type, or group of samples that represent baseline or normal values, such as the level of FGFR4 in non-tumor tissue).

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine (A), guanine (G), cytosine (C), and thymine (T) bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. For instance, it is appropriate to generate probes or primers from the reverse complement sequence of the disclosed nucleic acid molecules.

Fibroblast growth factor receptor (FGFR): A family of tyrosine kinase receptors activated by fibroblast growth factors (FGF), comprising extracellular immunoglobulin-like domains, a transmembrane domain, and an intracellular tyrosine kinase domain. The family includes at least four members: FGFR1, FGFR2, FGFR3, and FGFR4. Sequences for FGFRs are publicly available and known to one of skill in the art. In particular examples, the FGFR is FGFR4, or variants thereof.

FGFR4 sequences are publicly available. For example, GenBank Accession numbers NC_000005.8 (176446527 . . . 176457733) (incorporated herein by reference, version of Mar. 3, 2008) and NC_000079.5 disclose human and mouse FGFR4 gene sequences, respectively. GenBank Accession numbers NM_213647 (SEQ ID NO: 1) and NP_998812 (SEQ ID NO: 2) disclose exemplary human FGFR4 cDNA and protein sequences, respectively and GenBank Accession numbers NM_008011.2 and NP_032037.2 disclose exemplary mouse FGFR4 cDNA and protein sequences, respectively.

One skilled in the art will appreciate that FGFR4 nucleic acid and protein molecules can vary from those publicly available, such as FGFR4 sequences having one or more substitutions, deletions, insertions, or combinations thereof, while still retaining FGFR4 biological activity, such as tyrosine kinase activity. In addition, FGFR4 molecules include fragments that retain the desired FGFR4 biological activity. In further examples, FGFR4 sequences having one or more substitutions, deletions, insertions, or combinations thereof, may have altered activity (such as increased activity, decreased activity, or loss of activity).

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between to distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ concentration) of the hybridization buffer will determine the stringency of hybridization, though waste times also influence stringency. Calculations regarding hybridization conditions required for attaining particular degrees of stringency are discussed by Sambrook et al. (ed.), *Molecular Cloning: A Laboratory Manual,* 2nd ed., vol. 1-3, Cold Spring Harbor Laboratory Press, Cold Spring Harbor, N.Y., 1989, chapters 9 and 11, herein incorporated by reference.

For present purposes, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize.

In vitro amplification: Techniques that increase the number of copies of a nucleic acid molecule in a sample or specimen. An example of in vitro amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid.

The product of in vitro amplification may be characterized by electrophoresis, restriction endonuclease cleavage patterns, oligonucleotide hybridization or ligation, and/or nucleic acid sequencing, using standard techniques.

Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Metastasis: The spread of a tumor from one part of the body to another. Tumors formed from cells that have spread are called "secondary tumors" and contain cells that are like those in the original (primary) tumor. Metastasis is caused by at least a single tumor cell that is derived from an original tumor and that circulates or migrates to a different site from the original tumor. Metastasis requires the establishment of a new blood supply at the new tumor site.

Oligonucleotide: An oligonucleotide is a plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or intersugar linkages, such as a phosphorothioate oligodeoxynucleotide. Functional analogs of naturally occurring polynucleotides can bind to RNA or DNA, and include peptide nucleic acid (PNA) molecules.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 70 bases, for example about 10-25 bases, such as 12, 15 or 20 bases.

Parenteral: Administered outside of the intestine, e.g., not via the alimentary tract. Generally, parenteral formulations are those that will be administered through any possible mode except ingestion. This term especially refers to injections, whether administered intravenously, intrathecally, intramuscularly, intraperitoneally, or subcutaneously, and various surface applications including intranasal, intradermal, and topical application, for instance.

Polymorphism: Variant in a sequence of a gene, usually carried from one generation to another in a population. Polymorphisms can be those variations (nucleotide sequence differences) that, while having a different nucleotide sequence, produce functionally equivalent gene products, such as those variations generally found between individuals, different ethnic groups, or different geographic locations. The term polymorphism also encompasses variations that produce gene products with altered function, i.e., variants in the gene sequence that lead to gene products that are not functionally equivalent. This term also encompasses variations that produce no gene product, an inactive gene product, or increased or decreased activity gene product.

Polymorphisms can be referred to, for instance, by the nucleotide position at which the variation exists, by the change in amino acid sequence caused by the nucleotide variation, or by a change in some other characteristic of the nucleic acid molecule or protein that is linked to the variation (e.g., an alteration of a secondary structure such as a stem-loop, or an alteration of the binding affinity of the nucleic acid for associated molecules, such as polymerases, RNases, and so forth).

Probes and primers: Nucleic acid probes and primers can be readily prepared based on the nucleic acid molecules provided as indicators of disease or disease progression. It is also appropriate to generate probes and primers based on fragments or portions of these nucleic acid molecules. Also appropriate are probes and primers specific for the reverse complement of these sequences, as well as probes and primers to 5' or 3' regions.

A probe comprises an isolated nucleic acid attached to a detectable label or other reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., in Sambrook et al. (In *Molecular Cloning: A Laboratory Manual*, CSHL, New York, 1989) and Ausubel et al. (In *Current Protocols in Molecular Biology*, John Wiley & Sons, New York, 1998).

Primers are short nucleic acid molecules, for instance DNA oligonucleotides 10 nucleotides or more in length. Longer DNA oligonucleotides may be about 15, 20, 25, 30 or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (PCR) or other in vitro nucleic-acid amplification methods known in the art.

Methods for preparing and using nucleic acid probes and primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). Amplification primer pairs (for instance, for use with polymerase chain reaction amplification) can be derived from a known sequence such as FGFR4 or other FGFR sequences (such as those described herein or known to one of ordinary skill), for example, by using computer programs intended for that purpose such as Primer3 (Version 0.4.0,© 2007, Whitehead Institute for Biomedical Research, Cambridge, Mass.).

One of ordinary skill in the art will appreciate that the specificity of a particular probe or primer increases with its length. Thus, for example, a primer comprising 30 consecutive nucleotides of a tyrosine kinase receptor protein-encoding nucleotide will anneal to a target sequence, such as another homolog of the designated tyrosine kinase receptor protein, with a higher specificity than a corresponding primer of only 15 nucleotides. Thus, in order to obtain greater specificity, probes and primers can be selected that comprise at least 20, 23, 25, 30, 35, 40, 45, 50 or more consecutive nucleotides of a tyrosine kinase receptor-encoding nucleotide sequences.

Also provided are isolated nucleic acid molecules that comprise specified lengths of FGFR4-encoding nucleotide sequences. Such molecules may comprise at least 10, 15, 20, 23, 25, 30, 35, 40, 45 or 50 or more (e.g., at least 100, 150, 200, 250, 300 and so forth) consecutive nucleotides of these sequences or more. These molecules may be obtained from any region of the disclosed sequences (e.g., a FGFR4 nucleic acid may be apportioned into halves or quarters based on sequence length, and isolated nucleic acid molecules may be derived from the first or second halves of the molecules, or any of the four quarters, etc.). A cDNA or other encoding sequence also can be divided into smaller regions, e.g. about eighths, sixteenths, twentieths, fiftieths, and so forth, with similar effect.

Another mode of division, provided by way of example, is to divide a FGFR4-encoding sequence based on the regions of the sequence that are relatively more or less homologous to other FGFR or other growth factor receptor sequences.

Another mode of division is to select the 5' (upstream) and/or 3' (downstream) region associated with a FGFR gene (e.g., FGFR4).

Nucleic acid molecules may be selected that comprise at least 10, 15, 20, 25, 30, 35, 40, 50, 100, 150, 200, 250, 300 or more consecutive nucleotides of any of these or other portions of a FGFR4 nucleic acid molecule, such as those disclosed herein, and associated flanking regions. Thus, representative nucleic acid molecules might comprise at least 10 consecutive nucleotides of the FGFR4 cDNA shown in SEQ ID NO: 1.

Rhabdomyosarcoma (RMS): A soft tissue malignant tumor of skeletal muscle origin. The most common primary sites for rhabdomyosarcoma are the head and neck (e.g., parameningeal, orbit, pharyngeal, etc.), the genitourinary tract, and the extremities. Other less common primary sites include the trunk, chest wall, the abdomen (including the retroperitoneum and biliary tract), and the perineal/anal region. There are at least two types of RMS; the most common forms are alveolar RMS (ARMS) and embryonal histological RMS (ERMS). Approximately 20% of children with rhabdomyosarcoma have the ARMS subtype. An increased frequency of this subtype is noted in adolescents and in patients with primary sites involving the extremities, trunk, and perineum/perianal region. ARMS is associated with chromosomal translocations encoding a fusion gene involving FKHR on chromosome 13 and members of the PAX family. The embryonal subtype is the most frequently observed subtype in children, accounting for approximately 60-70% of rhabdomyosarcomas of childhood. Tumors with embryonal histology typically arise in the head and neck region or in the genitourinary tract, although they may occur at any primary site. ERMS is characterized by a younger age at diagnosis, loss of heterozygosity, and altered genomic imprinting.

Sample: A biological specimen containing genomic DNA, RNA (including mRNA), protein, or combinations thereof, obtained from a subject. As used herein, samples include all clinical samples useful for detection of FGFR4 in subjects, including, but not limited to, cells, tissues, and bodily fluids, such as: blood; derivatives and fractions of blood, such as serum; extracted galls; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; or bone marrow aspirates. In a particular example, a sample includes blood obtained from a human subject, such as whole blood or serum. In another particular example, a sample includes buccal cells, for example collected using a swab or by an oral rinse. In a further example, a sample includes a tumor or tumor biopsy, such as a rhabdomyosarcoma.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs or orthologs of human FGFR4 protein, and the corresponding cDNA or gene sequence(s), will possess a relatively high degree of sequence identity when aligned using standard methods. This homology will be more significant when the orthologous proteins or genes or cDNAs are derived from species that are more closely related (e.g., human and chimpanzee sequences), compared to species more distantly related (e.g., human and *C. elegans* sequences).

Methods of alignment of sequences for comparison are well known in the art. Various programs and alignment algorithms are described in: Smith & Waterman *Adv. Appl. Math.* 2: 482, 1981; Needleman & Wunsch *J. Mol. Biol.* 48: 443, 1970; Pearson & Lipman *Proc. Nat. Acad. Sci. USA* 85: 2444, 1988; Higgins & Sharp *Gene,* 73: 237-244, 1988; Higgins & Sharp *CABIOS* 5: 151-153, 1989; Corpet et al. *Nuc. Acids Res.* 16, 10881-90, 1988; Huang et al. *Computer Appls. in the Biosciences* 8, 155-65, 1992; and Pearson et al. *Meth. Mol. Bio.* 24:307-31, 1994. Altschul et al. (*J. Mol. Biol.* 215:403-410, 1990), presents a detailed consideration of sequence alignment methods and homology calculations.

The NCBI Basic Local Alignment Search Tool (BLAST) (Altschul et al. *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx. By way of example, for comparisons of amino acid sequences of greater than about 30 amino acids, the Blast 2 sequences function is employed using the default BLOSUM62 matrix set to default parameters (gap existence cost of 11, and a per residue gap cost of 1). When aligning short peptides (fewer than around 30 amino acids), the alignment is performed using the Blast 2 sequences function, employing the PAM30 matrix set to default parameters (open gap 9, extension gap 1 penalties).

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence remains hybridized to a perfectly matched probe or complementary strand. Conditions for nucleic acid hybridization and calculation of stringencies can be found in Sambrook et al. (In *Molecular Cloning: A Laboratory Manual,* CSHL, New York, 1989) and Tijssen (*Laboratory Techniques in Biochemistry and Molecular Biology—Hybridization with Nucleic Acid Probes* Part I, Chapter 2, Elsevier, New York, 1993). Nucleic acid molecules that hybridize under stringent conditions to a human FGFR4 protein-encoding sequence will typically hybridize to a probe based on either an entire human FGFR4 protein-encoding sequence or selected portions of the encoding sequence under wash conditions of 2×SSC at 50° C.

Nucleic acid sequences that do not show a high degree of sequence identity may nevertheless encode similar amino acid sequences, due to the degeneracy of the genetic code. It is understood that changes in nucleic acid sequence can be made using this degeneracy to produce multiple nucleic acid molecules that all encode substantially the same protein.

Specific binding agent: An agent that binds substantially only to a defined target, such as a FGFR4 nucleic acid or protein. Thus a protein-specific binding agent binds substantially only the specified protein. By way of example, as used herein, the term "FGFR4-protein specific binding agent" includes anti-FGFR4 protein antibodies (and functional fragments thereof) and other agents (such as soluble receptors) that bind substantially only to the FGFR4 protein.

Anti-FGFR4 protein antibodies (or antibodies to another tyrosine kinase, such as FGFR1, FGFR2, or FGFR3) may be produced using standard procedures described in a number of texts, including Harlow and Lane (*Antibodies, A Laboratory Manual*, CSHL, New York, 1988). The determination that a particular agent binds substantially only to the specified protein may readily be made by using or adapting routine procedures. One suitable in vitro assay makes use of the Western blotting procedure (described in many standard texts, including Harlow and Lane (*Antibodies, A Laboratory Manual*, CSHL, New York, 1988)). Western blotting may be used to determine that a given protein binding agent, such as an anti-FGFR4 protein monoclonal antibody, binds substantially only to the FGFR4 protein.

Shorter fragments of antibodies can also serve as specific binding agents. For instance, Fabs, Fvs, and single-chain Fvs (SCFvs) that bind to a specified protein would be specific binding agents. These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. Methods of making these fragments are routine.

Subject: Living multi-cellular vertebrate organisms, a category that includes both human and non-human mammals.

Therapeutically effective amount: An amount of a therapeutic agent (such as an inhibitor of FGFR4), that alone, or together with one or more additional therapeutic agents, induces the desired response, such as decreasing the risk of developing cancer or decreasing the signs and symptoms of cancer, such as decreasing metastasis of a tumor. In one example, it is an amount of a FGFR4 inhibitor needed to induce tumor cell death, inhibit tumor growth, or prevent or delay the metastasis of a tumor, such as rhabdomyosarcoma, breast, prostate, or lung cancer, in a subject. In another example, it is an amount of an inhibitor of FGFR4 needed to cause regression of an existing tumor, or treat one or more signs or symptoms associated with a tumor in a subject, such as a subject having rhabdomyosarcoma, breast, prostate or lung cancer. Ideally, a therapeutically effective amount provides a therapeutic effect without causing a substantial cytotoxic effect in the subject. The preparations disclosed herein are administered in therapeutically effective amounts. In some in vitro examples, the dose of a FGFR4 inhibitor administered to cultured cells may be about 0.1 µM to 500 µM, such as about 1 µM to about 100 µM, for example, about 5 µM. In some examples, the dose of a FGFR4 inhibitor administered to a subject may be about 0.1 mg/kg to about 1000 mg/kg. In particular examples, the dose may be about 1 mg/kg to about 100 mg/kg, such as about 40 mg/kg.

Variant: Any change of the DNA sequence within a gene or chromosome. In some instances, a variant will alter a characteristic or trait (phenotype), but this is not always the case. In some instances, variants are referred to as mutations; the terms are used interchangeably herein. Types of variants include base substitution point mutations (e.g., transitions or transversions), deletions, and insertions. Missense mutations (or variants) are those that introduce a different amino acid into the sequence of the encoded protein; nonsense mutations are those that introduce a new stop codon. In the case of insertions or deletions, mutations can be in-frame (not changing the frame of the overall sequence) or frame shift mutations, which may result in the misreading of a large number of codons (and often leads to abnormal termination of the encoded product due to the presence of a stop codon in the alternative frame).

This term specifically encompasses variations that arise through somatic mutation, for instance those that are found only in disease cells, but not constitutionally, in a given individual. Examples of such somatically-acquired variations include the point mutations that frequently result in altered function of various genes that are involved in development of cancers. This term also encompasses DNA alterations that are present constitutionally, that alter the function of the encoded protein in a readily demonstrable manner, and that can be inherited by the children of an affected individual. In this respect, the term overlaps with "polymorphism," but generally refers to the subset of constitutional alterations that have arisen within the past few generations in a kindred and that are not widely disseminated in a population group. In particular embodiments, the term is directed to those alterations that have major impact on the health of affected individuals.

Variants or mutations can be referred to, for instance, by the nucleotide position at which the variation exists, by the change in amino acid sequence caused by the nucleotide variation, or by a change in some other characteristic of the nucleic acid molecule or protein that is linked to the variation (e.g., an alteration of a secondary structure such as a stem-loop, or an alteration of the binding affinity of the nucleic acid for associated molecules, such as polymerases, RNases, and so forth).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. All publications, patent applications, patents, and other references mentioned herein are incorporated by reference in their entirety for all purposes. Although methods and materials similar or equivalent to those described herein can be used in the practice or testing of the present disclosure, suitable methods and materials are described below. In case of conflict, the present specification, including explanations of terms, will control. In addition, the materials, methods, and examples are illustrative only and not intended to be limiting.

III. Overview of Several Embodiments

Disclosed herein is a method of identifying a subject as a candidate for treatment with an inhibitor of FGFR4 to induce tumor cell death, reduce tumor growth, or decrease risk of metastasis, including determining whether the subject has a variant of FGFR4 that increases risk of metastasis. In some examples, the variant includes a variant amino acid sequence at position(s) 10, 56, 72, 122, 136, 175, 234, 535, 550, 554, or 576 of SEQ ID NO: 2, or a combination thereof. In particular examples, the subject has a variant FGFR4 that includes a variant amino acid in the tyrosine kinase domain (such as a substitution at one or more amino acids including positions 460-746 of SEQ ID NO: 2, for example amino acids, 535, 550, 554 and/or 576). Specific examples of tumors contemplated herein include rhabdomyosarcoma (such as ARMS or ERMS), breast cancer, lung cancer, or prostate cancer.

Also disclosed are methods of identifying a subject as a candidate for treatment with an inhibitor of FGFR4 to induce tumor cell death, reduce tumor growth, or decrease risk of metastasis, including determining whether the subject has altered expression of a variant FGFR4 molecule in a tumor relative to a control sample (such as a non-tumor sample from the subject, a sample from a healthy subject, or a tumor from a subject that does not include a variant FGFR4 molecule). In some examples, the variant includes a variant amino acid sequence at position(s) 10, 56, 72, 122, 136, 175, 234, 535, 550, 554, or 576 of SEQ ID NO: 2, or a combination thereof. In particular examples, the subject has a variant FGFR4 that includes a variant amino acid in the tyrosine kinase domain (such as a substitution at one or more amino acids comprising positions 460-746 of SEQ ID NO: 2, for example amino acids, 535, 550, 554 and/or 576). Specific examples of tumors contemplated herein include rhabdomyosarcoma (such as ARMS or ERMS), breast cancer, lung cancer, or prostate cancer.

In specific examples of these methods, the method involves reacting at least one FGFR4 molecule contained in a clinical sample from the subject with a reagent comprising a FGFR4-specific binding agent to form a FGFR4:agent complex. For instance, the FGFR4 molecule in some instances is a FGFR4 encoding nucleic acid or a FGFR4 protein, and the FGFR4 specific binding agent is a FGFR4 oligonucleotide or a FGFR4 protein specific binding agent. In some embodiments, the sample from the subject includes a neoplastic cell, or is prepared from a neoplastic cell or a sample comprising a neoplastic cell, such as a tumor or tumor biopsy.

In some of the provided methods of detecting a biological condition, the FGFR4 molecule is a FGFR4-encoding nucleic acid sequence. Specific examples of such methods involve using an agent that comprises a labeled nucleotide probe. For instance, the nucleotide probe will in some instances include a sequence as shown in SEQ ID NO: 1, or a fragment thereof that is at least 15 nucleotides in length, and that includes the sequence shown in one or more of position(s) 239, 378, 426, 575, 618, 734, 912, 1814, 1816, 1859, 1860, 1872, or 1938 of SEQ ID NO: 1, or variants at said position(s).

Specific method embodiments involve in vitro amplifying a FGFR4 nucleic acid prior to detecting the FGFR4 variant. By way of example, the FGFR4 nucleic acid is in some cases in vitro amplified using at least one oligonucleotide primer derived from a FGFR4-protein encoding sequence, such as the specific oligonucleotide primers listed herein. Other specific oligonucleotide primers comprise at least 15 contiguous nucleotides from SEQ ID NO: 1. For instance, representative examples of such primers include a sequence as represented by at least 15 contiguous nucleotides shown in one or more of position(s) 239, 378, 426, 575, 618, 734, 912, 1814, 1816, 1859, 1860, 1872, or 1938 of SEQ ID NO: 1, or variants at said position(s). In other examples, such primers include a sequence that amplifies the exon/intron boundaries of a FGFR4 encoding gene, such as represented by SEQ ID NOs: 3-34.

In other method of detection embodiments, the FGFR4 molecule is a FGFR4 protein, for instance a FGFR4 protein comprising a sequence as shown in SEQ ID NO: 2, or variants thereof, such as those described herein. In examples of such methods, the complexes are detected by Western blot assay, ELISA, or immunohistochemistry.

Specific examples of FGFR4-specific binding agents are FGFR4-specific antibodies or a functional fragment thereof, for instance monoclonal antibodies or fragments of monoclonal antibodies. Optionally, such monoclonal antibodies recognize an epitope of a variant FGFR4 and not (or to a lesser extent) an epitope of wild type FGFR4, such as that shown in SEQ ID NO: 2. In particular methods, the antibody is reactive to an epitope including a variant amino acid atone or more of position(s) 10, 56, 72 122, 136, 175, 234, 535, 550, 554, and/or 576 of SEQ ID NO: 2, or an epitope that is specific for the variant due to conformational changes caused by a one of these variant amino acids.

Also provided in the disclosure are kits for detecting at least one variant FGFR4 in a subject using methods described herein. Examples of such kits are used with protein-detection methods, and include at least one FGFR4 protein specific binding agent. For instance, in specific kits the agent (e.g., an antibody) is capable of specifically binding to an epitope within a FGFR4 variant protein but not to an epitope of wild type FGFR4. Thus, some such agents are capable of specifically binding to an epitope within the amino acid sequence shown in SEQ ID NO: 2, or more particularly antigenic fragments of SEQ ID NO: 2 that comprise an amino acid substitution sequence at one or more of position(s) 10, 56, 72, 122, 136, 175, 234, 535, 550, 554, and/or 576 of SEQ ID NO: 2. Examples of the protein-detection kits further include a means for detecting binding of the FGFR4 protein binding agent to a FGFR4 polypeptide.

A further embodiment is a kit for determining whether or not a subject (e.g., an animal, or more particularly a mammal) is a candidate for treatment with a FGFR4 inhibitor to induce tumor cell death, reduce tumor growth, or decrease risk of tumor metastasis associated with a FGFR4 variant by detecting a variant FGFR4 sequence in the subject, which kit includes a container comprising at least one oligonucleotide specific for a FGFR4 sequence; and instructions for using the kit, the instructions indicating steps for performing a method to detect the presence of variant FGFR4 nucleic acid in the sample; and analyzing data generated by the method, wherein the instructions indicate that presence of the variant nucleic acid in the sample indicates that the individual is at increased risk for tumor metastasis. Optionally, such kits further include at least one container that comprises a detectable oligonucleotide. Specific examples of oligonucleotides (labeled or not) that may be included in these kits will be specific for a FGFR4 variant sequence. For instance, particular example oligonucleotides include a sequence specific for a FGFR4 encoding sequence and containing the specific sequence shown in shown at position 239, 378, 426, 575, 618, 734, 912, 1814, 1816, 1859, 1860, 1872, or 1938 of SEQ ID NO: 1, or variants at said position(s).

Another specific embodiment is a kit for determining whether or not a subject (e.g., an animal, or more particularly a mammal) is a candidate for treatment with an inhibitor of FGFR4 to induce tumor cell death, reduce tumor growth, or decrease risk of tumor metastasis, the kit including a container comprising a FGFR4 variant specific antibody; a container comprising a negative control sample; and instructions for using the kit, the instructions indicating steps for: performing a test assay to detect a quantity of FGFR4 variant protein in a test sample of tissue and/or bodily fluid from the subject, performing a negative control assay to detect a quantity of FGFR4 variant protein in the negative control sample; and comparing data generated by the test assay and negative control assay, wherein the instructions indicate that a quantity of FGFR4 variant protein in the test sample more than the quantity of FGFR4 variant protein in the negative control sample indicates that the subject is at increased risk for tumor metastasis. Specific examples of such kits further include one or more detectable antibodies that bind to the antibody specific for FGFR4 variant protein (e.g., to be used in detection of the primary antibody).

Yet another embodiment is a method of screening for a compound useful in influencing (for instance, inhibiting or treating) FGFR4-related tumor growth or metastasis in a mammal, comprising contacting a test compound with the FGFR4 polypeptide or fragment, and determining whether the compound inhibits a FGFR4 protein biological activity (e.g., kinase activity). In certain examples, the test compound is applied to a test cell. Compounds identified or selected by such methods, whether or not formulated for use as therapeutic agents, are also contemplated.

Also provided are compositions that include at least one antigenic fragment of a provided FGFR4 variant protein, which includes a variant amino acid at position(s) 10, 56, 72, 122, 136, 175, 234, 535, 550, 554, and/or 576 of SEQ ID NO: 2.

IV. Methods of Identifying Candidates for Treatment with FGFR4 Inhibitors

A. Detection of Variant FGFR4 Molecules

The presence of FGFR4 gene mutations in RMS strongly suggests that other human cancers will have similar mutations. When present in a cancer, mutant isoforms of FGFR4 represent a therapeutic target for tyrosine kinase inhibitors (TKIs), immunotherapy, and other novel targeted approaches, particularly to decrease risk of tumor metastasis. Because FGFR4 gene mutations are not found in all tumors, the selection of patients for therapy targeting variant FGFR4 isoforms to induce tumor cell death, reduce tumor growth, or decrease risk of metastasis would be optimized by pre-therapy analysis of cancer cells for the presence of FGFR4 gene mutations.

Disclosed herein are methods of identifying subjects (such as a mammal, for example a human subject) for treatment with an inhibitor of FGFR4 to induce tumor cell death, reduce tumor growth, or decrease risk of metastasis, including determining the presence of at least one FGFR4 variant nucleic acid or protein in a sample from the subject (such as a blood or tissue sample, for example, a tumor biopsy).

Such analysis can be based on PCR-based assays for these mutations, using for instance one or more of the following approaches: size fractionation by gel electrophoresis, direct sequencing, single-strand conformation polymorphism (SSCP), high pressure liquid chromatography (including partially denaturing HPLC), allele-specific hybridization, amplification refractory mutation screening, FGFR4 mutation screening by oligonucleotide microarray, restriction fragment polymorphism, MALDI-TOF mass spectrometry, or various related technologies (Abu-Duhier et al., *Br. J. Haematol.*, 113: 983-988, 2001; Kottaridis et al., *Blood*, 98: 1752-1759, 2001; Choy et al., *Ann. Hum. Gen.*, 63: 383-391, 1999; Grompe, *Nature Genetics*, 5: 111-117, 1993; Perlin & Szabady, *Hum. Mutat.*, 19: 361-373, 2002; Amos & and Patnaik, *Hum. Mutat.*, 19: 324-333, 2002; Cotton, *Hum. Mutat.*, 19: 313-314, 2002; Stirewalt et al., *Blood*, 97: 3589-3595, 2001; Hung et al., *Blood Coagul. Fibrinolysis*, 13: 117-122, 2002; Larsen et al., *Pharmacogenomics*, 2: 387-399, 2001; Shchepinov et al., *Nucleic Acids Res.*, 29: 3864-3872, 2001).

In addition, mutant or variant FGFR4 proteins may be detected through novel epitopes recognized by polyclonal and/or monoclonal antibodies used in ELISA, immunoblotting, flow cytometric, immunohistochemical and other mutant protein detection strategies (Wong et al., *Cancer Res.*, 46: 6029-6033, 1986; Luwor et al., *Cancer Res.*, 61: 5355-5361, 2001; Mishima et al., *Cancer Res.*, 61: 5349-5354, 2001; Ijaz et al., *J. Med. Virol.*, 63: 210-216, 2001). Additionally variant FGFR4 proteins could be detected by mass spectrometry assays coupled to immunoaffinity assays, the use of matrix-assisted laser desorption/ionization time-of-flight (MALDI-TOF) mass mapping and liquid chromatography/quadrupole time-of-flight electrospray ionization tandem mass spectrometry (LC/Q-TOF-ESI-MS/MS) sequence tag of tumor derived proteins separated by two-dimensional polyacrylamide gel electrophoresis (2D-PAGE) (Kiernan et al., *Anal. Biochem.*, 301: 49-56, 2002; Poutanen et al., *Mass Spectrom.*, 15: 1685-1692, 2001). All of these approaches may be used to detect a sequence anomaly or variant of the FGFR4 protein, a relative increase in the phosphorylation of the protein, or an increase in the inherent kinase activity of the protein.

In addition to direct detection of variant FGFR4 proteins, it is expected that various FGFR4 variants will result in distinctive signal transduction profiles that could be detected by global gene expression profile or analysis of the activation or phosphorylation of various signaling intermediates (e.g., Stat3, Akt, ERK1/2, or S6K).

It is believed that the nature and location of FGFR4 mutations affects the sensitivity of the resultant mutant protein to various TKIs. In some examples, a TKI may selectively inhibit a variant FGFR4 protein, such that the TKI inhibits tyrosine kinase activity of a variant FGFR4 protein to a greater extent than it inhibits a wild type FGFR4. For example, the FGFR inhibitor PD173074 has been shown to inhibit tyrosine kinase receptors, including FGFRs, platelet-derived growth factor (PDGF) receptors, and vascular endothelial growth factor (VEGF) receptors (Mohammadi et al., *EMBO J.* 17:5896-5904, 1998). In some examples PD173074 inhibits a variant FGFR4 (for example FGFR4 TK domain variants, such as N535K, N535D, V550E, V550L, A554V, and/or G576D) to a greater extent than PD173074 inhibits a wild type FGFR4. In some examples, the inhibitory effect of the compound is determined by direct assessment of tyrosine kinase activity. In additional examples, the inhibitory effect is determined by other assays, such as cell growth, apoptosis, or tumor metastasis assays, such as those described herein.

B. Detection of Altered Expression of FGFR4 Molecules

Disclosed herein are methods of identifying subjects (such as a mammal, for example a human subject) for treatment with an inhibitor of FGFR4 to induce tumor cell death, reduce tumor growth, or decrease risk of metastasis, including determining altered expression of variant FGFR4 nucleic acid or protein in a sample from the subject (such as a blood or tissue sample, for example, a tumor biopsy). In particular examples, the variant includes a variant amino acid sequence at position (s) 10, 56, 72, 122, 136, 175, 234, 535, 550, 554, or 576 of SEQ ID NO: 2, or a combination of two or more thereof. In some examples, the subject has a variant FGFR4 that comprises a variant amino acid in the tyrosine kinase domain (such as a substitution at one or more amino acids comprising positions 460-746 of SEQ ID NO: 2, for example amino acids 535, 550, 554 and/or 576). In some examples, expression of the variant FGFR4 is compared to expression of FGFR4 in a normal control (such as skeletal muscle, if the tumor is a rhabdomyosarcoma). In other examples, expression of the variant FGFR4 is compared to expression of FGFR4 in a tumor that does not express a variant FGFR4 molecule.

In particular examples, an increase in expression of a variant FGFR4 molecule relative to a control (such as FGFR4 expression in a non-tumor tissue) indicates that the subject is a candidate for treatment with an inhibitor of FGFR4 to induce tumor cell death, reduce tumor growth, or decrease risk of metastasis. In other examples, a decrease in expression of a variant FGFR4 molecule relative to a control (such as wild type FGFR4 expression in a tumor) indicates that the subject is a candidate for treatment with an inhibitor of FGFR4 to induce tumor cell death, reduce tumor growth, or decrease risk of metastasis.

Such analysis can be based on PCR-based assays for these mutations, using for instance quantitative real-time PCR. See e.g. Bange et al., *Cancer Res.* 62:840-847, 2002. In some examples, primers and probes comprise at least 15 contiguous nucleotides of SEQ ID NO: 1. In particular examples, primers and probes comprise SEQ ID NOs: 38-43.

In addition, overexpression of FGFR4 proteins may be detected through novel epitopes recognized by polyclonal and/or monoclonal antibodies used in ELISA, immunoblotting, flow cytometric, immunohistochemical and other mutant protein detection strategies (Wong et al., *Cancer Res.,* 46: 6029-6033, 1986; Luwor et al., *Cancer Res.,* 61: 5355-5361, 2001; Mishima et al., *Cancer Res.,* 61: 5349-5354, 2001; Ijaz et al., *J. Med. Virol.,* 63: 210-216, 2001).

V. Screening Methods

Disclosed herein are methods for identifying compounds that inhibit tumor growth or metastasis. The methods include contacting a test compound with a FGFR4 polypeptide (for example a polypeptide encoded by a FGFR4 gene, such as SEQ ID NO: 1, for example, the polypeptide of SEQ ID NO: 2). In particular examples, the FGFR4 polypeptide includes a variant that increases risk of tumor metastasis. A compound that is an inhibitor of tumor metastasis may be identified by determining the effect of a test compound on activity of the FGFR4 polypeptide variant (including ligand binding or tyrosine kinase activity). In a particular example, a test compound that inhibits tyrosine kinase activity as compared to activity in the absence of the test compound identifies the test compound as an inhibitor of tumor metastasis. If the compound inhibits activity of a FGFR4 variant, it is further evaluated for its ability to inhibit tumor growth or metastasis.

A. In General

Activating tyrosine kinase mutants, including for instance the novel FGFR4 variants described herein, are useful to identify compounds that can be used to treat, ameliorate, or prevent neoplasms, for example by inhibiting or preventing metastasis.

The screening or creation, identification and selection of appropriate high affinity inhibitors of FGFR4 variants can be accomplished by a variety of methods. Broadly speaking these may include, but are not limited to, two general approaches. One approach is to use structural knowledge about the target protein to design a candidate molecule with which it will precisely interact. An example would be computer assisted molecular design. A second approach is to use combinatorial or other libraries of molecules, whereby a large library of molecules is screened for affinity with regard to the target enzyme, or ability to inhibit activity of the target enzyme. In a further example, a panel of antibodies may be screened for ability to inhibit the target enzyme.

Cancer and precancer may be thought of as diseases that involve unregulated cell growth. Metastasis involves migration of tumor cells away from the site of the primary tumor, entry into the circulation, and proliferation at a new site. Cell growth involves a number of different factors. One factor is how rapidly cells proliferate, and another involves how rapidly cells die. Cells can die either by necrosis or apoptosis depending on the type of environmental stimuli. Cell motility is yet another factor that influences tumor growth kinetics and metastasis. Resolving which of the many aspects of cell growth a test compound affects can be important to the discovery of a relevant target for pharmaceutical therapy. Screening assays based on this technology can be combined with other tests to determine which compounds have growth inhibiting and pro-apoptotic activity.

B. Inhibitor Screening

Some embodiments provided herein involve determining the ability of a given compound to inhibit FGFR4 variants, for instance the ability to specifically inhibit constitutive kinase and/or metastasis promoting activities in the FGFR4 Ile10Val, Cys56Ser, Arg72Leu, Thr122Ala, Leu136Pro, Ala175Thr, Arg234His, Gly368Arg, Arg529Gln, Asn535Asp, Asn535Lys, Val550Glu, Val550Leu, Ala554Val, Gly576Asp variants described herein. Test compounds can be assessed for their probable ability to treat neoplastic lesions either directly, or indirectly by comparing their activities against compounds known to be useful for treating neoplasia. In particular, the compounds are tested for their ability to inhibit metastasis of a tumor that contains a FGFR4 variant that increases risk of metastasis.

C. Determining Tyrosine Kinase Influencing Activity

Compounds can be screened for inhibitory or other effects on the activity of the novel FGFR4 variants described herein using an expressed recombinant version of the enzyme, or a homolog or ortholog isolated from another species. Alternatively, cells expressing one of these FGFR4 polypeptides can be treated with a test compound and the effect of the test compound on phosphorylation of a specific target can be determined, for instance using one of the techniques described herein. In one example, tyrosine kinase activity is determined. Methods for determining tyrosine kinase phosphorylation influencing activity (e.g., inhibition) are known to one of skill in the art. In some examples, tyrosine kinase activity may be determined by assessing incorporation of a labeled phosphate (such as $^{32}$P-labeled phosphate) into a substrate which is capable of being phosphorylated by FGFR4 (such as a protein or a peptide fragment). In additional examples, tyrosine kinase activity may be determined by assessing FGFR4 autophosphorylation. In a further example, tyrosine kinase activity may be determined by assessing phosphorylation of downstream signaling components (such as Akt or MAP kinase). In additional examples, FGFR4 tyrosine kinase activity can be measured using a universal tyrosine kinase activity kit (for example, Universal Tyrosine Kinase Assay Kit (Takara Bio, Inc., Madison, Wis.); Tyrosine Kinase Assay Kit (Millipore, Billerica, Mass.)).

D. Determining Whether a Compound Reduces the Number of Tumor Cells

In an alternate embodiment, provided screening methods involve further determining whether the compound reduces the growth of tumor cells, for instance tumor cells known to express an activated tyrosine kinase mutation such as a mutation in FGFR4.

Various cell lines can be used, which may be selected based on the tissue to be tested. For example, these cell lines include: RMS cell lines (such as RH28, RH41, RH30, RH36, and RD cells), lung cancer cell lines (for example, A-427 or A549 cells), breast cancer cell lines (such as MCF-7 or MDA-MB-134 cells), or prostate cancer cell lines (such as DU145 cells). Cell lines can also be constructed that express variant FGFR4 proteins, for example, cell lines from a mouse model of RMS (such as RMS119 or RMS772 cells) that express human FGFR4 or FGFR4 variants. Certain cell lines are well characterized, and are used for instance by the United States National Cancer Institute (NCI) in their screening program for new anti-cancer drugs. Though a compound may be identified by its ability to inhibit a specific FGFR4 variant, its activity likely will not be limited to inhibition of only that mutant protein, thus testing in different cell lines and samples is beneficial to determine the scope of its activity.

Significant tumor cell growth inhibition, greater than about 30% at a dose of 100 μM or below, is further indicative that the compound is useful for treating neoplastic lesions. An $IC_{50}$ value may be determined and used for comparative purposes. This value is the concentration of drug needed to inhibit tumor cell growth by 50% relative to the control. In some embodiments, the $IC_{50}$ value is less than 100 μM in order for the compound to be considered further for potential use for treating, ameliorating, or preventing neoplastic lesions or tumor metastasis.

E. Determining Whether a Test Compound Induces Apoptosis

In other embodiments, screening methods provided herein further involve determining whether the test compound induces apoptosis in cultures of tumor cells.

Two distinct forms of cell death may be described by morphological and biochemical criteria: necrosis and apoptosis. Necrosis is accompanied by increased permeability of the plasma membrane, whereby the cells swell and the plasma membrane ruptures within minutes. Apoptosis is characterized by membrane blebbing, condensation of cytoplasm, and the activation of endogenous endonucleases.

Apoptosis occurs naturally during normal tissue turnover and during embryonic development of organs and limbs. Apoptosis also can be induced by various stimuli, including cytotoxic T-lymphocytes and natural killer cells, by ionizing radiation and by certain chemotherapeutic drugs. Inappropriate regulation of apoptosis is thought to play an important role in many pathological conditions including cancer, AIDS, or Alzheimer's disease, etc.

Test compounds can be screened for induction of apoptosis using cultures of tumor cells maintained under conditions as described above. In some examples of such screening methods, treatment of cells with test compounds involves either pre- or post-confluent cultures and treatment for one to seven days at various concentrations of the test compounds. Apoptotic cells can be measured in both the attached and "floating" portions of the cultures. Both are collected by removing the supernatant, trypsinizing the attached cells, and combining both preparations following a centrifugation wash step (10 minutes, 2000 rpm).

Following treatment with a test compound, cultures can be assayed for apoptosis and necrosis, for instance by florescent microscopy following labeling with acridine orange and ethidium bromide. Many methods for measuring apoptotic cells are known to those of ordinary skill in the art; for instance, one method for measuring apoptotic cell number has been described by Duke & Cohen (*Curr. Prot. Immuno.*, Coligan et al., eds., 3.17.1-3.17.1, 1992).

For example, floating and attached cells are collected by trypsinization and washed three times in PBS. Aliquots of cells are then centrifuged. The pellet is resuspended in media and a dye mixture containing acridine orange and ethidium bromide prepared in PBS and mixed gently. The mixture then can be placed on a microscope slide and examined for morphological features of apoptosis.

Apoptosis also can be quantified by measuring an increase in DNA fragmentation in cells that have been treated with test compounds. Commercial photometric enzyme immunoassays (EIA) for the quantitative in vitro determination of cytoplasmic histone-associated-DNA-fragments (mono- and oligo-nucleosomes) are available (e.g., Cell Death Detection ELISA, Boehringer Mannheim). The Boehringer Mannheim assay is based on a sandwich-enzyme-immunoassay principle, using mouse monoclonal antibodies directed against DNA and histones, respectively. This allows the specific determination of mono- and oligo-nucleosomes in the cytoplasmic fraction of cell lysates. According to the vendor, apoptosis is measured as follows: The sample (cell-lysate) is placed into a streptavidin-coated microtiter plate ("MTP"). Subsequently, a mixture of anti-histone-biotin and anti-DNA peroxidase conjugates is added and incubated for two hours. During the incubation period, the anti-histone antibody binds to the histone-component of the nucleosomes and simultaneously fixes the immunocomplex to the streptavidin-coated MTP via its biotinylation. Additionally, the anti-DNA peroxidase antibody reacts with the DNA component of the nucleosomes. After removal of unbound antibodies by a washing step, the amount of nucleosomes is quantified by the peroxidase retained in the immunocomplex. Peroxidase is determined photometrically with ABTS7 (2,2'-Azido-[3-ethyl-benzthiazolin-sulfonate]) as substrate.

Statistically significant increases of apoptosis (i.e., greater than 2 fold stimulation at a test compound concentration of 100 μM) are further indicative that the compound is useful for treating neoplastic lesions. Preferably, the $EC_{50}$ value for apoptotic activity should be less than 100 μM for the compound to be further considered for potential use for treating neoplastic lesions. $EC_{50}$ is understood herein to be the concentration that causes 50% induction of apoptosis relative to vehicle treatment.

F. Determining Whether a Compound Decreases Tumor Metastasis

In additional embodiments, screening methods provided herein further include determining whether the test compound decreases tumor metastasis, for example in an animal model of metastasis.

Methods for assessing tumor metastasis are known to one of skill in the art (see e.g. Khanna and Hunter, *Carcinogenesis* 26:513-523, 2005). One model of metastasis involves human-mouse xenografts, in which human cancer cell lines or tissues are transplanted into immunocompromised mice (such as SCID mice or nude mice). In similar methods, a cell line that has been engineered to express a molecule of interest (such as a FGFR4 polypeptide or a FGFR4 variant polypeptide) is transplanted into an immunocompromised mouse. In one example, tumor cells or cell lines are injected directly into the systemic circulation. The site of injection largely defines the site to which metastases develop in these experimental systems. The most common site of tumor cell injection employed for experimental metastasis models is the lateral tail vein in mice, which results primarily in pulmonary metastases. In contrast, intrasplenic or portal vein injection of tumor cells is the most common site employed for developing metastasis in the liver and intracardiac injection of cells may result in metastases to several sites, including bone. Following injection of tumor cells or other cell lines into the circulation, development of metastases at the site of interest (such as lung) is monitored over a period of days or weeks.

Another model for assessing tumor metastasis utilizes orthotopic transplantation, wherein cancer cells are transplanted to the anatomic location or tissue from which a tumor was derived (for example by direct injection or surgical implantation of tumor fragments). Spontaneous metastases that arise from the orthotopic tumor can be assessed over a period of days or weeks.

The ability of a test compound to decrease or prevent tumor metastasis may be assessed by administering a test compound to an animal following injection of tumor cells subcutaneously, intramuscularly, or into the circulation or by orthotopic transplantation. The number, size, or time of development of metastases may be assessed. A compound that inhibits tumor metastasis may decrease the number of metastases, for example by at least 10%, 20%, 30%, 40%, 50%, 60%, 70% 80%, 90%, 95%, or even 100% as compared to a control sample. A compound that inhibits tumor metastasis may also decrease the size of metastases as compared to a control sample. Similarly, a compound that inhibits tumor metastasis may delay the onset of development of metastases, for example by at least one week, two weeks, one month, six months, one year, or even indefinitely.

VI. FGFR4 Inhibitors

The methods disclosed herein include identifying a subject as a candidate for treatment with an inhibitor of FGFR4 to induce tumor cell death, reduce tumor growth, or decrease risk of tumor metastasis. Inhibitors of tyrosine kinase receptors (such as growth factor receptors, such as FGFRs, for example, FGFR1, FGFR2, FGFR3, or FGFR4) are known to one of skill in the art.

A. Small Organic Molecule Inhibitors

Inhibitors of growth factor receptors may include small organic molecules. Some small molecule inhibitors may inhibit multiple growth factor receptors, while others may be specific for a particular family of growth factor receptor (for example, FGFRs), and still others may be specific for one growth factor receptor subtype (such as FGFR1, FGFR2, FGFR3, or FGFR4). In particular examples, a small molecule inhibitor specifically inhibits FGFR4 activity (such as TK activity). In still further examples, the small molecule inhibitor specifically inhibits FGFR4 variants that increase risk for tumor metastasis (such as variants in the TK domain, for example, variants at position N535, V550, A554 and/or G576).

In some examples, the small molecule inhibitor of FGFR4 or FGFR4 variants is a previously identified growth factor receptor or FGFR inhibitor. In some examples, the inhibitor is SU5402 (3-[3-(2-Carboxyethyl)-4-methylpyrrol-2-methylidenyl]-2-indolinone). In another example the inhibitor is TKI258 (4-amino-5-fluoro-3-[5-(4-methylpiperazin-1-yl)-1H-benzimidazol-2-yl]quinolin-2(1H)-one, also known as CHIR-258). In a further example, the inhibitor is PD173074 (1-tert-butyl-3-[6-3,5-dimethoxyphenyl)-2-(4-diethylamino-butylamino)-pyrido[2,3-d]pyrimidin-7-yl]-urea; Mohammadi, et al., *EMBO J.* 17:5896-5904, 1998). In another example, the inhibitor is imatinib (4-[(4-methylpiperazin-1-yl)methyl]-N-[4-methyl-3-[(4-pyridin-3-ylpyrimidin-2-yl)amino]-phenyl]-benzamide). Additional FGFR inhibitors (such as FGFR4 inhibitors or FGFR4 variant inhibitors) may be identified utilizing the methods described herein.

Appropriate dosages for treatment with small organic molecules can be determined by one of skill in the art. In general, an effective amount of a composition that includes a FGFR4 small molecule inhibitor administered to a subject will vary depending upon a number of factors associated with that subject, for example the overall health of the subject, the condition to be treated, or the severity of the condition. An effective amount of a composition that includes a FGFR4 inhibitor can be determined by varying the dosage of the compound and measuring the resulting therapeutic response, such as the decrease in metastasis of cancer, such as rhabdomyosarcoma, breast cancer, lung cancer, or prostate cancer, or the decrease in the size, volume or number of tumors. FGFR4 inhibitors can be administered in a single dose, or in several doses, as needed to obtain the desired response. However, the effective amount can be dependent on the source applied, the subject being treated, the severity and type of the condition being treated, and the manner of administration. In some examples, the dose of a FGFR4 inhibitor administered to a subject may be about 0.1 mg/kg to about 1000 mg/kg. In particular examples, the dose may be about 1 mg/kg to about 100 mg/kg, such as about 40 mg/kg.

In a further example, a therapeutically effective dose of a FGFR4 inhibitor includes daily use for at least about three months, such as at least about three months, about six months, about one year, about two years, about three years, about four years, or about five years. The disclosed compositions that include a FGFR4 small molecule inhibitor can be administered alone, in the presence of a pharmaceutically acceptable carrier, in the presence of other therapeutic agents (for example other anti-cancer therapeutic agents), or both. Such anti-cancer therapeutics include, but are not limited to, chemotherapeutic drug treatment, radiation, gene therapy, hormonal manipulation, immunotherapy and antisense oligonucleotide therapy. Examples of useful chemotherapeutic drugs include, but are not limited to, hydroxyurea, busulphan, cisplatin, carboplatin, chlorambucil, melphalan, cyclophosphamide, Ifosphamide, danorubicin, doxorubicin, epirubicin, mitoxantrone, vincristine, vinblastine, Navelbine® (vinorelbine), etoposide, teniposide, paclitaxel, docetaxel, gemcitabine, cytosine, arabinoside, bleomycin, neocarcinostatin, suramin, taxol, mitomycin C and the like. The compounds of the invention are also suitable for use with standard combination therapies employing two or more chemotherapeutic agents. It is to be understood that anti-cancer therapeutics for use in the present invention also include novel compounds or treatments developed in the future.

B. Antibody Inhibitors of FGFR4

In additional examples, inhibitors of FGFRs may include FGFR4-specific binding agents, such as polyclonal or monoclonal antibodies.

Specific examples of FGFR4-specific binding agents are FGFR4-specific antibody or a functional fragment thereof, for instance monoclonal antibodies or fragments of monoclonal antibodies. Optionally, such monoclonal antibodies recognize an epitope of a variant FGFR4 (such as an epitope of a variant FGFR4 having an amino acid substitution in at least one position, including, but not limited to, amino acid(s) 10, 56, 72, 122, 136, 175, 234, 535, 550, 554, or 576 of SEQ ID NO: 2, or a combination thereof), and not (or to a lesser extent) an epitope of wild type FGFR4.

Monoclonal or polyclonal antibodies may be produced to either the normal FGFR4 protein or mutant forms of this protein, for instance particular portions that contain a mutation and therefore may provide a distinguishing epitope. Optimally, antibodies raised against these proteins or peptides would specifically detect the protein or peptide with which the antibodies are generated. That is, an antibody generated to the FGFR4 protein or a fragment thereof would recognize and bind the FGFR4 protein and would not substantially recognize or bind to other proteins found in human cells. In some embodiments, an antibody is specific for (or measurably preferentially binds to) an epitope in a variant protein versus the wild type protein, or vice versa, as discussed more fully herein.

Appropriate dosages for treatment with antibodies can be determined by one of skill in the art. In general, an effective amount of a composition that includes a FGFR4 antibody administered to a subject will vary depending upon a number of factors associated with that subject, for example the overall health of the subject, the condition to be treated, or the severity of the condition. An effective amount of a composition that includes a FGFR4 antibody can be determined by varying the dosage of the compound and measuring the resulting therapeutic response, such as the decrease in metastasis of cancer, such as rhabdomyosarcoma, breast cancer, lung cancer, or prostate cancer, or the decrease in the size, volume or number of tumors. FGFR4 antibodies can be administered alone, in the presence of a pharmaceutically acceptable carrier, in the presence of other therapeutic agents (for example other anti-cancer therapeutic agents), or both. Such anti-cancer therapeutics include, but are not limited to, chemotherapeutic drug treatment, radiation, gene therapy, hormonal manipulation, immunotherapy and antisense oligonucleotide therapy. Examples of useful chemotherapeutic drugs include, but are not limited to, hydroxyurea, busulphan, cisplatin, carboplatin, chlorambucil, melphalan, cyclophosphamide, Ifosphamide, danorubicin, doxorubicin, epirubicin, mitoxantrone, vincristine, vinblastine, Navelbine® (vinorelbine), etoposide, teniposide, paclitaxel, docetaxel, gemcitabine, cytosine, arabinoside, bleomycin, neocarcinostatin, suramin, taxol, mitomycin C and the like. The compounds of the invention are also suitable for use with standard combination therapies employing two or more chemotherapeutic agents. It is to be understood that anti-cancer therapeutics for use in the present invention also include novel compounds or treatments developed in the future.

The following examples are provided to illustrate certain particular features and/or embodiments. These examples should not be construed to limit the invention to the particular features or embodiments described.

EXAMPLES

Analysis of gene expression patterns have led to improved accuracy of tumor identification and advanced the understanding of RMS biology, especially metastatic regulators. Artificial neural networks can distinguish unique gene expression profiles from different small round blue cell tumors of childhood including RMS. Expression profiling has also revealed a unique signature for PAX-FKHR positive aleveolar RMS tumors compared to those lacking this fusion gene. One gene unique to all of these gene expression studies is FGFR4, a protein tyrosine kinase member of the FGFR gene family. High levels of mRNA correlate with FGFR4 protein expression, leading to speculation that FGFR4 could be a tumor specific diagnostic marker, a determinant of tumor biology, or both. In other human cancers, the presence of a common genetic variant (FGFR4 G388R) is associated with increased tumor cell motility and prognosis in patients with soft tissue sarcomas, colon cancer, or breast cancer (Bange et al., *Cancer Res.* 62:840-847, 2992; Morimoto et al., *Cancer* 98:2245-2250, 2003; Thussbas et al., *J. Clin. Oncol.* 24:3747-3755, 2996). Together, these data suggest that altered FGFR4 function is important in the development or prognosis of soft tissue sarcomas.

Example 1

FGFR4 Overexpression and Mutation in Rhabdomyosarcoma

This example describes analysis of FGFR4 gene expression in human rhabdomyosarcoma (RMS) tumors and identification of FGFR4 mutations in RMS.

Methods

Ninety four primary RMS tumors were obtained for genomic DNA extraction from the Cooperative Human Tissue Network (CHTN, Columbus, Ohio) and the Children's Hospital at Westmead (Westmead, Australia). Fifty of these primary RMS tumors had matching germline genomic DNA, also obtained from CHTN. 12 RMS cell lines (A204, A673, RH1, RH4, RH30, RD, RH5, RH13, RH18, RH28, RH36, RH41) were also obtained for genomic DNA extraction. Healthy, anonymous controls were comprised of 284 European/European American, 30 North African, 333 African/African American, 143 Middle Eastern, 175 Asian, and 65 Hispanic/Native American.

Up to 70 milligrams from each frozen primary tumor sample was homogenized in 0.7 ml Trizol® reagent (Invitrogen; Carlsbad, Calif.). Tumor cell lines were grown to 80% confluence, washed with PBS and resuspended in 0.7 ml Trizol® reagent. Total RNA was purified with miRNEasy® kit (Qiagen, Valencia, Calif.). Genfind™ DNA isolation kits (Agencourt, Beverly, Mass.) were used to purify genomic DNA from tumor samples and paired white cell buffy coat preparations.

Total cellular RNA was isolated as described above, biotin labeled, and hybridized to GeneChip® Human U133A Expression Arrays according to the manufacturers recommended protocol (Affymetrix, Santa Clara, Calif.).

PCR primers for 17 FGFR4 protein coding exons are presented in Table 1. Each forward primer has M13 forward universal sequencing tag added to the 5' end, each reverse primer has M13 reverse universal sequencing tag added to the 5' end. Genomic DNA was amplified by PCR using a MJ Research model PTC-225 thermal cyclers (Bio-Rad Laboratories, Inc., Waltham, Mass.) and standardized SNP500Cancer PCR conditions (snp500cancer.nci.nih.gov/home.cfm) as follows: 10 ng of genomic DNA, 0.2 mM of each primer, 200 mM of each dNTP, 2 mM MgCl2, 0.5 U AmpliTaq Gold® DNA polymerase (ABI-Perkin Elmer, Foster City, Calif.), and the manufacturer's buffer. PCR reaction conditions included an initial 10 minutes at 95° C.; 40 cycles of 95° C.×30 seconds, a uniform annealing temperature for all primer pairs at 65° C.×30 seconds, 72° C.×150 seconds, and a final extension at 72° C. for 10 minutes. Sequencing of amplified DNA using BigDye® Terminator chemistry (ABI-Perkin Elmer, Foster City, Calif.) and M13 forward or reverse primers was performed on ABI-Perkin Elmer platforms (models 3100, 3700, and/or 3730) and analyzed with Sequence Analysis 3.7 (ABI-Perkin Elmer) and Sequencher™ 4.5 software (Gene Codes Corp., Ann Arbor, Mich.). Twenty percent of samples were sequenced in duplicate, and all missense or singleton mutations were confirmed with replicate PCR/sequencing.

TABLE 1

Primers Used for PCR Amplification and Sequencing PCR of FGFR4.

| Amplicon Name | Primer Name | Primer Sequence |
|---|---|---|
| Exon 2 | Exon2 Forward | TGTAAAACGACGGCCAGTGGCCACTTCCTGTCT CAGTTTCC (SEQ ID NO: 3) |
|  | Exon2 Reverse | CAGGAAACAGCTATGACCCTGGGCAAGGATCCT TTCCAGC (SEQ ID NO: 4) |
| Exon 3 | Exon3 Forward | TGTAAAACGACGGCCAGTGGTCAAGGAGTCTAC ATCAGGG (SEQ ID NO: 5) |
|  | Exon3 Reverse | CAGGAAACAGCTATGACCCCTTCAGCATGCGTT GCAAAG (SEQ ID NO: 6) |
| Exon 4 | Exon4 Forward | TGTAAAACGACGGCCAGTCTCACCTTGATTACA GGTGG (SEQ ID NO: 7) |
|  | Exon4 Reverse | CAGGAAACAGCTATGACCGTTTCTTCTCCATGC GCTG (SEQ ID NO: 8) |
| Exon 5 | Exon5 Forward | TGTAAAACGACGGCCAGTCAGTAGGTCTCCAAG GAC (SEQ ID NO: 9) |
|  | Exon5 Reverse | CAGGAAACAGCTATGACCCCGCAATCGCTTCAC TCATTCG (SEQ ID NO: 10) |
| Exon 6 | Exon6 Forward | TGTAAAACGACGGCCAGTGTTCTCAGGGCCTAG AGAG (SEQ ID NO: 11) |
|  | Exon6 Reverse | CAGGAAACAGCTATGACCCTCACCAAGCTGCCT GACTC (SEQ ID NO: 12) |
| Exon 7 | Exon7 Forward | TGTAAAACGACGGCCAGTGAGACAGACAAGAAG CTGCAG (SEQ ID NO: 13) |
|  | Exon7 Reverse | CAGGAAACAGCTATGACCCCACCTCTGAGCTAT TGATGTC (SEQ ID NO: 14) |
| Exon 8 | Exon8 Forward | TGTAAAACGACGGCCAGTCATTCTTCTCCCACC TTGGG (SEQ ID NO: 15) |
|  | Exon8 Reverse | CAGGAAACAGCTATGACCCCCACAAATCCACAC ACTG (SEQ ID NO: 16) |
| Exon 9/ Exon 10 | Exon9_10 Forward | TGTAAAACGACGGCCAGTGCTGGGAGGGACTGA GTTAG (SEQ ID NO: 17) |
|  | Exon9_10 Reverse | CAGGAAACAGCTATGACCTGGAGAAAGTCCAGC CTCAG (SEQ ID NO: 18) |
| Exon 11 | Exon11 Forward | TGTAAAACGACGGCCAGTCTACCTCTCGACCCAC TATG (SEQ ID NO: 19) |
|  | Exon11 Reverse | CAGGAAACAGCTATGACCGTCTTGCCATGTTGCC CAGG (SEQ ID NO: 20) |
| Exon 12 | Exon12 Forward | TGTAAAACGACGGCCAGTGATTCAGCCCTAGACC TACG (SEQ ID NO: 21) |
|  | Exon12 Reverse | CAGGAAACAGCTATGACCCACTCCACGATCACGT AC (SEQ ID NO: 22) |
| Exon 13 | Exon13 Forward | TGTAAAACGACGGCCAGTCAACCTGCTTGGTGTC TG (SEQ ID NO: 23) |
|  | Exon13 Reverse | CAGGAAACAGCTATGACCGGAAAGCGTGAATGCC TG (SEQ ID NO: 24) |
| Exon 14 | Exon14 Forward | TGTAAAACGACGGCCAGTCTAACCCTTGACCTCC TCCTCTG (SEQ ID NO: 25) |
|  | Exon14 Reverse | CAGGAAACAGCTATGACCCATCCACTTCACAGGC AG (SEQ ID NO: 26) |
| Exon 15 | Exon15 Forward | TGTAAAACGACGGCCAGTCCAGCAACGTGAGGGA GATG (SEQ ID NO: 27) |
|  | Exon15 Reverse | CAGGAAACAGCTATGACCCCAAATCTGAAGGAGC CCTCG (SEQ ID NO: 28) |
| Exon 16 | Exon16 Forward | TGTAAAACGACGGCCAGTGGCTCCTTCAGATTTG GTCTG (SEQ ID NO: 29) |
|  | Exon16 Reverse | CAGGAAACAGCTATGACCGTTAGTGTTGTCCTTC TGGCC (SEQ ID NO: 30) |
| Exon 17 | Exon17 Forward | TGTAAAACGACGGCCAGTCTACTGATGACCCTCC TATC (SEQ ID NO: 31) |
|  | Exon17 Reverse | CAGGAAACAGCTATGACCGAATAGGGTCCGAAGG TCAG (SEQ ID NO: 32) |
| Exon 18 | Exon18 Forward | TGTAAAACGACGGCCAGTGTCTCTGAGGAGGTAC AGC (SEQ ID NO: 33) |
|  | Exon18 Reverse | CAGGAAACAGCTATGACCGACACGGCACAGCAAC TCTG (SEQ ID NO: 34) |
| M13 | M13 Forward | TGTAAAACGACGGCCAGT (SEQ ID NO: 35) |
|  | M13 Reverse | CAGGAAACAGCTATGACC (SEQ ID NO: 36) |

All tumors with an FGFR4 TK domain mutation were subject to RT-PCR for the presence of known PAX-FOXO1 fusion genes as previously described, modified by the use of the 3' FOXO1 primer, ATGAACTTGCTGTGTAGGGACAG (SEQ ID NO: 37; Barr et al., *Am. J. Clin. Pathol.* 104:627-633, 1995). RT-PCR products (PAX3/FOXO1=172 bp and PAX7/FOXO1=160 bp) were resolved on an Agilent Bioanalyzer 2100 and analyzed with DNA 1000 Lab-on-chip software (Agilent Technologies, Santa Clara, Calif.).

Copy number variation (CNV) in FGFR4 regions of Hardy-Weinberg disequilibrium was determined by Real-Time PCR Gene Copy Number Assay on the 7900HT (Applied Biosystems, Foster City, Calif.). RnaseP, with an established gene copy number of 2 in most of the human population, was an internal control. Primers pairs and probes for the target gene and the internal control were designed to avoid known variant nucleotide sites. The target gene probe was FAM labeled and the internal control probe was VIC labeled. Patient DNA, target gene and internal control primers, and target gene and internal control gene probes for were mixed in an Optical 96-well reaction plate with dNTPs, $MgCl_2$, DNA polymerase, and 10×PCR reaction buffer. Relative quantification ($\Delta C_t$) was performed in triplicate, where mean $\Delta C_t = C_{tFGFR4} - C_{tRNaseP}$, and these values were determined with SDS 2.2 software. Anti-$\log_2$ (mean$\Delta C_t$) represented the absolute FGFR4 copy number. Reactions were performed in triplicate in tumor DNA and duplicate on available genomic DNA. Sequences for CNV primers and probes were: FGFR4 exon 9/10 forward primer TTGTCTGTCTGT-GTGTGTCCATGT (SEQ ID NO: 38), FGFR4 exon 9/10 reverse primer CGTACAGGATGATGTCCGTATACC (SEQ ID NO: 39), FGFR4 exon 9/10 probe CAGAGGAGGAC-CCCACAT (SEQ ID NO: 40), FGFR4 exon 3/4 forward primer TGTGGCATCCGCAGCAT (SEQ ID NO: 41), FGFR4 exon 3/4 reverse primer CTGAGGCAGCCTCCT-GTGTAC (SEQ ID NO: 42), and FGFR4 exon 3/4 probe ATGTGCGGTGTGTTCT (SEQ ID NO: 43). Copy number variation across the entire FGFR4 locus was further analyzed using Agilent comparative genomic hybridization arrays according to the manufacturer's instructions.

Paralogs were identified by protein BLAST search (using sequence NP_998812) and aligned with PRALINE (available on the world wide web at www.ibi.vu.nl). Mutations were queried in dbSNP (National Center for Biotechnology Information), the Human Gene Mutation Database (available on the world wide web at www.hgmd.cf.ac.uk/ac/index.php), and COSMIC (Catalog of Somatic Mutations in Cancer, Sanger Institute). Missense mutations were computationally analyzed for effect on function. FGFR4 TK domain structural models (based upon NP_998812) were generated using SWISS-MODEL (EXAPSY) with hydrogen bonds calculated in DeepView (Swiss protein data bank (Pdb)-Viewer) and predicted conformational changes between wild type and mutants determined with Difference Distance Matrix Plots (DDMP; http://roselab.jhu.edu/ddmp; Richards and Kundrot, Proteins 3:71-84, 1988). Predicted structures and mutation locations were visualized using MBT Protein Workshop (Moreland et al., BMC Bioinformatics 6:21, 2005).

Each FGFR4 missense mutation was computationally analyzed for a predicted effect on protein function using four methods. SIFT (Sorting Intolerant From Tolerant) was used to calculate a SIFT probability score for the likelihood of the mutation to affect protein function (Ng et al., Nucleic Acids Res. 31:3812-3814, 2003). Only one variant had a median sequence information score of <3.25 (FGFR4 I10V). Scores ≦0.05 are predicted to Affect Protein Function (AFP), although approximately 20% of positive SIFT scores represent false positive predictions. PolyPhen (Polymorphism Phenotyping; available on-line at coot.embl.de/PolyPhen) was also used, predicting either unknown (insufficient data for a prediction), benign, possibly, or probably damaging mutations based upon characterization of the substitution site, predicted secondary protein structure, or available three dimensional protein structures (Ramendsky et al., Nucleic Acids Res. 30:3894-3900, 2002; Sunyaev et al., Hum. Mol. Genet. 10:591-597, 2001). The third method employed the profile model of SNPs3D (available on the world wide web at www.snps3d.org) which is based upon conservation at an amino acid position and the probability of observing a variant at that site within the protein's family of homologues (Yue et al., BMC Bioinformatics 7:166, 2006; Yue et al., J. Mol. Biol. 356:1263-1274, 2006). SNPs3D determines a profile score using a Support Vector Machine (SVM), where negative values are associated with deleterious mutations. Approximately, 10% of negative SVM scores are predicted to be false positives. Finally, MAPP (Multivariate Analysis of Protein Polymorphism; Stone and Sidow, Genome Res. 15:978-986, 2005; available on-line at mendel.stanford.edu/SidowLab/downloads/MAPP/MAPP.html) was used to predict the impact of each non-synonymous variant though a comparative analysis of FGFR4 orthologs and the corresponding physicochemical properties specific amino acid changes represent. Alignment and phylogenetic tree building for 9 FGFR4 orthologs (NP_998812_human; XP_001087243_macaque; XP_518127_chimpanzee; NP_032037_mouse; NP_001103374_rat; XP_414474_chicken; XP_001498550_horse; XP_546211_dog; and SP_602166_cow) was performed using standard procedures for ClustalW2 prior to analysis with MAPP. P values <0.05 for a particular amino acid substitution represent those mutations likely to impair protein function.

Results

Figure 1A:
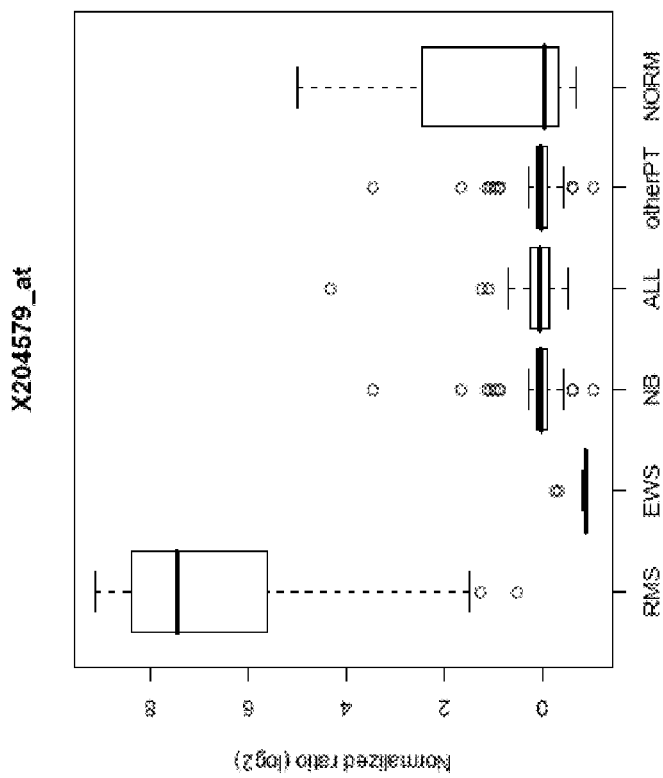
FIG. 1A shows expression of FGFR4 transcripts in a panel of small round blue cell tumors and normal tissues (RMS=rhabdomyosarcoma, EWS=Ewings Sarcoma, NB=neuroblastoma, ALL=acute lymphoblastic leukemia, other PT=other pediatric tumors, and NORM=normal tissue).
Figure 1C:
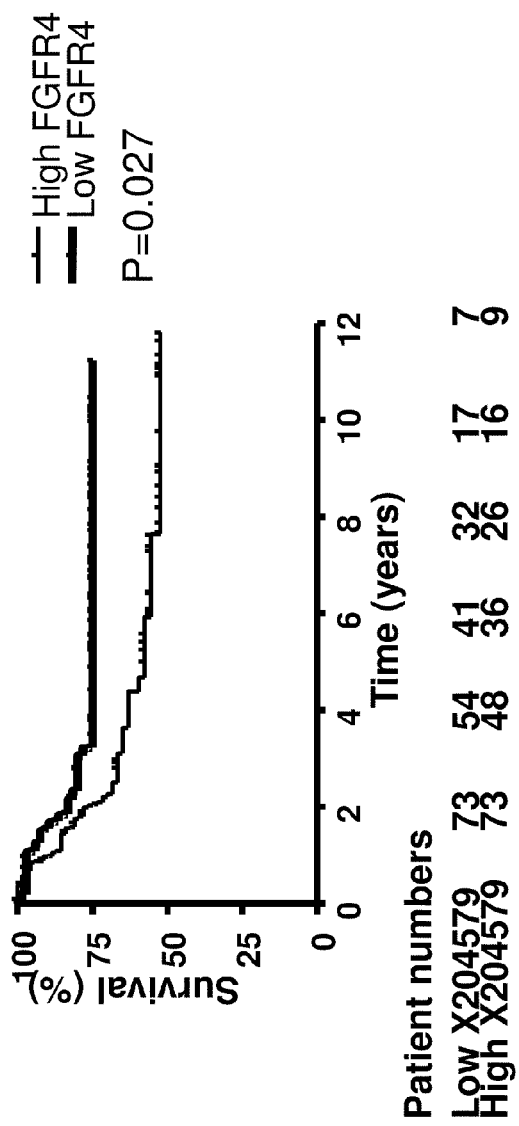
FIG. 1C is a Kaplan-Meier plot showing percent survival of subjects with RMS tumors, grouped based on high or low FGFR4 expression levels.
Figure 1D:
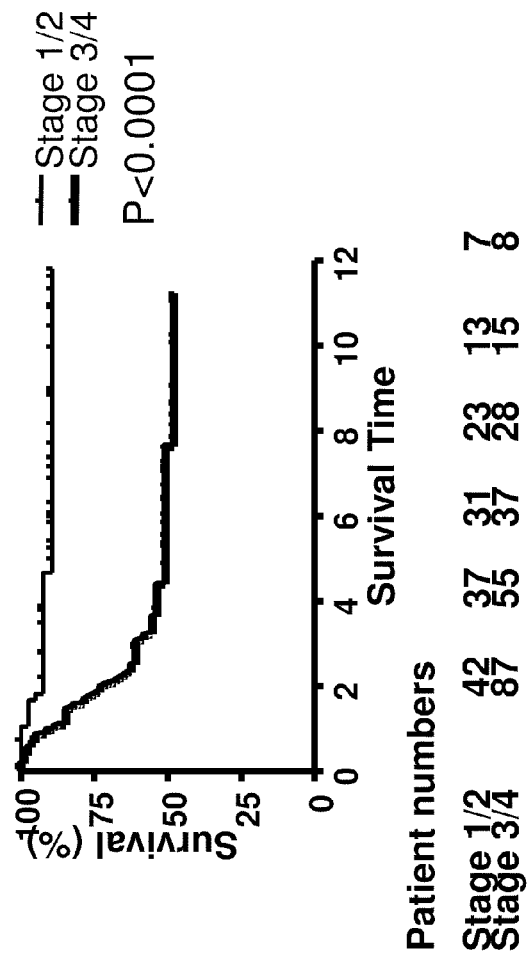
FIG. 1D is a Kaplan-Meier plot showing percent survival of subjects with RMS tumors, grouped based on clinical staging.

RMS gene expression profile was examined using primary and existing expression microarray data sets (Khan et al. Nat. Med. 7:673-679, 2001; Yu et al., Nat. Med. 10:175-181, 2004; Davicioni et al., Cancer Res. 66:6936-6946, 2006). Expression of two FGFR4 transcripts is specific for primary human RMS tumors among a panel of small round blue cell tumors and normal tissues (FIG. 1A, probe X204579_at). The same GeneChip® U133A FGFR4 probe sets also had significantly higher expression in stage 4 metastatic tumors among 149 primary pretreatment RMS gene expression profiles (FIG. 1B). Mortality was significantly higher when these 146 tumors were grouped according to FGFR4 expression (transcript X204579_at; FIG. 1C; Hazard Ratio 1.97; 95% Confidence Interval 1.08-3.48; P=0.027), although the magnitude of this association was not as strong as survival according to clinical staging (FIG. 1D; n=129 with survival data; P<0.0001). Further univariate analysis of this dataset confirmed that high stage and ARMS type were also associated with lower survival (Table 2). However, a Cox proportional hazards multivariate analysis revealed that only clinical stage was associated with early death (Table 2; Hazard Ratio=9.17; P=0.002), indicating a strong association of FGFR4 expression with stage and ARMS histology (FIG. 1E). Finally, examination of existing gene expression profiles from murine RMS cell lines derived from Ink4a/Arf deficient mice revealed significantly higher fgfr4 expression in highly metastatic tumors as compared with low metastatic tumors (P=0.005; FIG. 1F).

TABLE 2

Sub-analyses of FGFR4 Expression in RMS

| Analysis Parameter | Hazard Ratio | 95% Confidence Interval | P value |
|---|---|---|---|
| Univariate | | | |
| STAGE (3 & 4 vs. 1 & 2) | 6.30 | 2.25-17.67 | 0.0005 |
| HISTOLOGY | 2.87 | 1.44-5.72 | 0.003 |
| FGFR4 EXPRESSION | 1.97 | 1.08-3.48 | 0.03 |
| Multivariate | | | |
| STAGE (3 & 4 vs. 1 & 2) | 9.17 | 2.19-38.39 | 0.002 |
| HISTOLOGY | 2.29 | 0.96-5.46 | 0.06 |
| FGFR4 EXPRESSION | 0.94 | 0.43-2.45 | 0.94 |

Figure 2A:
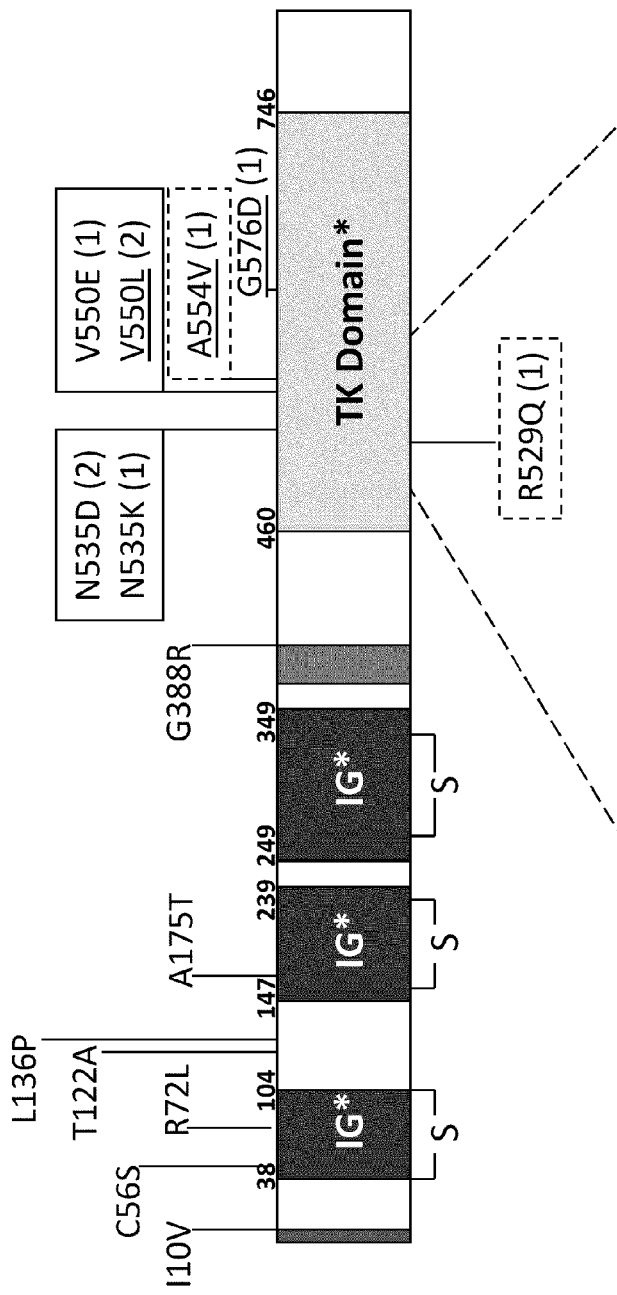
FIG. 2A shows a schematic representation of the FGFR4 protein (top panel) with the sites of amino acid substitutions observed by sequencing 110 RMS tumors and cell lines. Somatic mutations confirmed by sequencing germline host DNA are underlined, and predicted functional mutations are in solid line boxes. Only 1 tyrosine kinase domain mutation was observed among 1030 healthy adult control DNA samples. The bottom panel shows a sequence alignment of a portion of the TK domain from FGFR4 (amino acids 524-559) with the corresponding regions of FGFR1, FGFR2, FGFR3, and Ret. The sites of other mutations in paralogs of FGFR4 are highlighted in dark squares in the TK domain alignment.

FGFR4 protein coding exons and intron/exon borders were initially sequenced from 44 primary tumors. A number of single nucleotide variants were identified (Table 3), of which 10 were only present in a single tumor sample. Fourteen missense variants were identified, of which six were clustered in the TK domain (FIG. 2A). Furthermore, four FGFR4 variants were present at codons 535 and 550 (within the TK domain) in RMS tumors of different histology (FIG. 2A; Table 4). These TK mutations were not present at polymorphic frequencies among 1030 multiethnic controls (Table 3). Two FGFR4 exons corresponding to codons 507 to 607 were sequenced among all tumors and healthy controls with only one previously described variant, R529Q (Greenman et al., Nature 446:153-158), observed among the controls.

TABLE 3

FGFR4 DNA Sequence Variants in RMS Tumors.

| Site | Chromosome 5 Position | AA Change§ | Unpaired Tumor Variant Alleles (88 chrom) | Paired Tumor Variant Alleles (100 chrom)* | Healthy Control Variant Alleles (n = 2060 chrom)‡ |
|---|---|---|---|---|---|
| rs3135918 (C/G) | 176449143 | — | 3 | 3 | ND |

TABLE 3-continued

FGFR4 DNA Sequence Variants in RMS Tumors.

| Site | Chromosome 5 Position | AA Change§ | Unpaired Tumor Variant Alleles (88 chrom) | Paired Tumor Variant Alleles (100 chrom)* | Healthy Control Variant Alleles (n = 2060 chrom)‡ |
|---|---|---|---|---|---|
| rs3135919 (C/T) | 176449146 | — | 0 | 1 | ND |
| rs1122528 (C/T) | 176449148 | — | 1 | 0 | ND |
| none (T/C) | 176449169 | — | 0 | 1 | ND |
| rs1966265 (G/A) | 176449237 | Ile10Val | 19 | 24 | ND |
| rs422421 (T/C) | 176449932 | — | 67 | 62 | ND |
| rs446382 (T/G) | 176450067 | Arg54Arg | 52 | 58 | ND |
| none (G/C) | 176450072 | Cys56Ser | 0 | 2 | ND |
| none (G/T) | 176450120 | Arg72Leu | 0 | 1 | ND |
| none (A/G) | 176450360 | Thr122Ala | 1 | 1 | ND |
| rs376618 (C/T) | 176450403 | Leu136Pro | 70 | 76* | ND |
| none (G/A) | 176450407 | Ser137Ser | 1 | 1 | ND |
| none (G/A) | 176450631 | Ala175Thr | 1 | 0 | ND |
| rs45581232 (G/A) | 176451271 | | 0 | 2 | ND |
| rs3135923 (C/T) | 176451372 | Asn228Asn | 1 | 0 | ND |
| none (G/A) | 176451389 | Arg234His | 0 | 1 | ND |
| rs452885 (C/T) | 176451390 | Arg234Arg | 70 | 77 | ND |
| rs393923 (G/A) | 176451893 | — | 74 | 83 | ND |
| rs45460599 (C/T) | 176451983 | Ala261Ala | 1 | 0 | ND |
| none (C/T) | 176452061 | Ile287Ile | 0 | 1 | ND |
| rs3135925 (A/G) | 176452122 | — | 1 | 0 | ND |
| none (C/G) | 176452330 | Thr332Thr | 0 | 1 | ND |
| none (C/T) | 176452336 | Leu334Leu | 2 | 1 | ND |
| rs351855 (G/A) | 176452849 | Gly388Arg | 35 | 43 | ND |
| rs34284947 (G/A) | 176455003 | Arg529Gln | 0 | 0 | 1 |
| none (A/G) | 176455020 | Asn535Asp | 2 | 0 | 0 |
| none (C/A) | 176455022 | Asn535Lys | 2 | 0 | 0 |
| none (G/C) | 176455157 | Val550Leu | 1 | 1† | 0 |
| none (T/A) | 176455158 | Val550Glu | 1 | 0 | 0 |
| rs351854 (C/T) | 176455168 | Ala553Ala | 2 | 5 | 0 |
| none (C/T) | 176455170 | Ala554Val | 0 | 2† | 0 |
| none (G/A) | 176455236 | Gly576Asp | 0 | 2† | 0 |
| none (A/T) | 176455303 | Arg598Arg | 0 | 1 | 0 |
| rs42409 (C/T) | 176455334 | — | 59 | 70 | ND |
| none (A/T) | 176455361 | — | 1 | 0 | ND |
| rs45523032 (G/A) | 176455792 | — | 1 | 2* | ND |
| rs31777 (C/A) | 176456168 | — | 74 | 80 | ND |
| rs31776 (A/G) | 176456203 | — | 63 | 75* | ND |
| rs168446 (T/G) | 176456404 | — | 0 | 8 | ND |
| none (C/T) | 176457071 | — | 3 | 2 | ND |
| rs873652 (A/T) | 176457599 | — | 0 | 2* | ND |
| none (C/T) | 176457146 | — | 0 | 1 | ND |

ND = not determined
FGFR4 TK catalytic domain exons and intron/exon borders corresponding to codons 507-607 were sequenced in all tumor samples and all controls.
§Amino acid positions are numbered as in SEQ ID NO: 2.
*One tumor sample (RMS205) had loss of heterozygosity at markers rs376618, rs45523032, rs31776, and rs873652.
†Somatic mutations absent in germline genomic DNA.
‡P value = $2.0 \times 10^{-7}$ for TK domain mutations in tumors vs. controls: 7 individuals/94 tumors = 7.4% versus 1 individual/1030 healthy controls = 0.1%.

TABLE 4

FGFR4 Tyrosine Kinase Domain Mutations Observed in RMS Tumors

| Case ID | FGFR4 Codon[§] | Nucleotide (Chr5) | Genotype | Mutation Type | Histology | Pax-FKHR fusion* | CNV[†] | Stage |
|---|---|---|---|---|---|---|---|---|
| RMS06 | N535 | 176455020 | N/D | — | embryonal | Absent | 4.40 | unknown |
| RMS13 | N535 | 176455022 | K/K | — | unknown | Absent | 2.28 | unknown |
| RMS18 | N535 | 176455020 | N/D | — | unknown | Absent | 2.09 | unknown |
| RMS36 | V550 | 176455157 | V/L | — | alveolar | PAX3-FKHR | 6.86 | unknown |
| RMS64 | V550 | 176455158 | V/E | — | embryonal | Absent | 1.69 | III |
| RMS231 | V550 | 176455157 | V/L | somatic | embryonal | Absent | 1.99 | III |
| RMS248 | A554 | 176455170 | V/V | somatic | alveolar | PAX3-FKHR | 1.52 | I |
|  | G576 | 176455236 | D/D | somatic |  |  |  |  |

*Both Pax3-FKHR and Pax7-FKHR fusion transcripts were assayed by RT-PCR
[§]Amino acid positions are numbered as in SEQ ID NO: 2
[†]copy number variation Next, the high prevalence of mutations was validated by sequencing FGFR4 in another 50 tumors with paired genomic DNA (listed in Table 3). In particular, somatic missense mutations in the TK domain were again observed at codon 550 (V550L) in addition to two novel somatic mutations, yielding an overall prevalence of 7.4% (7/94 tumors) for FGFR4 TK domain mutations in unselected RMS samples (FIG. 2; Table 3). The clinical demographics and disease characteristics of both tumor cohorts is presented in Table 5. Two primary tumors with TK domain mutations and available clinical information (n=3, 66%) presented with advanced clinical disease (stage III, Table 4).

TABLE 5

RMS Tumor Clinical Demographics and Disease Characteristics.

|  | Unpaired Tumors N = 44 No. (%) | Paired Tumors N = 50 No. (%) |
|---|---|---|
| Age, years | 8.0 (5.7)[a] | 8.0 (5.7) |
| Sex, male[b] | 13 (25) | 23 (46) |
| Ethnic Group |  |  |
| Caucasian | unknown | 29 (58) |
| African American | unknown | 5 (10) |
| Other or unknown | unknown | 16 (32) |
| Histology |  |  |
| Alveolar | 17 (39) | 19 (38) |
| Embryonal | 19 (43) | 27 (54) |
| Botryoid | 0 (0) | 4 (8) |
| Unknown | 8 (18) | 0 (0%) |
| Stage[c] |  |  |
| I | 7 (16) | 22 (44) |
| II | 6 (14) | 6 (12) |
| III | 11 (25) | 11 (22) |
| IV | 5 (11) | 6 (12) |
| unknown | 15 (34) | 5 (10) |
| Site |  |  |
| Parameningeal | 1 (2) | 1 (2) |
| Orbit | 0 (0) | 3 (6) |
| Other head and neck | 8 (18) | 5 (10) |
| Extremity | 10 (23) | 5 (10) |
| Genitourinary | 7 (16) | 16 (32) |
| Other | 6 (14) | 20 (40) |
| Unknown | 12 (27) | 0 (0) |

Tumor demographics are presented in two groups: n = 44 without paired germline DNA samples and n = 50 that had paired germline DNA samples. Total tumors evaluated was n = 94.
[a]Mean and standard deviation. Number = 23 for unpaired tumors and 50 in paired tumors.
[b]N = 25 for unpaired tumors and N = 50 for paired tumors
[c]Intergroup Rhabdomyosarcoma Study-IV pretreatment staging classification (Raney et al., Sarcoma 5: 9-15, 2001).

Figure 2B:
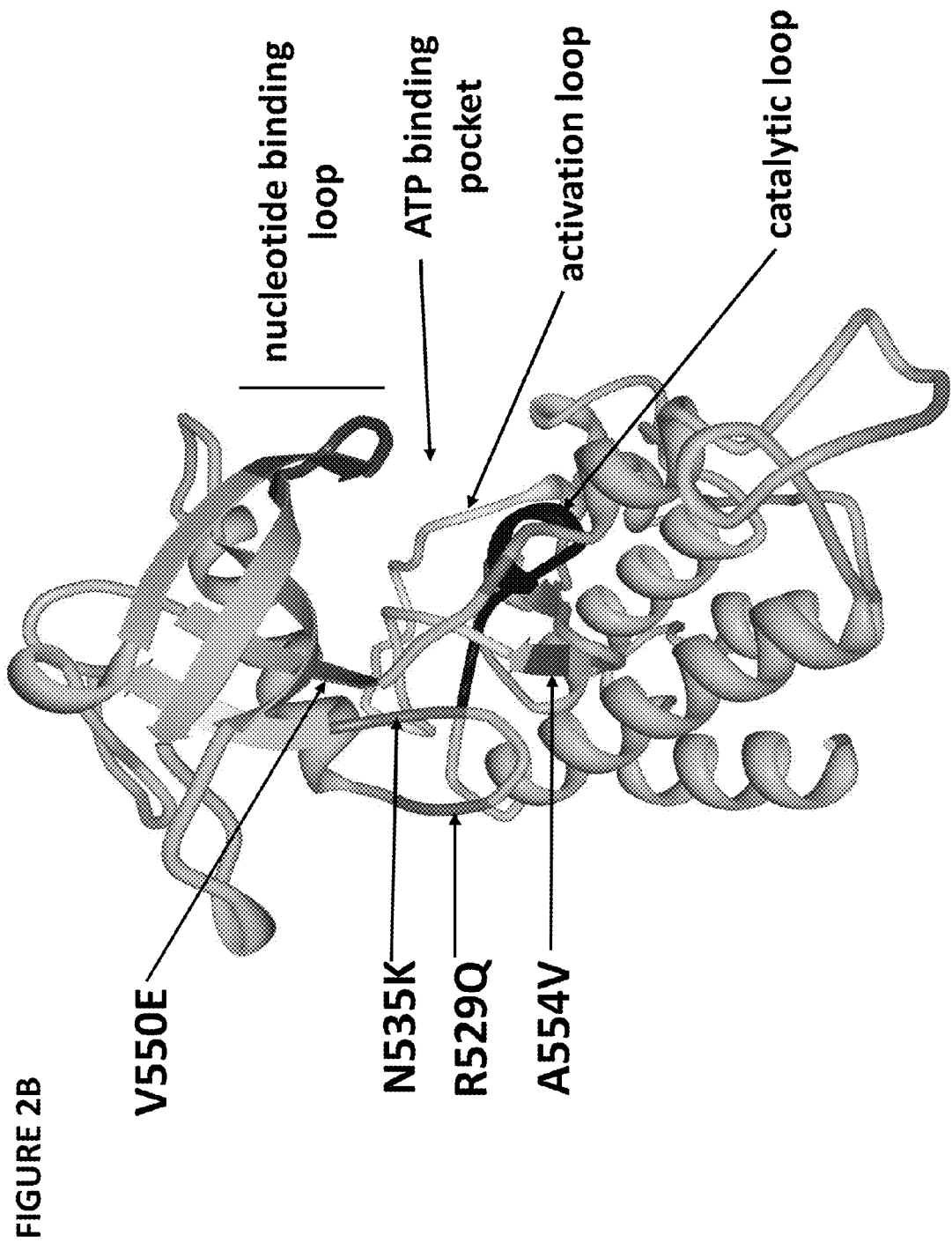
FIG. 2B shows the predicted three-dimensional structure of FGFR4 and the location of tyrosine kinase domain mutations in RMS.
Figure 2C:
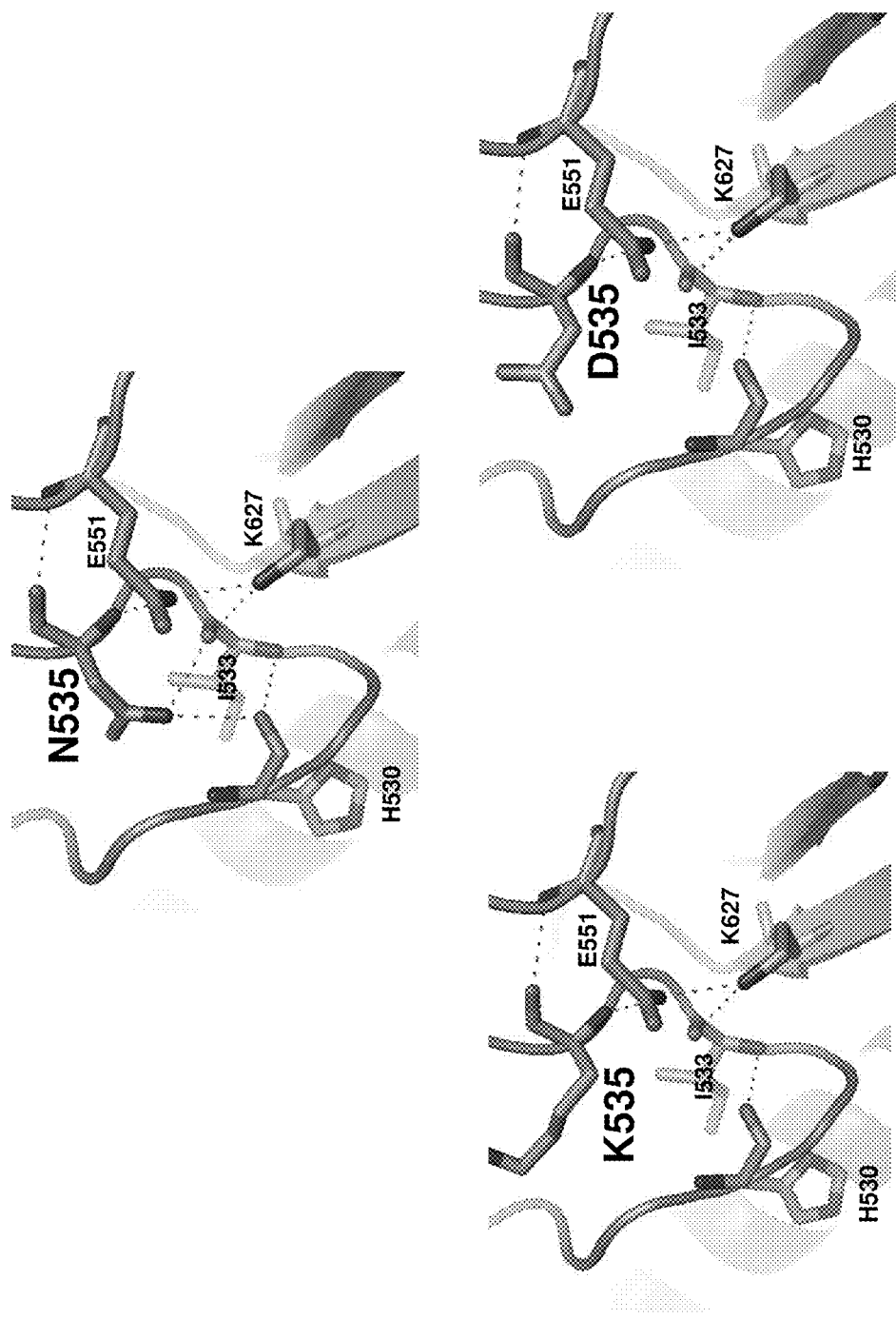
FIG. 2C shows a predictive model of hydrogen bonds within the hinge region of wild type FGFR4 (left), N535K FGFR4 (center), and N535D FGFR4 (right) created using PyMOL (available on the world wide web at pymol.org).

In order to determine the significance of these observations, the FGFR4 TK domain region with the highest prevalence of recurring mutations was aligned with selected paralogs. Paralogous positions to codons 535 and 550 had corresponding disease causing mutations in the other FGFRs and RET (FIG. 2 and Table 6). Multiple predictive analysis methods suggested that only these FGFR4 missense substitutions were likely to result in altered function (Table 7). Modeling of the FGFR4 structure provided a three dimensional validation of these predictions, as the FGFR4 amino acid changes at codons 535 and 550 both map to adjacent sites within the hinge region next to the ATP binding pocket (FIG. 2B) and are predicted to disrupt hydrogen bonds present in the wild type protein. Structurally, these mutations are predicted to result in constitutive FGFR4 phosphorylation. The codon 535 mutations are predicted to eliminate R-group hydrogen bonds in FGFR4 (FIG. 2C) that are known to inhibit receptor autophosphorylation or regulate conformational dynamics during phosphorylation in paralog FGFR2 (Chen et al., *Mol. Cell.* 27:717-730, 2007; Lew et al., *Proc. Natl. Acad. Sci. USA* 104:19802-19807, 2007). The mutations at codon 550 are predicted to alter the ATP binding cleft (Mohammadi et al., *EMBO J.* 17:5896-5904, 1998; Torkamani and Schork, *Cancer Res.* 68:1675-1682, 2008).

TABLE 6

Spectrum of Tyrosine Kinase Domain Mutations in FGFR4 and Paralogs

| Gene | Mutation[§] | Disease | Germline |
|---|---|---|---|
| FGFR4 | N535K | RMS | unknown |
|  | N535D | RMS | unknown |
|  | V550E | RMS | unknown |
|  | V550L | RMS | no |
|  | V550M | BC | no |
|  | A554V/G576D | RMS | no |
| FGFR1 | N546K | GBM | no |
| FGFR2 | I547V | EC | no |
|  | N549H | CS/PS | yes |
|  | N549K | EC | no |
|  | E565G | PS | yes |
|  | E565A | PS | yes |
| FGFR3 | N540K | HC | yes |
|  | N540S | HC | yes |
|  | N540T | HC | yes |

TABLE 6-continued

Spectrum of Tyrosine Kinase Domain Mutations in FGFR4 and Paralogs

| Gene | Mutation§ | Disease | Germline |
|---|---|---|---|
| RET | L790P | MTC | yes |
|  | Y791P | MTC | yes |
|  | V804L | MTC | yes |

§Amino acid positions are numbered as in SEQ ID NO: 2
RMS = rhabdomyosarcoma;
BC = breast cancer;
GBM = glioblastoma multiforme;
EC = endometrial carcinoma;
CS = Crouzon syndrome;
PS = Pfieffer syndrome;
HC = hypochondroplasia;
MTC = medullary thyroid carcinoma.

TABLE 7

Computational Analysis Predicting Functional FGFR4 Missense Mutations.

| Functional Domain | Missense Mutation§ | SIFT | Polyphen | SNPs3D SVM profile | MAPP P value |
|---|---|---|---|---|---|
| Signal peptide | I10V‡ | T (1.00) | Unknown | — | 0.83 |
| Extra-cellular | C56S‡ | T (0.46) | Benign | 1.91 | 0.002 |
| Extra-cellular | R72L‡ | T (0.32) | Possibly | 0.72 | 0.0003 |
| Extra-cellular | T122A‡ | T (0.41) | Benign | 0.91 | 0.001 |
| Extra-cellular | L136P‡ | T (0.32) | Benign | 1.28 | 0.92 |
| Ig like domain 2* | A175T‡ | T (0.70) | Benign | 2.98 | 0.00001 |
| Transmembrane domain | G388R‡ | T (0.15) | Possibly | −0.22 | 0.000001 |
| Tyrosine kinase domain* | R529Q† | APF (0.00) | Benign | 0.15 | 0.006 |
| Tyrosine kinase domain* | N535D‡ | APF (0.00) | Probably | −2.67 | 0.00003 |
| Tyrosine kinase domain* | N535K‡ | APF (0.00) | Probably | −0.61 | 0.00006 |
| Tyrosine kinase domain* | V550E‡ | APF (0.00) | Probably | −3.02 | 0.00001 |
| Tyrosine kinase domain* | V550L‡ | APF (0.00) | Possibly | −0.95 | 0.0002 |
| Tyrosine kinase domain* | A554V‡ | APF (0.03) | Benign | −0.84 | 0.000008 |
| Tyrosine kinase domain* | G576D‡ | T (0.62) | Benign | 2.06 | 0.00001 |

Figure 3:
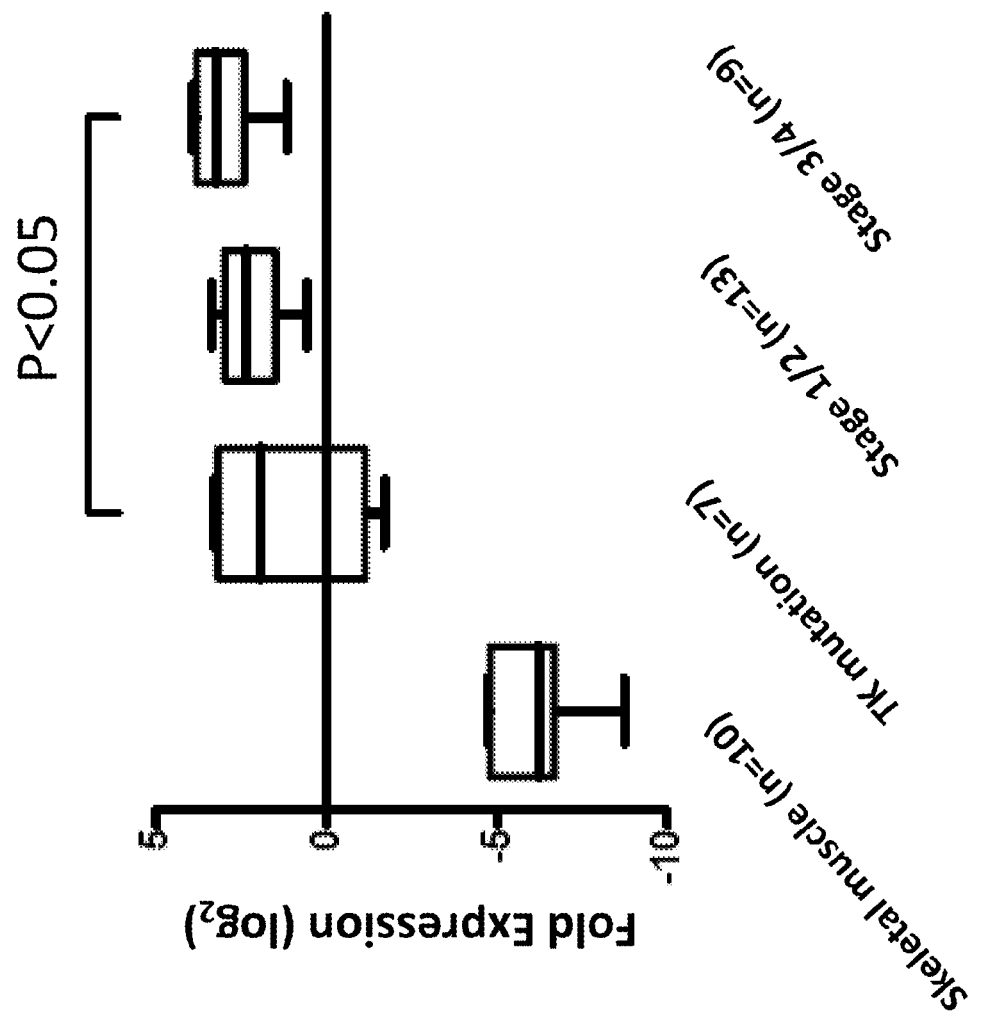
FIG. 3 shows expression of FGFR4 determined by quantitative real time PCR, grouped by presence of a tyrosine kinase domain mutation (TK mutation) or by tumor stage. Skeletal muscle was used as a normal control.

§Amino acid positions are numbered as in SEQ ID NO: 2
Abbreviations:
SIFT = Sorting Intolerant From Tolerant;
PolyPhen = Polymorphism Phenotyping;
SNPs3D;
MAPP = Multivariate Analysis of Protein Polymorphism;
SIFT: T = tolerated,
AFP = Affect protein function, and the value in parentheses is the SIFT probability score.
Results for each method predicted to alter protein function are in bold.
*Domains as defined by the results of a search of the NCBI Conserved Domain database (NCBI CD-Search).
†One FGFR4 missense mutation was detected in genomic DNA of one healthy control from the population panels (R529Q).
‡Missense mutations detected in genomic DNA extracted from rhabdomyosarcoma tumor samples Previous studies have suggested that mutations of oncogenes are associated with either amplification and/or increased expression. Of the 94 tumors evaluated, 18 (19.1%) had FGFR4 copy number ≧2.5, 74 (78.7%) had FGFR4 copy number ≧1.5 to <2.5, and 2 (2.1%) had FGFR4 copy number <1.5. There was no significant association between FGFR4 copy number and TK domain mutational status, however two of seven tumors had >2.5 copies (Table 4). Of interest, tumors harboring the TK domain mutations had significantly lower FGFR4 mRNA expression compared to nine stage 3/4 metastatic tumors (P<0.05; FIG. 3).

Example 2

In Vitro Characterization of FGFR4 Mutations

This example describes the in vitro characterization of FGFR4 mutations identified in RMS samples.

Methods

FGFR4 knock-in experiments were performed to examine the significance of the RMS FGFR4 TK domain mutations. Full length human FGFR4 (Clone ID 4121396) was subcloned in pOTB7 vector (Invitrogen, Carlsbad, Calif.) and then subcloned into the XhoI site of pMSCVpuro vector (Clontech Laboratories, Mountain View, Calif.). The poly-A tail was removed by restriction digestion and vector relegation after site directed mutagenesis created a restriction enzyme recognition site. N535K or V550E mutations were introduced into the FGFR4 gene in the vector by site directed mutagenesis. Wild type and mutated FGFR4 clones in pMSCVpuro were confirmed by sequencing. PT67 cell line (Clontech Laboratories, Mountain View, Calif.) was used to pack the retrovirus. Retroviruses carrying wild type FGFR4, FGFR4 N535K, or FGFR4 V550E were used to transfect murine RMS cell lines RMS119 and RMS772, which were previously derived from spontaneous tumors in an HGF/SF-transgenic, Ink4a/Arf-deficient RMS mouse model (Yu et al., Nature Med. 10:175-181, 2004; Yu et al., Cancer Res. 62:2951-2956, 2002). In some cases, pMSCVzeo retroviral vector expressing firefly luciferase was later transduced into the RMS772 cell lines. Real time PCR (Applied Biosystems, Foster City, Calif.) and Western blot (anti-rabbit antibody, catalog no. sc-124 Santa Cruz Biotechnology, Inc., Santa Cruz, Calif.) was used to verify the expression of FGFR4 mRNA and protein level respectively.

RMS772 and RMS119 cells were cultured in RPMI1640 (Quality Biological Inc., Gaithersburg, Md.) supplemented with 2 mM L-Glutamine (Quality Biological Inc.), 1% penicillin/streptomycin (Quality Biological Inc.), and 0-10% FBS (Hyclone, Logan, Utah). NIH3T3 and PT67 cell lines were grown in DMEM (Quality Biological Inc.) supplemented with 10% FBS, 2 mM L-Glutamine and 1% penicillin/streptomycin.

Growth of RMS119 and RMS772 transfectants was characterized. Briefly, cells were seeded in 96 well plates in culture medium containing 10% fetal bovine serum (FBS). About 16 hours later, culture medium was removed, cells were washed with 0% FBS culture medium 2 times, and 0%, 0.1%, 1%, or 10% FBS culture medium was added. Cells were counted every 24 hours for 72 hours. Invasion assays were performed according to the manufacturer's recommendations in Cultrex 96 well Boyden chambers with 8 micron transmembrane pores (Corning, Lowell, Mass.), a 0.5× basement membrane extract, and a serum gradient of 0.5 to 1% (Trevigen, Gaithersburg, Md.). Plates were read 24 hours after cell seeding.

Immunoblotting was performed on cells cultured in 10% FBS and lysed in RIPA buffer supplemented with 1% protease inhibitor (Pierce Biotechnology, Rockford, Ill.) and 1% phosphatase inhibitor (Pierce Biotechnology). FGFR4 autophosphorylation immunoblots were performed after FGFR4 immunoprecipitation (FGFR-4 (C-16) antibody; Cat. No. sc-124; Santa Cruz Biotechnology, Santa Cruz, Calif.) with protein A/G agarose beads. Twenty micrograms of proteins were separated on 4-12% Bis-Tris gels (Invitrogen) and transferred to nitrocellulose membrane by iBlot (Invitrogen). For FGFR4 phosphorylation immunoblots, membranes were blocked with 5% non-fat dry milk in PBS and 0.1% Tween-20 (PBST) and were probed with antibodies to anti-phosphotyrosine (clone 4G10; Millipore, Billerica, Mass.) and human FGFR-4 (C-16; Santa Cruz Biotechnology). For pathway analyses, membranes were blocked with 5% non-fat dry milk in TBS and 0.1% Tween-20 (TBST) and were probed with the following antibodies: Akt (all antibodies from Cell Signaling, Danvers, Mass. unless otherwise specified), p-Akt (Ser473), p-Gsk3β, p-mTor, S6K, p-S6K, 4Ebp1, p-4Ebp1, Erk 1/2, p-Erk 1/2, Stat3, p-Stat3, and Gapdh (Chemicon International, Danvers, Mass.). Specific molecules were detected with HRP-conjugated anti-mouse or anti-rabbit secondary antibodies (Pierce Biotechnology/Thermo Fisher Scientific, Rockford, Ill.) and enhanced with SuperSignal Chemiluminescence kits (Pierce Biotechnology). Signal was detected on Kodak Biomax MR X-ray film (Kodak, Rochester, N.Y.).

RMS772 cells for microarray experiments were cultured as described in 0% FBS prior to RNA extraction. Gene expression profiling was performed using mouse genome 430 2.0 Array (Affymetrix) and expression data were normalized with DNA Chip Analyzer (dChip) in the PM-only model. The effect of the FGFR4 mutants on murine RMS cells was determined on the basis of gene set enrichment analysis (GSEA; available on the world wide web at www.broad.mit.edu/gsea), where expression data for K535 and E550 cells were combined and compared to the vector control (Subramanian et al., *Proc. Natl. Acad. Sci. USA* 102:15545-15550, 2005). The gene sets with a false discovery rate (FDR) of <0.01 were considered significant.

Results

Figure 4A:
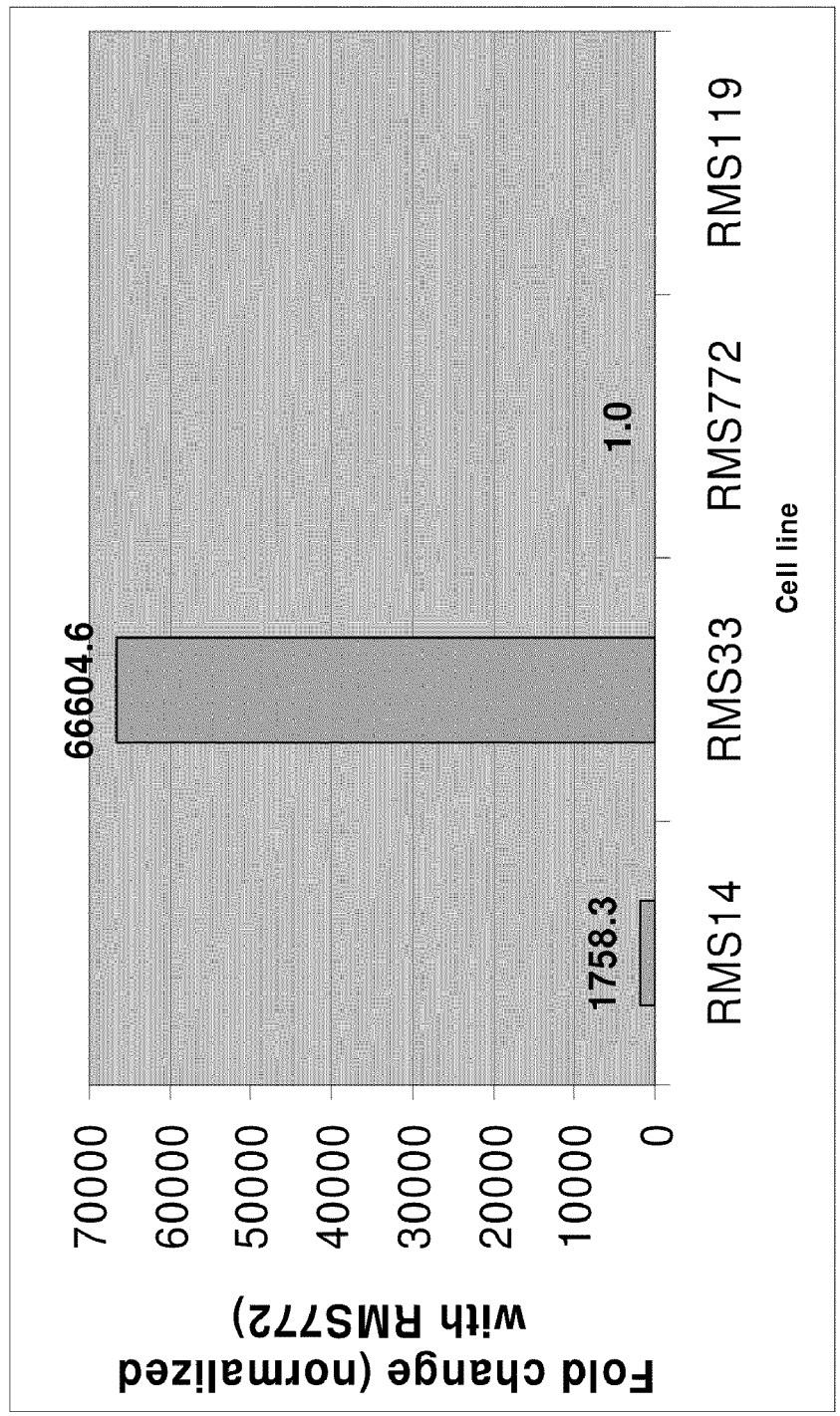
FIG. 4A shows mRNA expression of mouse FGFR4 in RMS tumor cell lines derived from Ink4a/Arf deficient mouse RMS model determined by quantitative RT-PCR.

To examine the significance of the RMS FGFR4 TK domain mutations, murine RMS cell lines RMS119 and RMS772, which were previously derived from spontaneous tumors in an HGF/SF-transgenic, Ink4a/Arf-deficient RMS mouse model (Yu et al., *Nature Med.* 10: 175-181, 2004; Yu et al., *Cancer Res.* 62:2951-2956, 2002) were used. These cell lines were chosen based upon their prior characterization for a low propensity for metastasis and significantly lower murine Fgfr4 expression compared to highly metastatic murine RMS cell lines RMS14 and RMS33 (FIG. 4A).

Figure 4B:
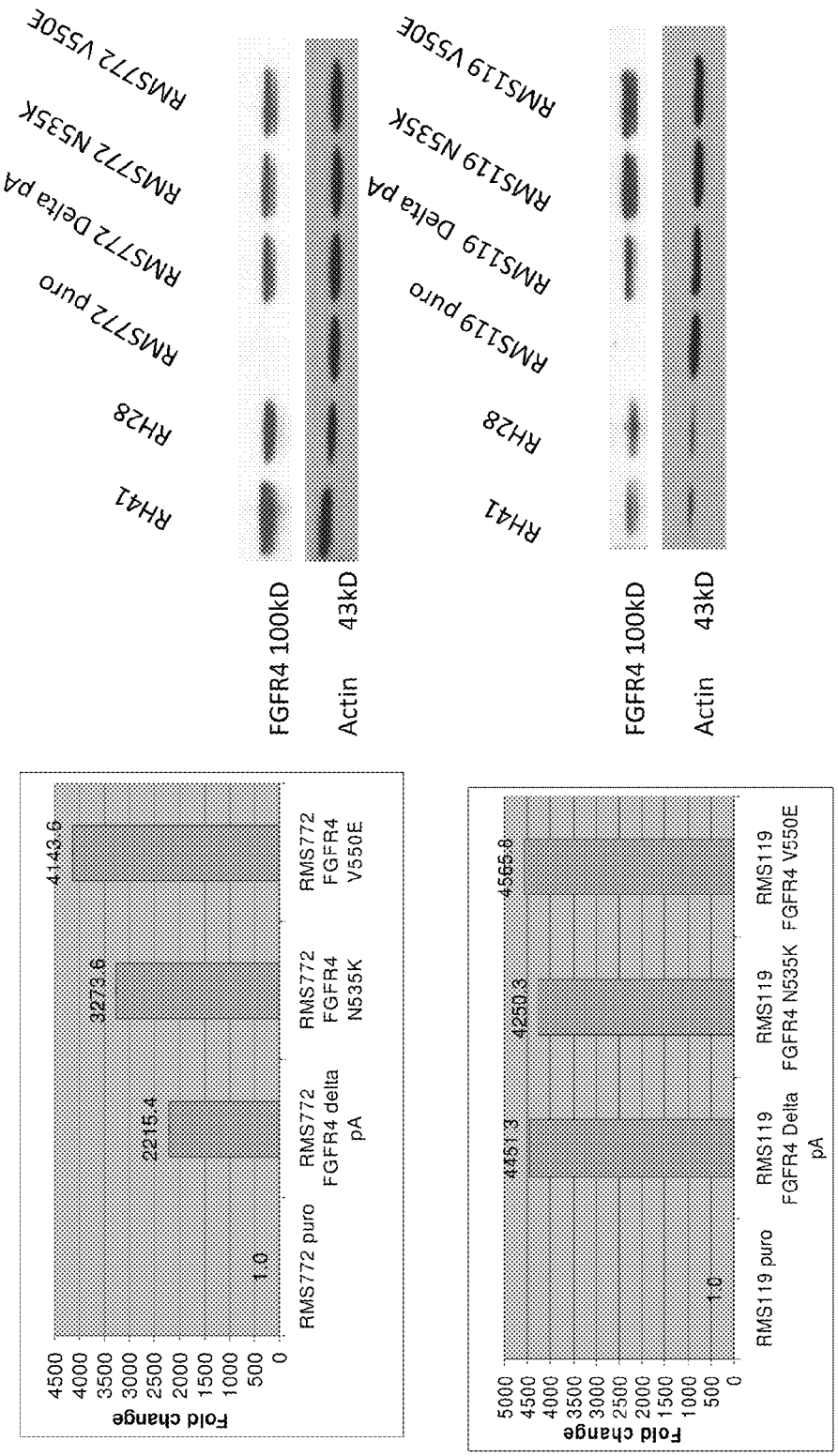
FIG. 4B shows expression of human wild type FGFR4 and FGFR4 TK domain mutants in mouse RMS772 (top panel) and RMS119 (bottom panel) cell lines stably expressing these same human FGFR4 proteins. mRNA expression was determined by RT-PCR (left) and protein expression was determined by Western blot (right). Delta pA=wild type human FGFR4. Puro=vector control. RH41 and RH28 are human RMS cell lines.
Figure 4C:
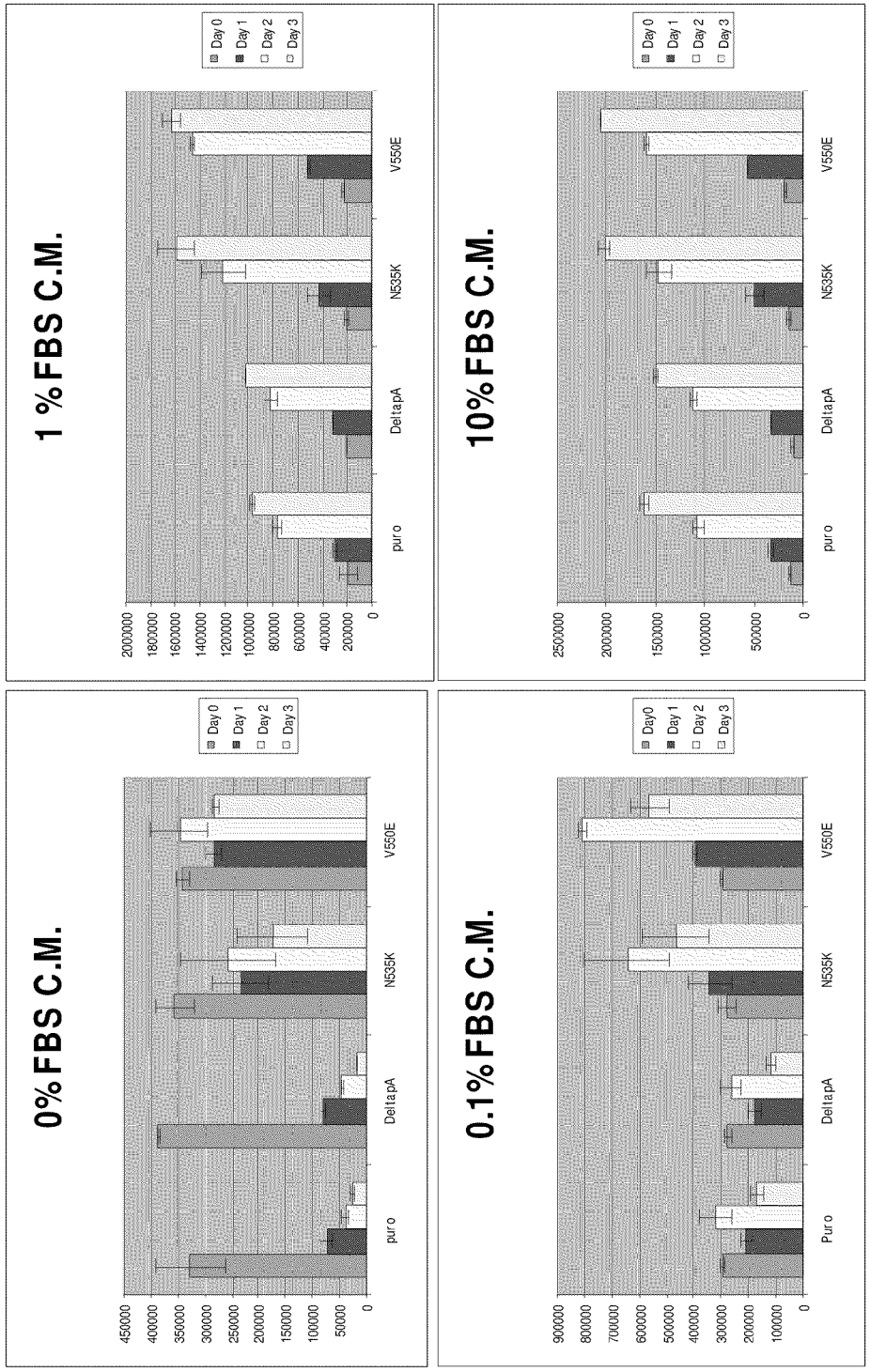
FIG. 4C shows growth of RMS772 cells expressing vector only (Puro) wild type human FGFR4 (Delta pA), FGFR4 N535K, or V550E mutants cultured with varying amounts of fetal bovine serum.
Figure 4D:
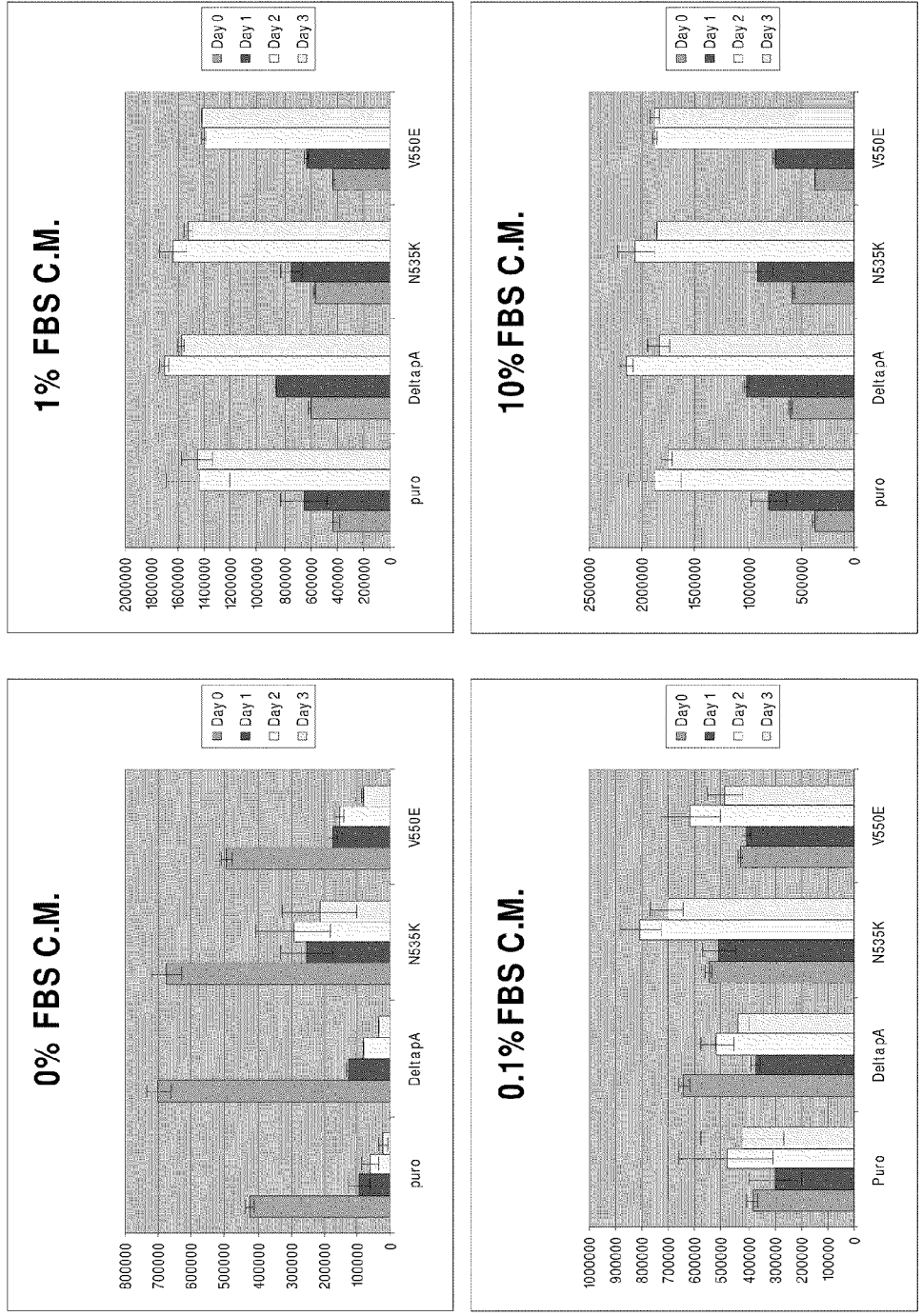
FIG. 4D shows growth of RMS119 cells expressing vector only (Puro) wild type human FGFR4 (Delta pA), FGFR4 N535K, or V550E mutants cultured with varying amounts of fetal bovine serum.

Wild type human FGFR4, FGFR4 N535K or FGFR4 V550E were stably transfected into RMS119 and RMS772 cell lines which were confirmed by real time PCR and Western blot (FIG. 4B). Introduction of the two mutant forms of FGFR4 into RMS119 and RMS772 resulted in significantly less sensitivity to the effect of serum starvation (FIGS. 4C and 4D). However, this difference in cell growth was either absent (RMS119) or less pronounced (RMS772) under standard conditions in 10% serum (FIGS. 4C and 4D).

The effect of activating human FGFR4 mutations N535K and V550E on signal transduction pathways was examined. Both of these mutations resulted in significant auto-phosphorylation of the FGFR4 receptor in RMS772 cells (FIG. 5A). Western blot analysis of known FGFR downstream signaling molecules found significant differences in the Stat, Akt, and Map kinase/Erk pathways, with higher total Stat3 and phospho-Stat3 in both mutant lines (FIG. 5B). Of note, the mutant cell lines also had a decrease in phosphorylated Akt, and a discernible difference in the Map kinase pathway with decreased phospho-Erk1/2 in both wild type FGFR4 and mutant transductants compared to the vector control (FIG. 5B). Other signaling molecules including mTor, S6K, 4Ebp1 and Gsk3β showed no significant differences between transductants (FIG. 5C).

Figures 6A, 6B:
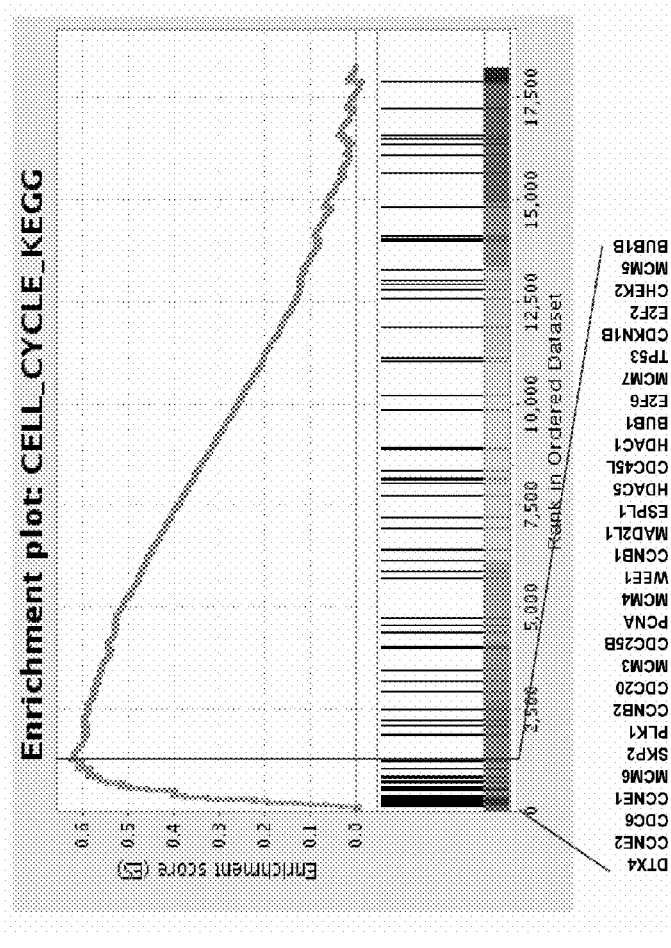
FIG. 6A is a gene enrichment plot showing up-regulation of cell cycle and DNA replication gene pathways in cells expressing FGFR4 N535K or V550E mutants.
FIG. 6B shows cell pathways that are up-regulated or down-regulated in cells expressing FGFR4 N535K or V550E mutants.

Global downstream effects of these mutants in RMS772 cells were examined using gene expression profiling. Gene set enrichment analysis showed that mutant cell lines had significant up-regulation of cell cycle and DNA replication gene pathways (FDR<0.01), while striated muscle and cell adhesion pathways were diminished (FIGS. 6A and 6B).

Example 3

Proliferation, Invasion, and Metastatic Potential of FGFR4 Mutants

This example shows the proliferation, invasion, and metastatic potential characteristics of FGFR4 TK domain mutants.

Methods

All animal studies utilized 8-10 week old, male NU/NU-Foxn1$^{nu}$ nude mice (Charles River Laboratories, Fredrick, Md.) housed in a pathogen free environment. Animal care and experimental procedures were approved by the National Institute of Health Animal Care and Use Committee. In vivo tumor growth was assessed using RMS772 transductants or NIH3T3 transductants with $1 \times 10^6$ cells (0.1 milliliters) subcutaneously injected into the right flank of each mouse. Mice were monitored every other day and tumor dimensions were measured by caliper. Tumor volume was determined by the formula: (long axis×short axis$^2$)/2.

For experimental metastasis assays and survival analysis, $1 \times 10^6$ RMS772 cells or $1 \times 10^5$ NIH3T3 cells, either expressing or not expressing luciferase, were intravenously injected into tail veins of nude mice as previously described (Yu et al., *Nature Med.* 10: 175-181, 2004). Cells fluorescently labeled with CMFDA (Invitrogen) were assayed for early metastasis by intravital videomicroscopy (IVVM) as previously described at 1, 4, and 24 hours after tail vein injection (Khanna et al., *Nature Med.* 10:182-186, 2004). Gross tumor number in lung tissue was assessed by observation at necroscopy 21 days for an endpoint metastasis assay. For survival analysis, mice were imaged twice weekly with a Xenogen IVIS 100 imaging system until the protocol end-point when the mice appeared weak and sick.

Results

Figure 7A:
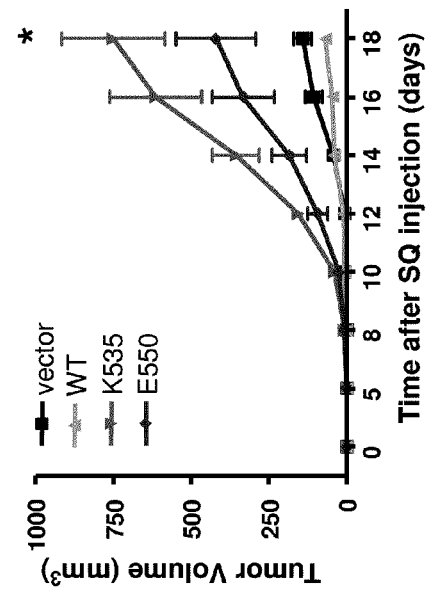
FIG. 7A shows cell number in RMS772 cells expressing vector only, wild type FGFR4 (WT), FGFR4 N535K (K535), or FGFR4 V550E (E550).
Figure 7C:
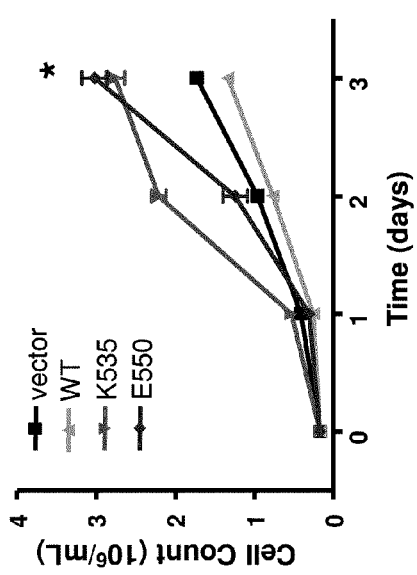
FIG. 7C shows invasiveness of RMS772 cells expressing vector only, wild type FGFR4 (WT), FGFR4 N535K (K535), or FGFR4 V550E (E550) in a Boyden chamber invasiveness assay (normalized to vector control).
Figure 7B:
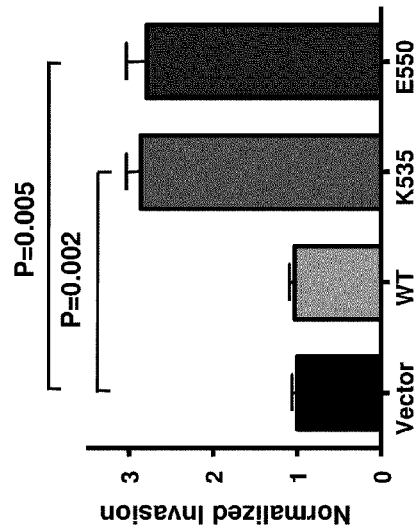
FIG. 7B shows tumor volume in nude mice following subcutaneous injection of RMS772 cells expressing vector only, wild type FGFR4 (WT), FGFR4 N535K (K535), or FGFR4 V550E (E550).

Both the K535 and E550 mutations caused significantly higher growth rates in RMS772 cell lines grown in vitro when compared to wild type FGFR4 at 72 hours (P values=0.0071 and 0.0090, respectively, FIG. 7A). Consistent with these data, subcutaneous injection of the RMS772 transductants into nude mice demonstrated rapid increases in tumor volume for K535 and E550 (both P=0.0079 at 18 days; FIG. 7B) providing evidence for increased in vivo growth. Using a modified Boyden chamber invasion assay, 3-fold enhanced invasiveness associated with FGFR4 mutant cell lines compared to the vector control or wild type FGFR4 in RMS772 was observed (P=0.002 for vector versus K535, P=0.005 for E550; FIG. 7C).

Figure 7F:
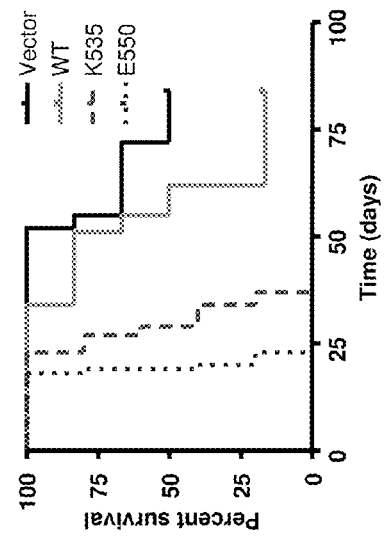
FIG. 7F shows the number of gross lung metastases observed in nude mice three weeks after intravenous injection of RMS772 cells expressing vector only, wild type FGFR4 (WT), FGFR4 N535K (K535), or FGFR4 V550E (E550).
Figure 7G:
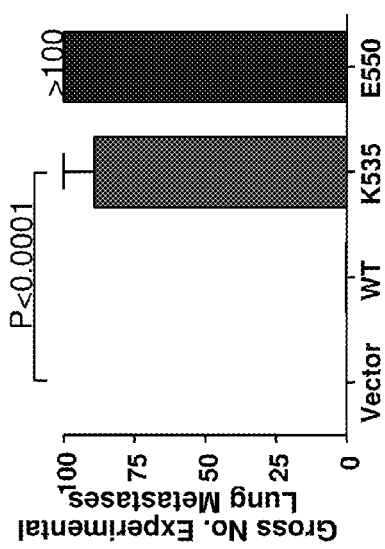
FIG. 7G is a Kaplan-Meier plot showing survival of nude mice injected with RMS772 cells expressing vector only, wild type FGFR4 (WT), FGFR4 N535K (K535), or FGFR4 V550E (E550).
Figure 7H:
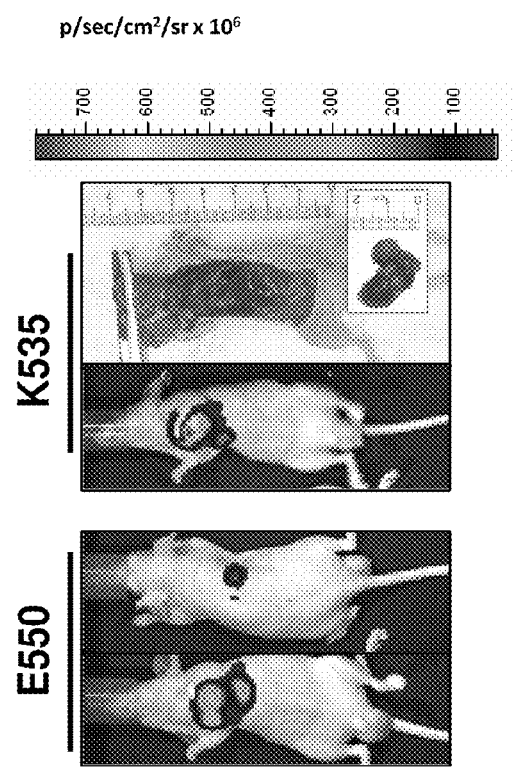
FIG. 7H is in vivo bioluminescent images and necroscopy from mice injected with RMS772 cells expressing FGFR4 V550E (showing pulmonary metastases, left panel) or RMS772 cells expressing FGFR4 N535K, showing pulmonary metastases (right panel).

Cellular arrest in the lungs and early metastasis was assayed by intravital video microscopy (IVVM) in mice after intravenous injection of fluorescently labeled RMS772 transductants. IVVM at 1 hour post injection demonstrated the presence of all 4 transductants, however, only mutant lines demonstrated persistent foci in the lungs after 24 hours (FIGS. 7D and 7E). To determine whether these differences in growth and invasion influence in vivo metastatic potential, RMS772 cells expressing wild type human FGFR4 or mutations were introduced into nude mice intravenously in a separate experiment. At three weeks, mutant cell lines produced significantly more gross pulmonary metastases compared to those expressing wild type FGFR4 (FIG. 7F). Kaplan Meier analysis demonstrated earlier mortality for mice injected with mutant cell lines (P for trend <0.0001 by Logrank test; E550 median survival=19 days; K535=29 days; wild type=59 days; and vector control=78 days) due to metastatic disease (FIGS. 7G and 7H).

Figure 8C:
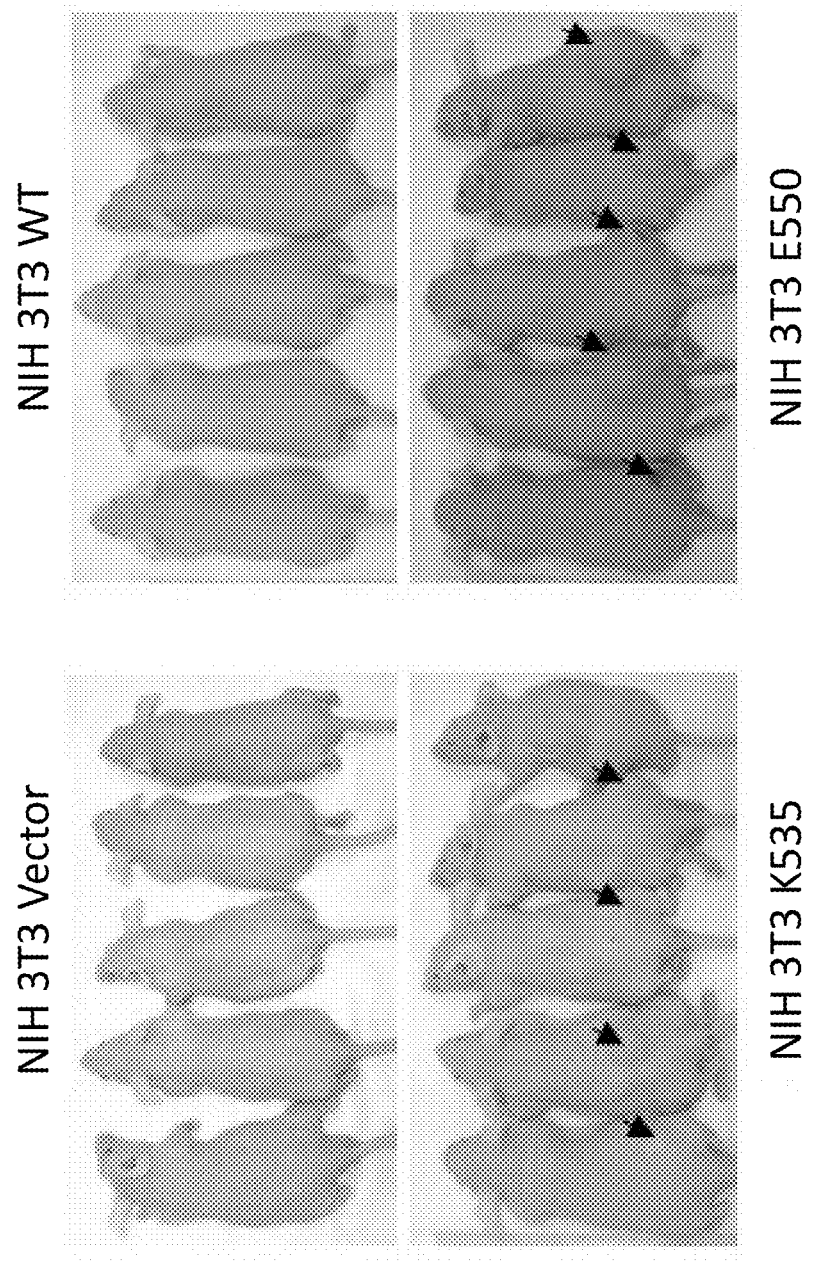
FIG. 8C is a series of photographs of nude mice 18 days following subcutaneous injection of NIH3T3 cells expressing vector only, wild type FGFR4 (WT), FGFR4 N535K (K535), or FGFR4 V550E (E550). N535K supported in vivo growth in 4 of 5 mice and V550E supported in vivo growth in 5 of 5 mice, while vector only or wild type FGFR4 expressing cells did not grow subcutaneously in vivo.

To independently validate these results, NIH 3T3 cells were transduced with the same constructs and the in vivo subcutaneous growth and intravenous experimental metastasis assays were repeated. Rapid growth was observed in mice receiving subcutaneous NIH 3T3 cells transduced with FGFR4 K535 or E550 compared to no growth among the controls (FIGS. 8A and 8B). Intravenous injection of 3T3 cell lines similarly resulted in earlier mortality due to metastatic disease in animals receiving mutant FGFR4 cells (FIG. 8C).

Example 4

Effect of FGFR4 Inhibitors on RMS Cells

This example shows the effect of FGFR4 inhibitors on RMS cell lines expressing human wild type or mutant FGFR4 proteins.

Methods

The effect of PD17304 in RMS119 and RMS772 transfectants was determined using cell cycle assays. Briefly cells were first treated with PD173074 at a final concentration of 5 uM for 24 hours. Cells were then pulsed with BrdU for 40 minutes, and then fixed, permeabilized, and treated with DNase, and followed by staining with mAb (BD Biosciences, Franklin Lakes, N.J.) against BrdU and with 7-AAD (BD Biosciences, Franklin Lakes, N.J.) respectively. Flow cytometry was used to analyze the cell cycle parameters.

RT-CES® (ACEA Biosciences, San Diego, Calif.) was used to determine the $IC_{50}$ of PD173074 or imatinib in various human RMS cell lines. Briefly human RMS cell lines were seeded in the 96 well plate device at 5000-20,000 cells per well. After 16 hours, PD173074 or imatinib was added so that the final concentration ranged from 1 µM to 40 µM. Cell growth was monitored and $IC_{50}$ values were calculated by Cell Office® (ACEA Biosciences, San Diego, Calif.).

Results

The effect of the FGFR inhibitor PD173074 on RMS cells expressing FGFR4 TK domain inhibitors was tested. PD173074 binds to the ATP binding pocket of FGFRs and inhibits receptor phosphorylation (see e.g. Mohammadi et al., *EMBO J.* 17:5896-5904, 1998).

Figure 9A:
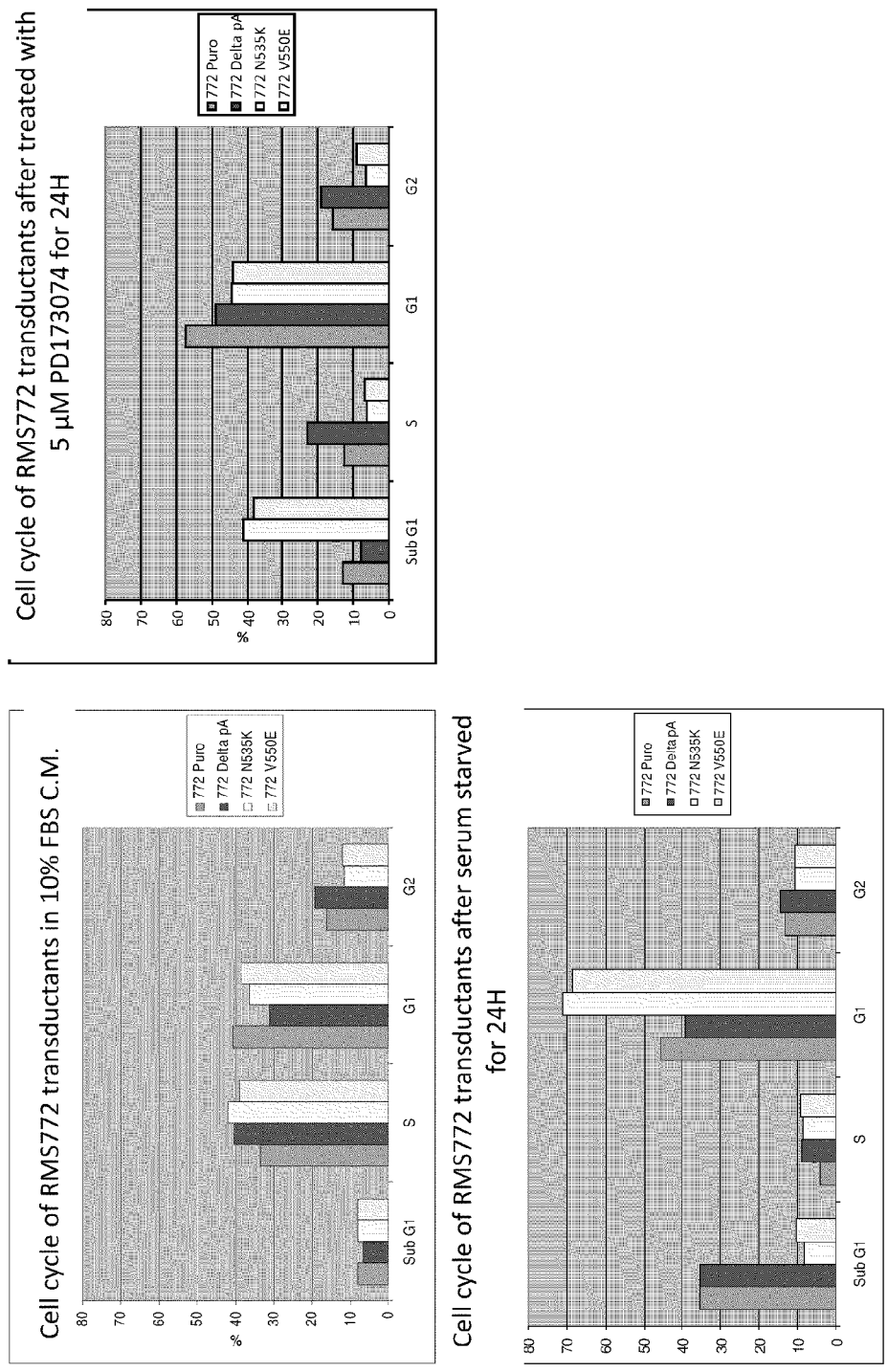
FIG. 9A shows the percentage of cells in each stage of the cell cycle of mouse RMS772 cells expressing vector only (puro), wild type (Delta pA), or mutant human FGFR4 cultured with varying amounts of fetal bovine serum or in the presence of PD173074 for 24 hours.

Apoptosis was assessed by determining the fraction of cells in the subG1 stage of the cell cycle. There were no differences in cell cycle parameters of RMS772 cells expressing TK domain mutants cultured in medium containing 10% FBS compared to vector or wild type FGFR4 (FIG. 9A). However, both vector and wild type controls had significantly higher proportions of apoptotic cells under conditions of serum starvation compared to mutant cell lines as demonstrated by an increased SubG1 fraction (FIG. 9A).

Figure 9B:
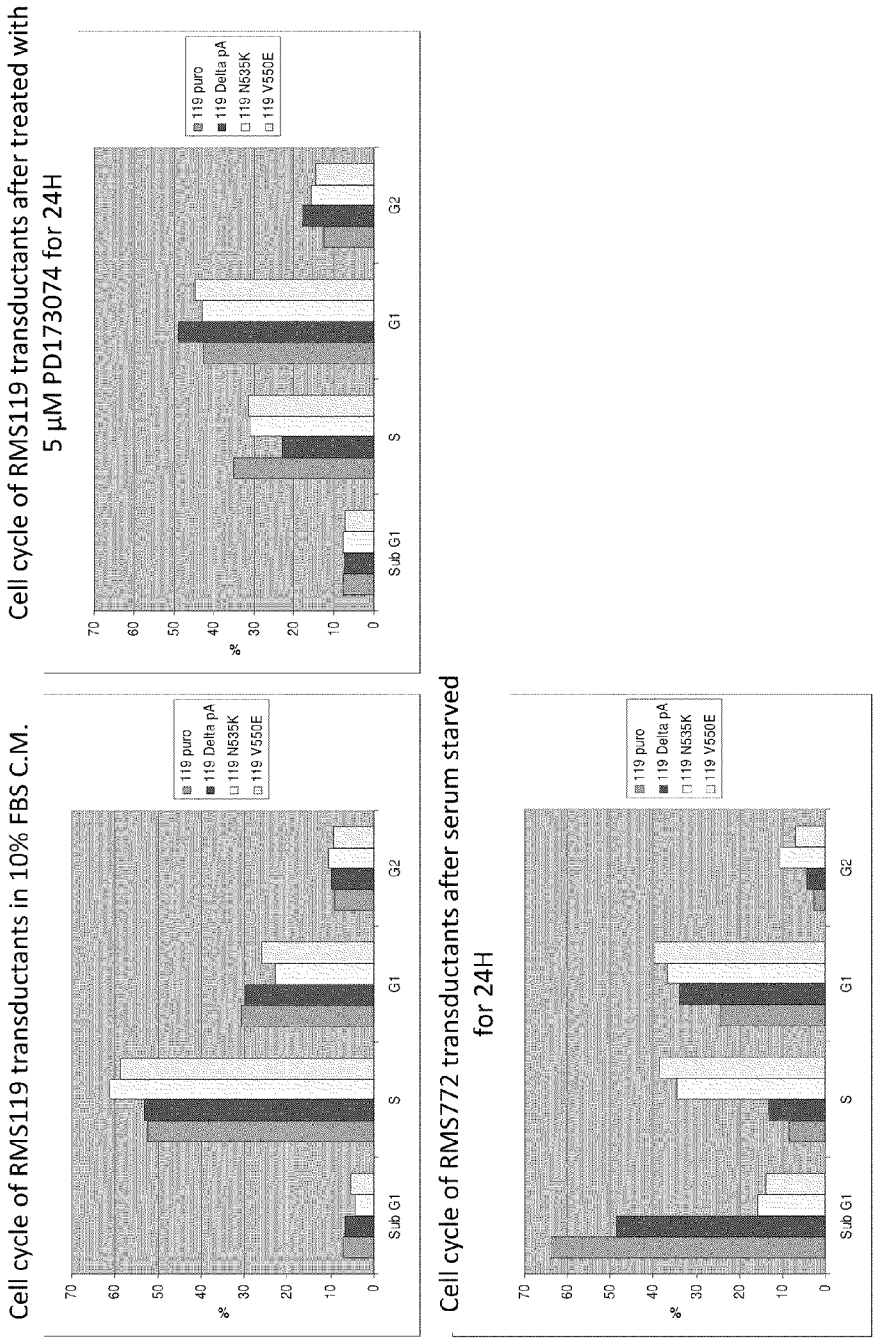
FIG. 9B shows the percentage of cells in each stage of the cell cycle of mouse RMS119 cells expressing vector only (puro), wild type (Delta pA), or mutant human FGFR4 cultured with varying amounts of fetal bovine serum or in the presence of PD173074 for 24 hours.

Murine RMS772 cells expressing FGFR4 TK domain mutations N535K or V550E treated with PD173074 showed an increase in apoptosis compared with cells transfected with vector or wild type FGFR4 (FIG. 9A). In contrast, RMS119 cells expressing FGFR4 N535K or V550E FGFR4 mutants were not affected by treatment with PD173074 (FIG. 9B).

Figure 10:
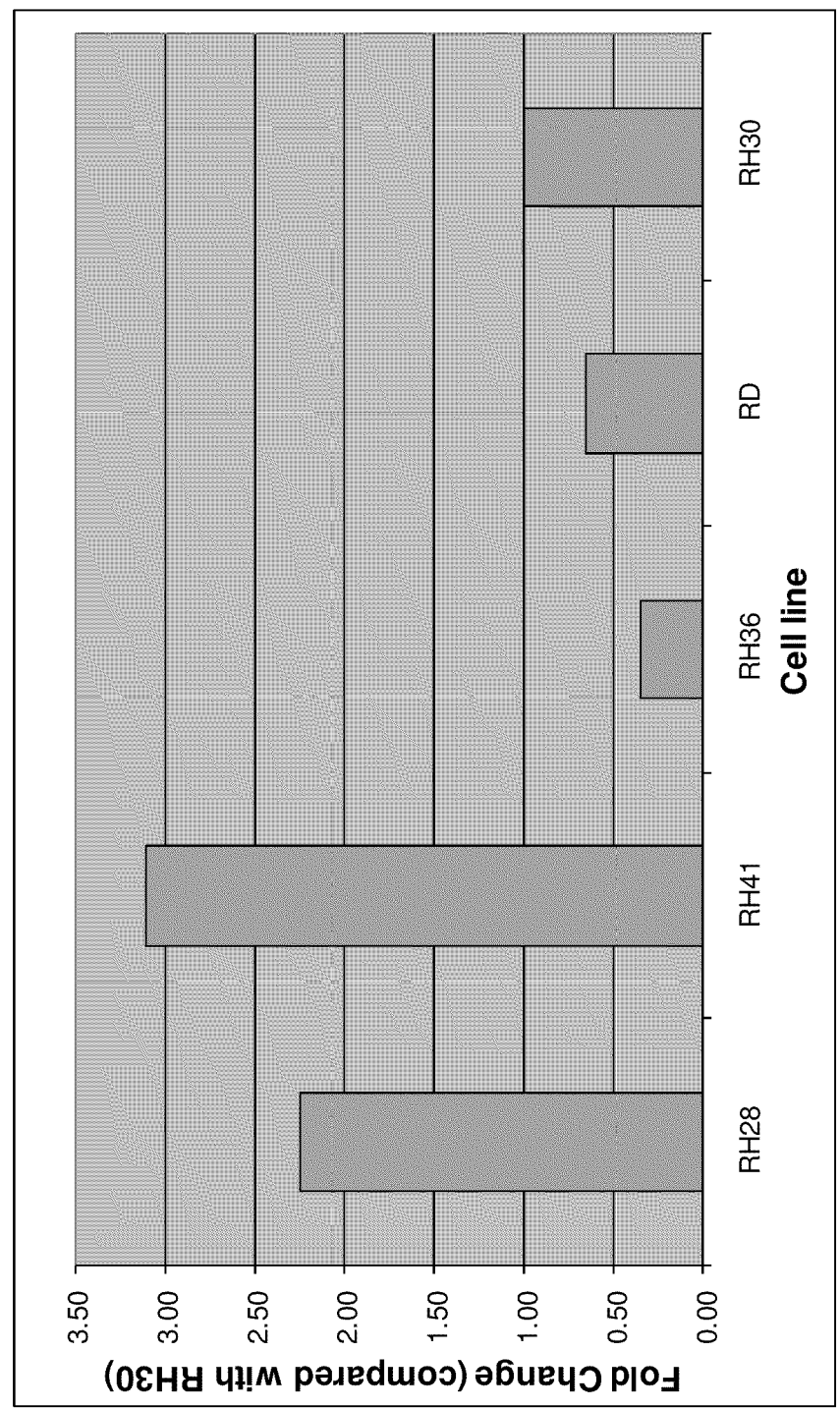
FIG. 10 shows FGFR4 expression level in human RMS cell lines, determined by real-time PCR.

Human RMS cell lines were treated with varying concentrations of PD173074 for 24 to 72 hours and the apoptotic cell fraction was determined. An $IC_{50}$ value for PD173074 was calculated for each cell line (Table 8). Expression level of FGFR4 mRNA for each cell line was determined by real-time PCR (FIG. 10). The $IC_{50}$ for PD173074 was generally correlated with FGFR4 expression level; that is, cells with a higher level of FGFR4 expression were more sensitive to killing by PD173074.

TABLE 8

$IC_{50}$ of PD173074 for Killing Human RMS Cell Lines

| Cell Line* | FGFR4 Fold Change† | 24 hours (µM) | 48 hours (µM) | 72 hours (µM) |
|---|---|---|---|---|
| RH41 | 3.10 | 2.55 | 0.96 | 0.76 |
| RH28 | 2.25 | 2.22 | 0.66 | 0.50 |
| RH30 | 1.00 | 10.04 | 8.32 | 8.11 |
| RD | 0.66 | 57.12 | 29.67 | 20.23 |
| RH36 | 0.35 | 25.9 | 17.62 | 20.23 |

*Cell lines are listed in order of relative FGFR4 gene expression, from highest to lowest.
†FGFR4 mRNA expression for each cell line reported as fold change where all values are normalized to the RH30 cell line.

Figure 11B:
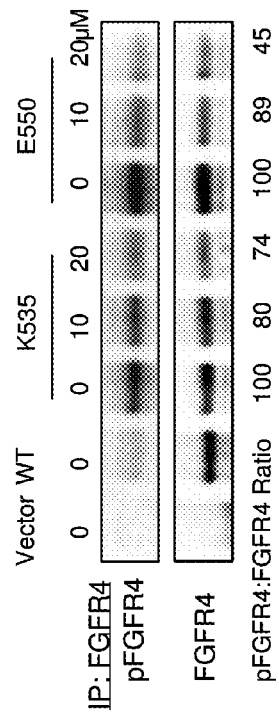
FIG. 11B is a Western blot showing phosphorylation of FGFR4 in RMS772 cells expressing vector only, wild type FGFR4, (WT), FGFR4 N535K (K535), or FGFR4 V550E (E550) following 3 hour treatment with carrying amounts of PD173074.
Figure 11C:
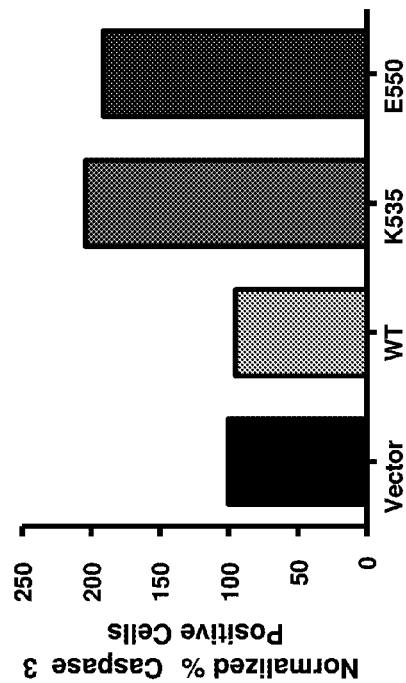
FIG. 11C shows percentage of cells positive for caspase 3 expression in RMS772 cells expressing vector only, wild type FGFR4 (WT), FGFR4 N535K (K535), or FGFR4 V550E (E550) following 24 hour treatment with 20 μM PD173074 (normalized to vector only).
Figure 11A:
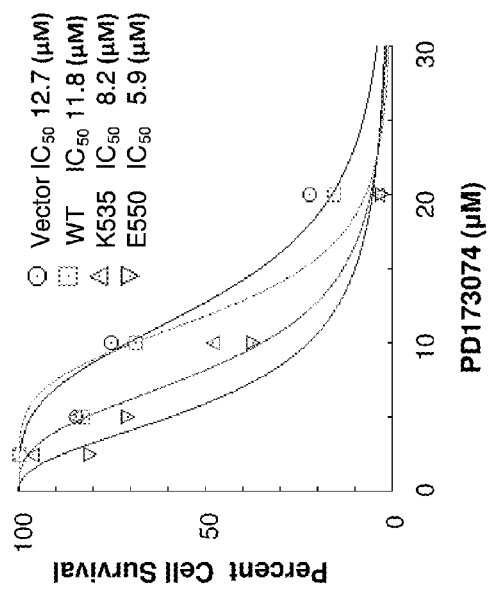
FIG. 11A shows percent cell survival of RMS772 cells expressing vector only, wild type FGFR4 (WT), FGFR4 N535K (K535), or FGFR4 V550E (E550) in the presence of varying amounts of PD173074 for 48 hours. The $IC_{50}$ for each cell line is shown.

To demonstrate FGFR4 activation dependence, the transduced RMS772 cell lines were treated with the FGFR inhibitor PD173074 (Grand et al., *Leukemia* 18:962-966, 2004; Mohammadi et al., *EMBO J.* 17:5896-5904, 1998). The $IC_{50}$ after 48 hours of treatment decreased from 12.7 µM and 11.8 µM in the vector control and wild type FGFR4 cell lines, respectively to 8.2 µM and 5.9 µM for K535 and E550, respectively (FIG. 11A). PD173074 reduced phospho-FGFR4 (normalized to total FGFR4) to 74% and 45% of pretreatment levels for K535 and E550, respectively, with 20 µM of drug (FIG. 11B). Increased apoptosis with PD173074 was apparent in both mutant cell lines as evidenced by an increased SubG1 fraction (FIG. 9A) and increased activated caspase 3 (FIG. 11C).

Figure 12:
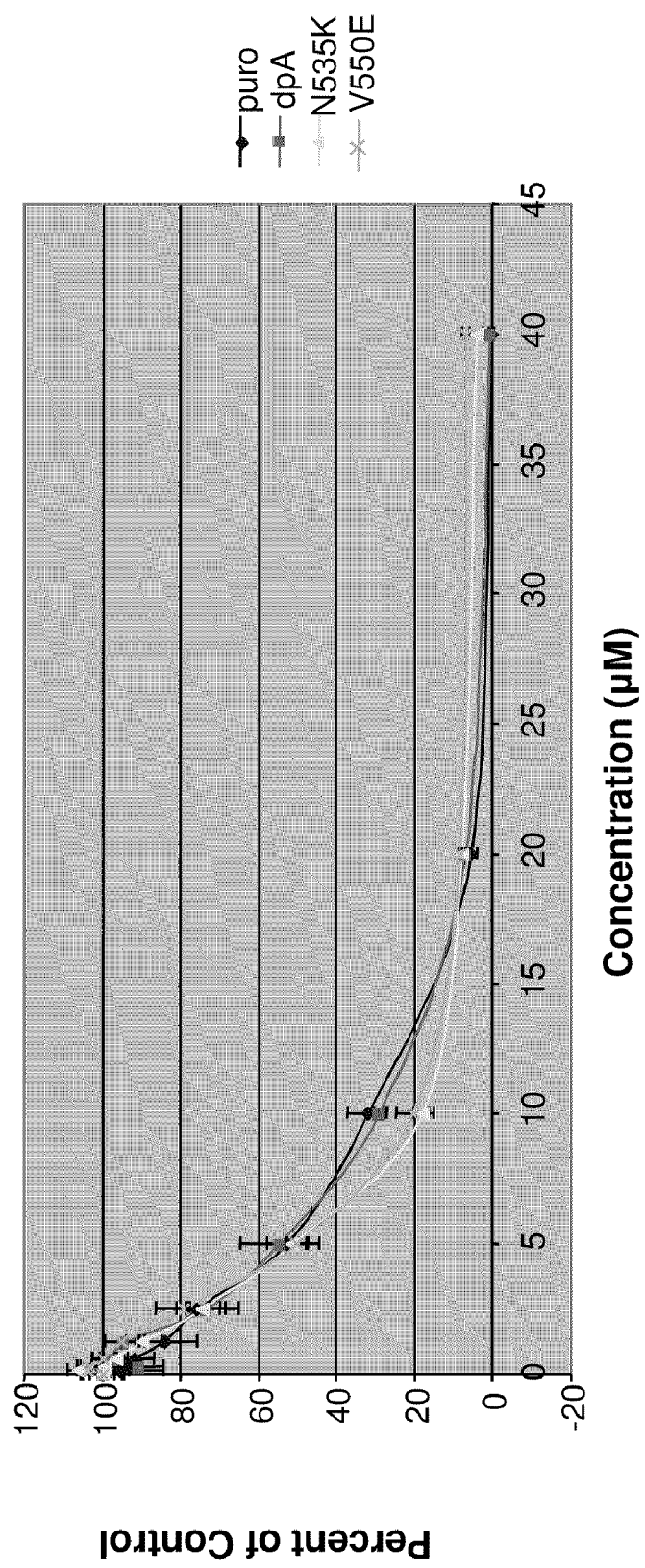
FIG. 12 shows percent cell survival of RMS772 cells expressing vector only (puro), wild type FGFR4 (dpA), FGFR4 N535K, or FGFR4 V550E in the presence of varying amounts of imatinib for 24 hours.

To determine the sensitivity of FGFR4 mutants (N535K and V550E) to imatinib, RMS772 transductants were treated with imatinib (ranging from 0 µM to 40 µM). After 24 hours, relative cell number (normalized with control) was plotted against imatinib dose. The FGFR4 mutants were more sensitive to 10 µM imatinib than wild type FGFR4 or control cells (FIG. 12).

Example 5

Effect of FGFR4 Knockdown on Tumor Growth and Metastasis

This example describes the effect of decreased FGFR4 expression on rhabdomyosarcoma growth and metastasis in an in vivo model.

Methods

Human rhabdomyosarcoma cell line RH30 was retrovirally transduced with vectors containing tetracycline repressor protein and ecotropic receptor. A tetracycline inducible shRNA construct targeting FGFR4 (AGCTAAAAAGCCGT-CAAGATGCTCAAAGACTCTCT-TGAAGTCTTTGAGCATCTTGACGGCGG, SEQ ID NO: 44) was used to transduce these RH30 cells as described previously (Ngo et al. Nature 441:106-110, 2006). Transduced RH30 cells were then subcloned. The subclone with the highest FGFR4 knockdown in the presence of doxycycline (dox) was used for in vitro and in vivo studies. The subclone chosen was designated as RH30 TRB H11.5 and was further transduced with a retroviral vector encoding luciferase. RH30 TRB H11.5 cells treated with or without 25 ng/ml doxycycline for 48 hours were harvested for Western blot for FGFR4 expression.

8-10 week old CB17.B6-Prkdc$^{scid}$ Lyst$^{bg}$/Crl (SCID Beige) mice were purchased from Charles River. Mice were fed a rodent diet containing doxycycline (Harlan Teklad, Madison, Wis.). $3\times10^6$ RH30 TRB H11.5 cells (after 48 hours in 25 ng/mL doxycycline (dox)) were injected intramuscularly into SCID Beige mice. Dox diet was initiated 48 hours prior to injection in the treatment group for all RH30 TRB H11.5 experiments, and this diet was continued for the duration of the experiment. Mice injected with RH30 TRB H11.5 without dox treatment and mice without dox diet served as controls. Xenogen imaging was used to assess tumor growth.

SCID Beige mice were intravenously injected with $1\times10^6$ RH30 TRB H11.5 cells per day for 4 consecutive days (after 48 hours in 25 ng/mL dox). For this group, mice were treated with continuous dox diet. Mice receiving non-dox pretreated RH30 TRB H11.5 and with control diet served as controls. Pulmonary metastases were detected with Xenogen imaging For Xenogen imaging, 3 mg luciferin was injected intraperitoneally into each mouse. 10 minutes later, the mouse was anesthetized and a Xenogen IVIS 100 system (Caliper Life Sciences, Hopkinton, Mass.) was used to monitor the tumor in vivo.

Results

RH30 cells were transduced with tetracycline repressor and a tetracycline-inducible FGFR4 shRNA (designated RH30 TRB H11.5). Western blotting showed that treatment of the cells with 25 nM dox for 48 hours resulted in almost complete inhibition of FGFR4 expression (FIG. 13A). There was no difference in the growth of the cells in the presence or absence of dox in vitro, as monitored by RT-CES MP for 126 hours (FIG. 13B), however there was a 41% reduction (P=0.0021) in growth after prolonged culture for 13 days (FIG. 13C).

Figure 14A:
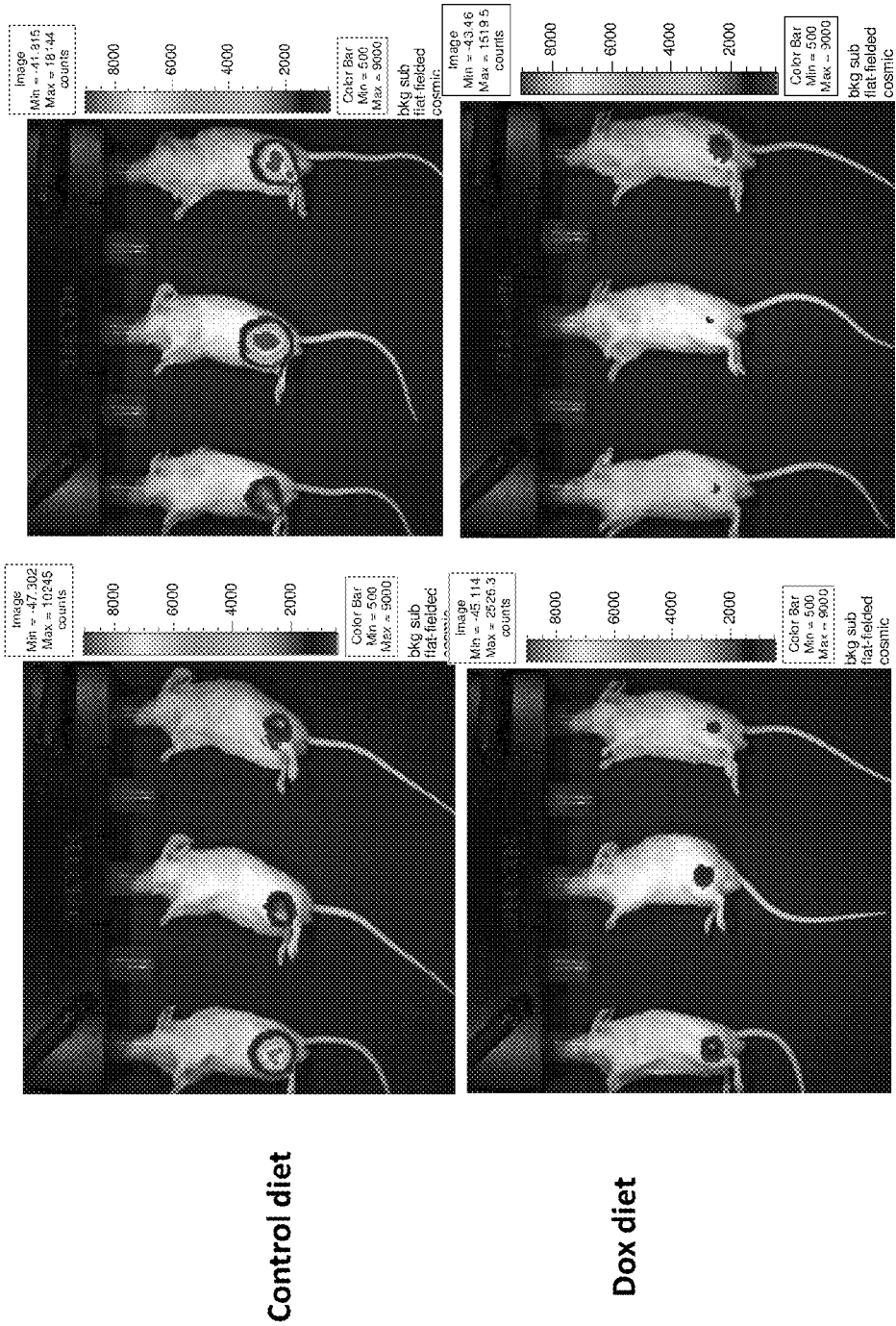
FIG. 14A is photographs of mice imaged by in vivo imaging 31 days following intramuscular injection with RH30 TRB H11.5 cells and fed control diet or dox diet.
Figure 14B:
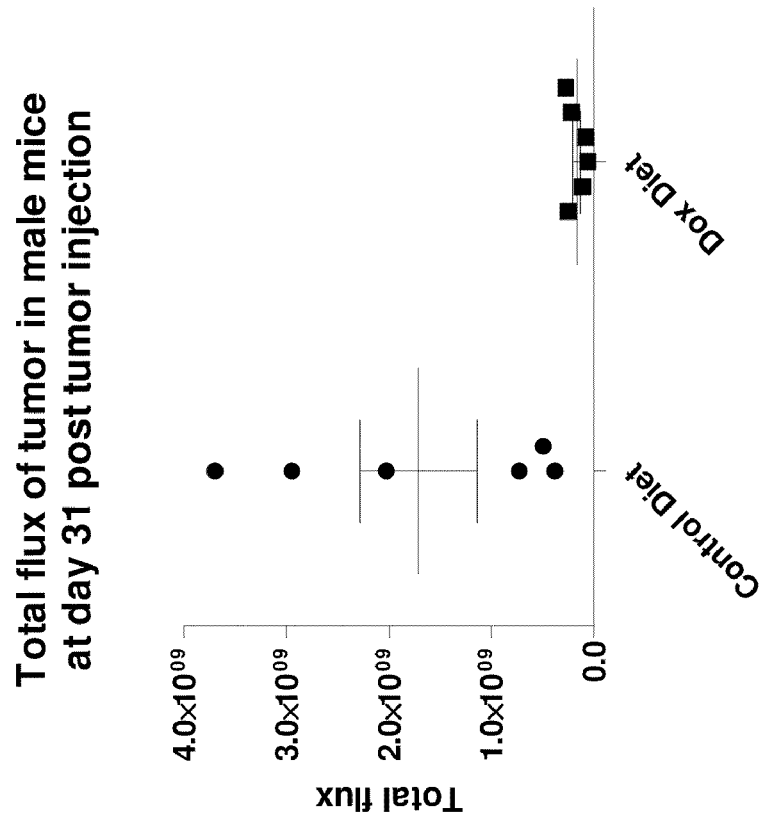
FIG. 14B shows total flux in mice fed control or dox diet.

RH30 TRB H11.5 cells were also transduced with luciferase in order to detect the cells in vivo utilizing the Xenogen IVIS 100 bioluminescent imaging system. To determine the effect of FGFR4 knockdown on tumor growth, mice were injected intramuscularly with RH30 TRB H11.5 cells and tumor cells were monitored with the Xenogen system following injection with luciferin. There was no significant difference in the luminescent signal in mice pretreated with dox diet or control diet at 1 hour following injection of RH30 TRB H11.5 cells. However, the mice fed the dox diet for 31 days following RH30 TRB H11.5 cell injection had significantly lower signal than mice fed control diet (FIG. 14). The control diet mice had large visible tumors on their flank, while dox fed mice did not have visible tumors.

Figure 15A:
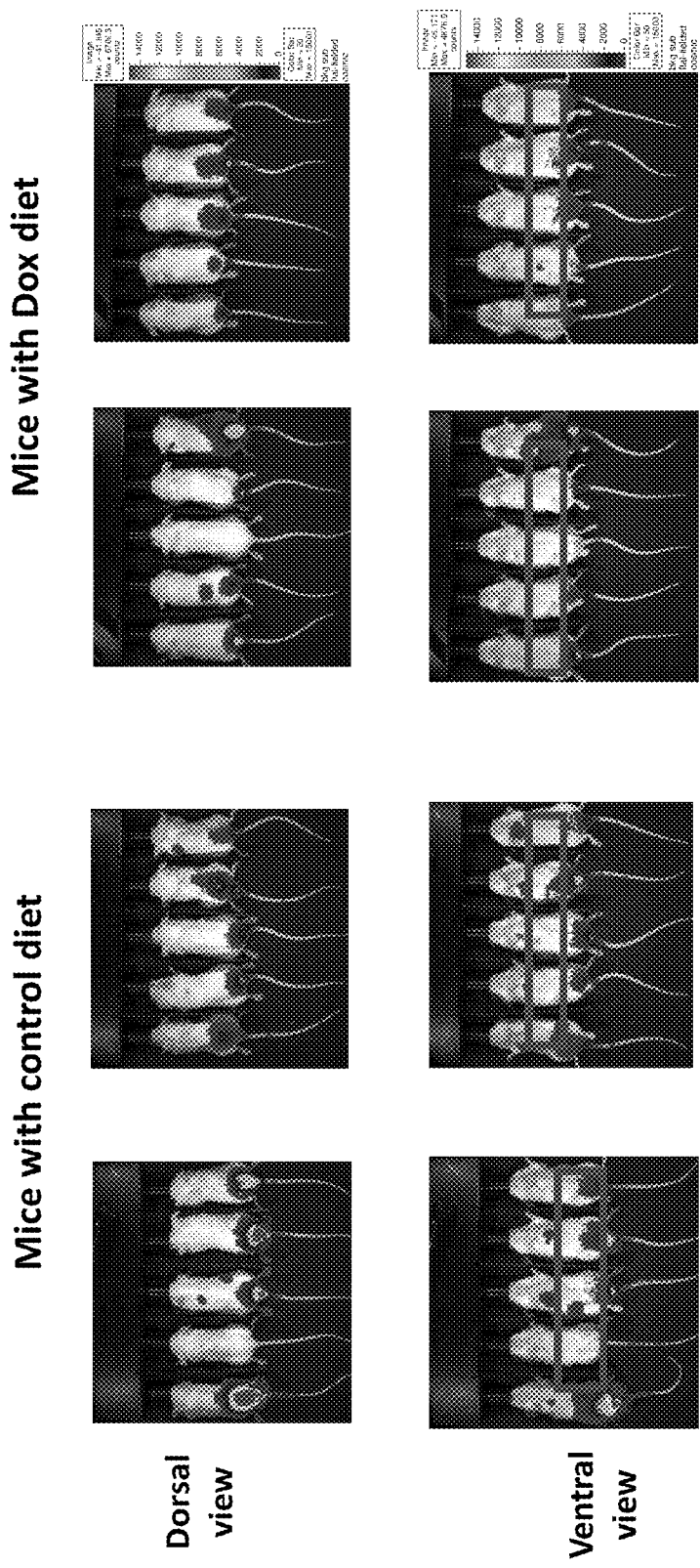
FIG. 15A is photographs of mice imaged by in vivo imaging 74 days following intravenous injection of RH30 TRB H11.5 cells and fed control diet (left) or dox diet (right) including both dorsal and ventral views.
Figure 15B:
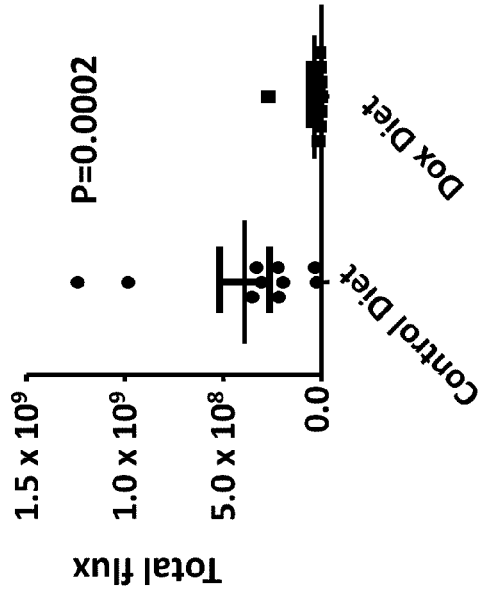
FIG. 15B shows total flux in the lungs of mice 73 days after intravenous injection of RH30 TRB H11.5 cells with feeding with control or dox diet.
Figure 15C:
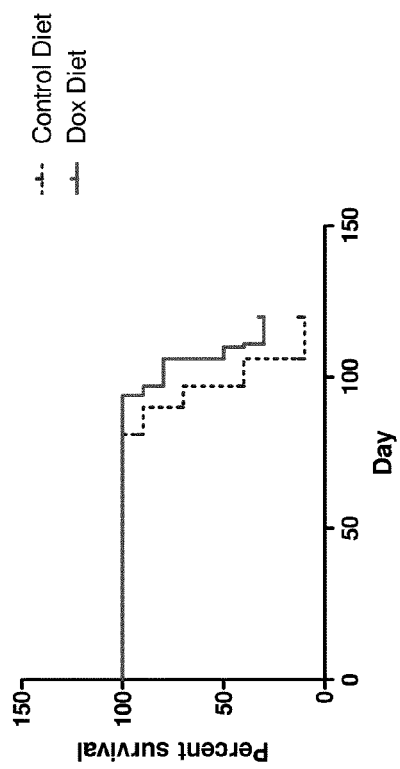
FIG. 15C is a Kaplan-Meier survival curve of mice injected intravenously with RH30 TRB H11.5 cells and fed control or dox diet.

To determine the effect of FGFR4 knockdown on tumor metastasis, mice were injected intravenously with RH30 TRB H11.5 cells and tumor cells were monitored with the Xenogen system following injection with luciferin. Mice fed control diet had large abdominal tumors and had pulmonary metastases as assessed by in vivo imaging 74 days post-injection (FIG. 15A). In contrast, dox-fed mice generally had smaller abdominal tumors and reduced pulmonary metastases (FIGS. 15A and 15B). In addition, dox-fed mice had significantly better survival than control diet fed mice (FIG. 15C).

Example 6

Testing Inhibitors of FGFR4 for Anti-Metastatic Activity

This example describes methods for testing anti-metastatic activity of inhibitors of FGFR4.

A. Metastasis Models

Growth factor receptor inhibitors, such as FGFR inhibitors may be tested for their ability to decrease, inhibit, or prevent tumor metastasis utilizing in vivo models of metastasis (see e.g. Khanna and Hunter, Carcinogenesis 26:513-523, 2005). One model of tumor metastasis utilizes transplantation of tumor cell lines or tissues in syngenic or xenograft models. In syngenic models, cancer cell lines or tissues are transplanted in animals (such as a mouse or rat) of the same genetic background as the cell line or tissue. In xenograft models, human cancer cell lines or tissues are transplanted into immunocompromised animals (such as SCID or nude mice), such as by subcutaneous injection of tumor cells. In either model, following transplantation, the development of the primary tumor and the number, size, location, and time to develop of metastases can be determined, for example by necropsy or by imaging studies (for example, bioluminescence, magnetic resonance imaging, or positron enhanced tomography).

Another in vivo model of metastasis involves injection of tumor cells directly into the systemic circulation of an animal, such as a mouse or rat. For example, cancer cell lines or tumor cells can be injected into the tail vein, intrasplenic or portal vein, or arterial circulation (intracardiac injection). Injection of tumor cells into the systemic circulation can lead to formation of metastases at various sites, including lung, liver, bone, or other organs. In some examples, about $10^4$ to $10^7$ tumor cells are injected into the circulation, for example about $10^5$ to $10^6$ cells. The number, size, location, and time to develop of metastases can be determined following injection.

In further examples, an orthotopic transplantation model can be used to assess tumor metastasis in vivo. This method delivers cancer cells to the anatomic location or tissue from which the tumor was derived. For example, tumor cells may be transplanted by direct injection into the organ or tissue, or by surgical implantation of tumor fragments. Metastasis of the implanted tumor cells to sites away from the orthotopic site can be assessed in terms of number, size, location, and time of development.

B. Assessing Anti-Metastatic Activity of FGFR4 Inhibitors

The anti-metastatic efficacy of FGFR4 inhibitors, such as those identified by the methods described herein, can be assessed using in vivo metastasis models. In one example, tumor cells or cell lines (such as RMS tumors or cell lines) are injected in the tail vein of nude mice. The tumor cells may include human RMS cell lines (such as RH41, RH28, RH30, RH36, or RD cell lines), or mouse RMS cell lines (such as RMS119 or RMS772 cell lines). The tumor cells may also include cells that express a heterologous protein, such as a variant FGFR4 protein (such as mouse RMS119 or RMS772 cells that express human FGFR4 N535K or V550E variant proteins). In some examples, about $10^4$ to $10^7$ tumor cells are injected into the circulation, for example about $10^5$ to $10^6$ cells.

Mice are treated with known FGFR4 inhibitors (such as SU5402, TKI258, PD173074, or imatinib) or test compounds that are identified as inhibitors of tumor metastasis by the methods provided herein. The compounds can be administered prior to injection of tumor cells, simultaneously with injection, and/or at time points following injection. The FGFR4 inhibitors can be administered by any appropriate route, including parenteral (for example, intravenously, intraperitoneally, intramuscularly, or subcutaneously) or oral administration. Suitable dosages can be determined, for example, therapeutic efficacy and toxicity can be determined by standard pharmaceutical procedures such as, for example, by determination of the median effective dose, or $ED_{50}$ (i.e. the dose therapeutically effective in 50% of the population) and the median lethal dose, or $LD_{50}$ (i.e. the dose lethal to 50% of the population). The dose ratio between therapeutic and toxic effects is known as the "therapeutic index," which can be expressed as the ratio, $LD_{50}/ED_{50}$. The data obtained from cell culture assays and animal studies can be used to formulate a range of dosage for human or animal use. The dosage contained in such compositions is usually within a range of concentrations that include the $ED_{50}$ and demonstrate little or no toxicity. The dosage varies within this range depending upon the dosage form employed, sensitivity of the subject, the route of administration, and the like. In some examples, the dose of a FGFR4 inhibitor administered is about 0.1 mg/kg to about 1000 mg/kg. In particular examples, the dose is about 1 mg/kg to about 100 mg/kg, such as about 40 mg/kg.

Following treatment with FGFR4 inhibitors which are candidate inhibitors of tumor metastasis, the animals injected with tumor cells or cell lines are evaluated for size, number, and location of metastases. For example, if cells are injected in the tail vein, lung metastases are determined. Metastases in animals which receive varying doses of FGFR4 inhibitors are compared with control animals which are treated with vehicle alone. Similarly, animals which are injected with cells expressing a FGFR4 variant may be compared with animals injected with cells expressing wild type FGFR4 or other suitable controls. A compound which decreases the number of metastases, such as by at least about 10%, 20%, 30%, 40%, 50%, 60%, 70%, 80%, 90%, or 95% as compared with a control group is identified as a compound that inhibits FGFR4 and decreases risk of tumor metastasis. A compound which decreases the size of metastases by at least about 10%, 20%, 30%, 40%, 50%, 60%, 70%, 80%, 90%, or 95% as compared with a control group is identified as a compound that inhibits FGFR4 and decreases risk of tumor metastasis. Likewise, a compound that delays the development of metastases, for example, by at least about one week, two weeks, one month, three months, six months, or one year as compared to a control group is identified as a compound that inhibits FGFR4 and decreases risk of metastasis.

Example 7

Production of FGFR4 Antibodies

Monoclonal or polyclonal antibodies may be produced to either the normal FGFR4 protein or variants of this protein, for instance particular portions that contain a mutation and therefore may provide a distinguishing epitope. Optimally, antibodies raised against these proteins or peptides would specifically detect the protein or peptide with which the antibodies are generated. That is, an antibody generated to the FGFR4 protein or a fragment thereof would recognize and bind the FGFR4 protein and would not substantially recognize or bind to other proteins found in human cells. In some embodiments, an antibody is specific for (or measurably preferentially binds to) an epitope in a variant protein versus the wild type protein, or vice versa, as discussed more fully herein.

The determination that an antibody specifically detects the FGFR4 protein is made by any one of a number of standard immunoassay methods; for instance, the Western blotting technique (Sambrook et al., In *Molecular Cloning: A Laboratory Manual*, CSHL, New York, 1989). To determine that a given antibody preparation (such as one produced in a mouse) specifically detects the FGFR4 protein by Western blotting, total cellular protein is extracted from human cells (for example, lymphocytes) and electrophoresed on a sodium dodecyl sulfate-polyacrylamide gel. The proteins are then transferred to a membrane (for example, nitrocellulose) by Western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase. Application of an alkaline phosphatase substrate 5-bromo-4-chloro-3-indolyl phosphate/nitro blue tetrazolium results in the production of a dense blue compound by immunolocalized alkaline phosphatase. Antibodies that specifically detect the FGFR4 protein will, by this technique, be shown to bind to the FGFR4 protein band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-FGFR4 protein binding.

Methods to produce FGFR4 protein are known to one of skill in the art. For example, substantially pure FGFR4 protein or protein fragment (peptide) suitable for use as an immunogen may be isolated from cells transfected or transformed with a FGFR4 or FGFR4 variant construct. Concentration of protein or peptide in the final preparation is adjusted, for example, by concentration on an Amicon filter device, to the level of a few micrograms per milliliter. Monoclonal or polyclonal antibody to the protein can then be prepared as follows:

A. Monoclonal Antibody Production by Hybridoma Fusion

Monoclonal antibody to epitopes of the FGFR4 protein identified and isolated as described can be prepared from murine hybridomas according to the classical method of Kohler and Milstein (*Nature* 256:495-497, 1975) or derivative methods thereof. Briefly, a mouse is repetitively inoculated with a few micrograms of the selected protein over a period of a few weeks. The mouse is then sacrificed, and the antibody-producing cells of the spleen isolated. The spleen cells are fused by means of polyethylene glycol with mouse myeloma cells, and the excess un-fused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Meth. Enzymol.* 70:419-439, 1980), and derivative methods thereof. Selected positive clones can be expanded and their monoclonal antibody product harvested for use. Detailed procedures for monoclonal antibody production are described in Harlow and Lane (*Antibodies, A Laboratory Manual*, CSHL, New York, 1988).

In addition, protocols for producing humanized forms of monoclonal antibodies and fragments of monoclonal antibodies are known in the art (see, e.g., U.S. Pat. Nos. 6,054,297, 6,407,213, 6,639,055, 6,800,738, and 6,719,971 and U.S. Pat. Appl. Pub. Nos. 2005/0033031, and 2004/0236078).

B. Polyclonal Antibody Production by Immunization

Polyclonal antiserum containing antibodies to heterogeneous epitopes of a single protein can be prepared by immunizing suitable animals with the expressed protein, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with either inadequate or excessive doses of antigen resulting in low titer antisera. Small doses (ng level) of antigen administered at multiple intradermal sites appear to be most reliable. An effective immunization protocol for rabbits can be found in Vaitukaitis et al. (*J. Clin. Endocrinol. Metab.* 33:988-991, 1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony et al. (In *Handbook of Experimental Immunology*, Wier, D. (ed.) chapter 19. Blackwell, 1973). Plateau concentration of antibody is usually in the range of about 0.1 to 0.2 mg/ml of serum (about 12 µM). Affinity of the antisera for the antigen is determined by preparing competitive binding curves, as described, for example, by Fisher (*Manual of Clinical Immunology*, Ch. 42, 1980).

C. Antibodies Raised Against Synthetic Peptides

A third approach to raising antibodies against the FGFR4 protein or peptides is to use one or more synthetic peptides synthesized on a commercially available peptide synthesizer based upon the predicted amino acid sequence of the FGFR4 protein or peptide or variants thereof. Polyclonal antibodies can be generated by injecting these peptides into, for instance, rabbits or mice.

With the provision of several variant FGFR4 proteins, the production of antibodies that specifically recognize these proteins (and peptides derived therefrom) is enabled. In particular, production of antibodies (and fragments and engineered versions thereof) that recognize at least one FGFR4 variant with a higher affinity than they recognize wild type FGFR4 is beneficial, as the resultant antibodies can be used in diagnosis and treatment, as well as in study and examination of the FGFR4 proteins themselves.

In particular embodiments, it is beneficial to generate antibodies from a peptide taken from a mutation or variation-specific region of the FGFR4 protein. By way of example, such regions include a portion or the entire TK domain of FGFR4 (such as amino acids 460-746). More particularly, it is beneficial to raise antibodies against peptides of four or more contiguous amino acids that overlap the variants in the TK domain described herein, and particularly which comprise at least four contiguous amino acids including the residue(s) shown in position(s) 535, 550, and/or 554 of SEQ ID NO: 2. In additional embodiments, it is beneficial to generate antibodies from a peptide taken from the extracellular domain of FGFR4 (amino acids 1-378).

Similarly, it is beneficial to raise antibodies against peptides of 4 or more contiguous amino acids that overlap the FGFR4 variants described herein, and particularly which comprise at least four contiguous amino acids including the residue(s) shown in position(s) 10, 56, 72, 122, 136, 175, 234, 535, 550, 554, or 576 of SEQ ID NO: 2, or a combination thereof.

Longer peptides also can be used, and in some instances will produce a stronger or more reliable immunogenic response. Thus, it is contemplated in some embodiments that more than four amino acids are used to elicit the immune response, for instance, at least 5, at least 6, at least 8, at least 10, at least 12, at least 15, at least 18, at least 20, at least 25, or more, such as 30, 40, 50, or even longer peptides. Also, it will be understood by those of ordinary skill that it is beneficial in some instances to include adjuvants and other immune response enhancers, including passenger peptides or proteins, when using peptides to induce an immune response for production of antibodies.

Embodiments are not limited to antibodies that recognize epitopes containing the actual mutation identified in each variant. Instead, it is contemplated that variant-specific antibodies also may each recognize an epitope located anywhere throughout the FGFR4 variant molecule, which epitopes are changed in conformation and/or availability because of the amino acid variation. Antibodies directed to any of these variant-specific epitopes are also encompassed herein.

By way of example, the following references provide descriptions of methods for making antibodies specific to mutant proteins: Hills et al., (*Int. J. Cancer*, 63: 537-543, 1995); Reiter & Maihle (*Nucleic Acids Res.*, 24: 4050-4056, 1996); Okamoto et al. (*Br. J. Cancer*, 73: 1366-1372, 1996); Nakayashiki et al., (*Jpn. J. Cancer Res.*, 91: 1035-1043, 2000); Gannon et al. (*EMBO J.*, 9: 1595-1602, 1990); Wong et al. (*Cancer Res.*, 46: 6029-6033, 1986); and Carney et al. (*J. Cell Biochem.*, 32: 207-214, 1986). Similar methods can be employed to generate antibodies specific to specific FGFR4 variants.

D. Antibodies Raised by Injection of FGFR4 Encoding Sequence

Antibodies may be raised against FGFR4 proteins and peptides by subcutaneous injection of a DNA vector that expresses the desired protein or peptide, or a fragment thereof, into laboratory animals, such as mice. Delivery of the recombinant vector into the animals may be achieved using a hand-held form of the Biolistic system (Sanford et al., *Particulate Sci. Technol.* 5:27-37, 1987) as described by Tang et al. (*Nature* 356:152-154, 1992). Expression vectors suitable for this purpose may include those that express the FGFR4 encoding sequence under the transcriptional control of either the human β-actin promoter or the cytomegalovirus (CMV) promoter.

Antibody preparations prepared according to these protocols are useful in quantitative immunoassays which determine concentrations of antigen-bearing substances in biological samples; they are also used semi-quantitatively or qualitatively to identify the presence of antigen in a biological sample; or for immunolocalization of the FGFR4 protein.

In addition, antibodies to FGFR4 are commercially available. See, for instance, rabbit anti-FGFR4 (catalog nos. ab5481 or ab41948) or mouse anti-FGFR4 (catalog nos. ab49306 or ab49309) from Abcam, Inc. (Cambridge, Mass.) and rabbit anti-FGFR4 (catalog nos. sc-124 or sc-9006) or mouse anti-FGFR4 (catalog no. sc-73995), from Santa Cruz Biotechnology, Inc. (Santa Cruz, Calif.).

For administration to human patients, antibodies, e.g., FGFR4-specific monoclonal antibodies, can be humanized by methods known in the art. Antibodies with a desired binding specificity can be commercially humanized (Scotgene, Scotland, UK; Oxford Molecular, Palo Alto, Calif.).

Example 8

Kits

Kits are provided which contain the necessary reagents for determining the presence or absence of mutation(s) in a FGFR4-encoding sequence, such as probes or primers specific for the FGFR4 gene or a highly variable region of this gene or antibodies specific for wild type or variant FGFR4 protein. Such kits can be used with the methods described herein to determine whether a subject is predisposed to metastatic disease or tumor development, or whether the subject is expected to respond to one or another therapy, such as a particular tyrosine kinase inhibitory compound.

The provided kits may also include written instructions. The instructions can provide calibration curves or charts to compare with the determined (e.g., experimentally measured) values. Kits are also provided to determine elevated or depressed expression of mRNA (i.e., containing probes) or FGFR4 protein (i.e., containing antibodies or other FGFR4-protein specific binding agents).

A. Kits for Amplification of FGFR4 Sequences

Oligonucleotide probes and primers, including those disclosed herein, can be supplied in the form of a kit for use in detection of a predisposition to neoplastic disease or tumor formation in a subject. In such a kit, an appropriate amount of one or more of the oligonucleotide primers is provided in one or more containers. The oligonucleotide primers may be provided suspended in an aqueous solution or as a freeze-dried or lyophilized powder, for instance. The container(s) in which the oligonucleotide(s) are supplied can be any conventional container that is capable of holding the supplied form, for instance, microfuge tubes, ampoules, or bottles. In some applications, pairs of primers may be provided in pre-measured single use amounts in individual, typically disposable, tubes or equivalent containers. With such an arrangement, the sample to be tested for the presence of a FGFR4 mutation can be added to the individual tubes and amplification carried out directly.

The amount of each oligonucleotide primer supplied in the kit can be any appropriate amount, depending for instance on the market to which the product is directed. For instance, if the kit is adapted for research or clinical use, the amount of each oligonucleotide primer provided would likely be an amount sufficient to prime several PCR amplification reactions. Those of ordinary skill in the art know the amount of oligonucleotide primer that is appropriate for use in a single amplification reaction. General guidelines may for instance be found in Innis et al. (PCR Protocols, A Guide to Methods and Applications, Academic Press, Inc., San Diego, Calif., 1990), Sambrook et al. (In Molecular Cloning: A Laboratory Manual, Cold Spring Harbor, N.Y., 1989), and Ausubel et al. (In Current Protocols in Molecular Biology, Greene Publ. Assoc. and Wiley-Intersciences, 1992).

A kit may include more than two primers, in order to facilitate the in vitro amplification of FGFR4 sequences, for instance the FGFR4 gene or the 5' or 3' flanking region thereof, or particular exons thereof.

In some embodiments, kits may also include the reagents necessary to carry out nucleotide amplification reactions, including, for instance, DNA sample preparation reagents, appropriate buffers (e.g., polymerase buffer), salts (e.g., magnesium chloride), and deoxyribonucleotides (dNTPs).

Kits may in addition include either labeled or unlabeled oligonucleotide probes for use in detection of FGFR4 variant(s)/mutation(s). In certain embodiments, these probes will be specific for a potential mutation that may be present in the target amplified sequences. The appropriate sequences for such a probe will be any sequence that includes one or more of the identified variants, particularly nucleotide positions that overlap with the variants shown in Table 3 or Table 7, such that the sequence of the probe is complementary to a variant site and the surrounding FGFR4 sequence.

It may also be advantageous to provide in the kit one or more control sequences for use in the amplification reactions. The design of appropriate positive control sequences is well known to one of ordinary skill in the appropriate art.

B. Kits for Detection of FGFR4 mRNA Expression

Kits similar to those disclosed above for the detection of FGFR4 mutations directly can be used to detect FGFR4 mRNA expression, such as over- or under-expression. Such kits include an appropriate amount of one or more oligonucleotide primers for use in, for instance, reverse transcription PCR reactions, similar to those provided above with art-obvious modifications for use with RNA amplification.

In some embodiments, kits for detection of altered expression of FGFR4 mRNA may also include some or all of the reagents necessary to carry out RT-PCR in vitro amplification reactions, including, for instance, RNA sample preparation reagents (including e.g., an RNase inhibitor), appropriate buffers (e.g., polymerase buffer), salts (e.g., magnesium chloride), and deoxyribonucleotides (dNTPs). Written instructions may also be included.

Such kits may in addition include either labeled or unlabeled oligonucleotide probes for use in detection of the in vitro amplified target sequences. The appropriate sequences for such a probe will be any sequence that falls between the annealing sites of the two provided oligonucleotide primers, such that the sequence the probe is complementary to is amplified during the PCR reaction. In certain embodiments, these probes will be specific for a potential mutation that may be present in the target amplified sequences, for instance specific for the N535K, N535D, V550E or V5550L point mutations or another mutation identified in FGFR4, particularly the TK domain mutations.

It may also be advantageous to provide in the kit one or more control sequences for use in the RT-PCR reactions. The design of appropriate positive control sequences is well known to one of ordinary skill in the appropriate art.

Alternatively, kits may be provided with the necessary reagents to carry out quantitative or semi-quantitative Northern analysis of FGFR4 mRNA. Such kits include, for instance, at least one FGFR4-specific oligonucleotide for use as a probe. This oligonucleotide may be labeled in any conventional way, including with a selected radioactive isotope, enzyme substrate, co-factor, ligand, chemiluminescent or fluorescent agent, hapten, or enzyme. In certain embodiments, such probes will be specific for a potential mutation that may be present in the target amplified sequence, such as the mutations disclosed herein.

C. Kits for Detection of FGFR4 Protein Expression

Kits for the detection of FGFR4 protein expression (such as over- or under-expression) are also encompassed. Such kits may include at least one target protein specific binding agent (e.g., a polyclonal or monoclonal antibody or antibody fragment that specifically recognizes the FGFR4 protein) and may include at least one control (such as a determined amount of FGFR4 protein, or a sample containing a determined amount of FGFR4 protein). The FGFR4-protein specific binding agent and control may be contained in separate containers. Likewise, kits for detection of mutant FGFR4 may include at least one target protein binding agent (e.g., a polyclonal or monoclonal antibody or antibody fragment) that specifically recognizes the FGFR4 protein only when an FGFR4 mutant is expressed.

The FGFR4 protein expression detection kits may also include a means for detecting FGFR4:binding agent complexes, for instance the agent may be detectably labeled. If the detectable agent is not labeled, it may be detected by second antibodies or protein A for example, which may also be provided in some kits in one or more separate containers. Such detection techniques are well known.

Additional components in specific kits may include instructions for carrying out the assay. Instructions will allow the tester to determine whether FGFR4 expression levels are elevated. Reaction vessels and auxiliary reagents such as chromogens, buffers, enzymes, etc. may also be included in the kits.

D. Kits for Detection of Homozygous versus Heterozygous Allelism

Also provided are kits that allow differentiation between individuals who are homozygous versus heterozygous for FGFR4 mutations, such as the N535D, N535K, V550E, or V550L mutations. Such kits provide the materials necessary to perform oligonucleotide ligation assays (OLA), as described at Nickerson et al. (*Proc. Natl. Acad. Sci. USA* 87:8923-8927, 1990). In specific embodiments, these kits contain one or more microtiter plate assays, designed to detect mutation(s) in the FGFR4A sequence of a subject.

Additional components in some of these kits may include instructions for carrying out the assay. Instructions will allow the tester to determine whether a FGFR4 allele is homozygous or heterozygous. Reaction vessels and auxiliary reagents such as chromogens, buffers, enzymes, etc. may also be included in the kits.

It may also be advantageous to provide in the kit one or more control sequences for use in the OLA reactions. The design of appropriate positive control sequences is well known to one of ordinary skill in the appropriate art.

In view of the many possible embodiments to which the principles of the disclosure may be applied, it should be recognized that the illustrated embodiments are only preferred examples and should not be taken as limiting the scope of the invention. Rather, the scope of the invention is defined by the following claims. We therefore claim as our invention all that comes within the scope and spirit of these claims.

We claim:

1. A method for identifying a tumor as having an increased likelihood of responding to treatment with an inhibitor of fibroblast growth factor receptor 4 (FGFR4), wherein the response comprises tumor cell death, inhibition of tumor growth, or decreased risk of metastasis of the tumor, comprising:
   detecting the presence of an FGFR4 protein variant in a tumor sample from a subject, wherein the FGFR4 protein variant comprises at least one of a lysine at the position corresponding to position 535 of SEQ ID NO: 2 or a glutamic acid at the position corresponding to position 550 of SEQ ID NO: 2; or
   detecting the presence of an FGFR4 nucleic acid variant in a tumor sample from a subject, wherein the FGFR4 nucleic acid variant encodes an FGFR4 protein comprising at least one of a lysine at the position corresponding to position 535 of SEQ ID NO: 2 or a glutamic acid at the position corresponding to position 550 of SEQ ID NO: 2,
   wherein the presence of the variant indicates that the tumor has an increased likelihood of responding to treatment with an inhibitor of FGFR4.

2. The method of claim 1, wherein the variant comprises a somatic mutation.

3. The method of claim 1, wherein the tumor comprises a rhabdomyosarcoma.

4. The method of claim 1, comprising reacting at least one FGFR4 molecule contained in the tumor sample from the subject with a reagent comprising a FGFR4-specific binding agent to form a FGFR4:agent complex.

5. The method of claim 4, wherein the FGFR4 specific binding agent is a FGFR4 oligonucleotide or a FGFR4 protein specific binding agent.

6. The method of claim 5, wherein the agent comprises a labeled nucleotide probe.

7. The method of claim 6, further comprising in vitro amplifying a FGFR4 nucleic acid prior to detecting the FGFR4 variant.

8. The method of claim 4, wherein the FGFR4-specific binding agent is a FGFR4-specific antibody or a functional fragment thereof.

9. The method of claim 8, wherein the complexes are detected by Western blot assay or ELISA.

10. The method of claim 8, wherein the antibody is a monoclonal antibody.

11. The method of claim 10, wherein the monoclonal antibody recognizes an epitope of a variant FGFR4 and not an epitope of wild type FGFR4.

12. The method of claim 1, wherein the inhibitor of FGFR4 comprises a small organic molecule or an antibody.

13. The method of claim 12, wherein the small organic molecule comprises SU5402, TK1258, PD173074, imatinib, or a combination of two or more thereof.

14. The method of claim 12, wherein the antibody comprises a monoclonal antibody.

15. The method of claim 1, wherein the treatment with an inhibitor of FGFR4 is administered as an adjuvant therapy with standard anti-cancer therapy.

16. The method of claim 1, further comprising determining whether the tumor sample has altered expression of the at least one variant FGFR4 protein or nucleic acid relative to a control sample.

17. The method of claim 16, wherein the tumor sample comprises a rhabdomyosarcoma.

18. The method of claim 16, wherein FGFR4 expression is determined by quantitative real-time PCR, Western blotting, ELISA, or immunohistochemistry.

* * * * *

SEQUENCE LISTING

```
<160> NUMBER OF SEQ ID NOS: 49

<210> SEQ ID NO 1
<211> LENGTH: 3084
<212> TYPE: DNA
<213> ORGANISM: Homo sapiens
<220> FEATURE:
<221> NAME/KEY: CDS
<222> LOCATION: (212)..(2620)

<400> SEQUENCE: 1
ctcgctcccg gccgaggagc gctcgggctg tctgcggacc ctgccgcgtg cagggcgtcgc      60 ggccggctgg agctgggagt gaggcggcgg aggagccagg tgaggaggag ccaggtgagc     120
aggaccctgt gctgggcgcg gagtcacgca ggctcgagga aggcagttgg tgggaagtcc     180
agcttgggtc cctgagagct gtgagaagga g atg cgg ctg ctg ctg gcc ctg        232
                                  Met Arg Leu Leu Leu Ala Leu
                                    1               5 ttg ggg gtc ctg ctg agt gtg cct ggg cct cca gtc ttg tcc ctg gag        280
Leu Gly Val Leu Leu Ser Val Pro Gly Pro Pro Val Leu Ser Leu Glu
         10                  15                  20 gcc tct gag gaa gtg gag ctt gag ccc tgc ctg gct ccc agc ctg gag        328
Ala Ser Glu Glu Val Glu Leu Glu Pro Cys Leu Ala Pro Ser Leu Glu
     25                  30                  35 cag caa gag cag gag ctg aca gta gcc ctt ggg cag cct gtg cgt ctg        376
Gln Gln Glu Gln Glu Leu Thr Val Ala Leu Gly Gln Pro Val Arg Leu
40                  45                  50                  55 tgc tgt ggg cgg gct gag cgt ggt ggc cac tgg tac aag gag ggc agt        424
Cys Cys Gly Arg Ala Glu Arg Gly Gly His Trp Tyr Lys Glu Gly Ser
                 60                  65                  70 cgc ctg gca cct gct ggc cgt gta cgg ggc tgg agg ggc cgc cta gag        472
Arg Leu Ala Pro Ala Gly Arg Val Arg Gly Trp Arg Gly Arg Leu Glu
             75                  80                  85 att gcc agc ttc cta cct gag gat gct ggc cgc tac ctc tgc ctg gca        520
Ile Ala Ser Phe Leu Pro Glu Asp Ala Gly Arg Tyr Leu Cys Leu Ala
         90                  95                 100 cga ggc tcc atg atc gtc ctg cag aat ctc acc ttg att aca ggt gac        568
```

```
Arg Gly Ser Met Ile Val Leu Gln Asn Leu Thr Leu Ile Thr Gly Asp
    105                 110                 115 tcc ttg acc tcc agc aac gat gat gag gac ccc aag tcc cat agg gac    616
Ser Leu Thr Ser Ser Asn Asp Asp Glu Asp Pro Lys Ser His Arg Asp
120                 125                 130                 135 ccc tcg aat agg cac agt tac ccc cag caa gca ccc tac tgg aca cac    664
Pro Ser Asn Arg His Ser Tyr Pro Gln Gln Ala Pro Tyr Trp Thr His
            140                 145                 150 ccc cag cgc atg gag aag aaa ctg cat gca gta cct gcg ggg aac acc    712
Pro Gln Arg Met Glu Lys Lys Leu His Ala Val Pro Ala Gly Asn Thr
                155                 160                 165 gtc aag ttc cgc tgt cca gct gca ggc aac ccc acg ccc acc atc cgc    760
Val Lys Phe Arg Cys Pro Ala Ala Gly Asn Pro Thr Pro Thr Ile Arg
        170                 175                 180 tgg ctt aag gat gga cag gcc ttt cat ggg gag aac cgc att gga ggc    808
Trp Leu Lys Asp Gly Gln Ala Phe His Gly Glu Asn Arg Ile Gly Gly
    185                 190                 195 att cgg ctg cgc cat cag cac tgg agt ctc gtg atg gag agc gtg gtg    856
Ile Arg Leu Arg His Gln His Trp Ser Leu Val Met Glu Ser Val Val
200                 205                 210                 215 ccc tcg gac cgc ggc aca tac acc tgc ctg gta gag aac gct gtg ggc    904
Pro Ser Asp Arg Gly Thr Tyr Thr Cys Leu Val Glu Asn Ala Val Gly
            220                 225                 230 agc atc cgc tat aac tac ctg cta gat gtg ctg gag cgg tcc ccg cac    952
Ser Ile Arg Tyr Asn Tyr Leu Leu Asp Val Leu Glu Arg Ser Pro His
                235                 240                 245 cgg ccc atc ctg cag gcc ggg ctc ccg gcc aac acc aca gcc gtg gtg    1000
Arg Pro Ile Leu Gln Ala Gly Leu Pro Ala Asn Thr Thr Ala Val Val
        250                 255                 260 ggc agc gac gtg gag ctg ctg tgc aag gtg tac agc gat gcc cag ccc    1048
Gly Ser Asp Val Glu Leu Leu Cys Lys Val Tyr Ser Asp Ala Gln Pro
    265                 270                 275 cac atc cag tgg ctg aag cac atc gtc atc aac ggc agc agc ttc gga    1096
His Ile Gln Trp Leu Lys His Ile Val Ile Asn Gly Ser Ser Phe Gly
280                 285                 290                 295 gcc gac ggt ttc ccc tat gtg caa gtc cta aag act gca gac atc aat    1144
Ala Asp Gly Phe Pro Tyr Val Gln Val Leu Lys Thr Ala Asp Ile Asn
            300                 305                 310 agc tca gag gtg gag gtc ctg tac ctg cgg aac gtg tca gcc gag gac    1192
Ser Ser Glu Val Glu Val Leu Tyr Leu Arg Asn Val Ser Ala Glu Asp
                315                 320                 325 gca ggc gag tac acc tgc ctc gca ggc aat tcc atc ggc ctc tcc tac    1240
Ala Gly Glu Tyr Thr Cys Leu Ala Gly Asn Ser Ile Gly Leu Ser Tyr
        330                 335                 340 cag tct gcc tgg ctc acg gtg ctg cca gag gag gac ccc aca tgg acc    1288
Gln Ser Ala Trp Leu Thr Val Leu Pro Glu Glu Asp Pro Thr Trp Thr
    345                 350                 355 gca gca gcg ccc gag gcc agg tat acg gac atc atc ctg tac gcg tcg    1336
Ala Ala Ala Pro Glu Ala Arg Tyr Thr Asp Ile Ile Leu Tyr Ala Ser
360                 365                 370                 375 ggc tcc ctg gcc ttg gct gtg ctc ctg ctg gcc ggg ctg tat cga        1384
Gly Ser Leu Ala Leu Ala Val Leu Leu Leu Ala Gly Leu Tyr Arg
            380                 385                 390 ggg cag gcg ctc cac ggc cgg cac ccc cgc ccg ccc gcc act gtg cag    1432
Gly Gln Ala Leu His Gly Arg His Pro Arg Pro Pro Ala Thr Val Gln
                395                 400                 405 aag ctc tcc cgc ttc cct ctg gcc cga cag ttc tcc ctg gag tca ggc    1480
Lys Leu Ser Arg Phe Pro Leu Ala Arg Gln Phe Ser Leu Glu Ser Gly
        410                 415                 420 tct tcc ggc aag tca agc tca tcc ctg gta cga ggc gtg cgt ctc tcc    1528
```

-continued

```
Ser Ser Gly Lys Ser Ser Ser Leu Val Arg Gly Val Arg Leu Ser
    425                 430                 435 tcc agc ggc ccc gcc ttg ctc gcc ggc ctc gtg agt cta gat cta cct      1576
Ser Ser Gly Pro Ala Leu Leu Ala Gly Leu Val Ser Leu Asp Leu Pro
440                 445                 450                 455 ctc gac cca cta tgg gag ttc ccc cgg gac agg ctg gtg ctt ggg aag      1624
Leu Asp Pro Leu Trp Glu Phe Pro Arg Asp Arg Leu Val Leu Gly Lys
                460                 465                 470 ccc cta ggc gag ggc tgc ttt ggc cag gta gta cgt gca gag gcc ttt      1672
Pro Leu Gly Glu Gly Cys Phe Gly Gln Val Val Arg Ala Glu Ala Phe
            475                 480                 485 ggc atg gac cct gcc cgg cct gac caa gcc agc act gtg gcc gtc aag      1720
Gly Met Asp Pro Ala Arg Pro Asp Gln Ala Ser Thr Val Ala Val Lys
        490                 495                 500 atg ctc aaa gac aac gcc tct gac aag gac ctg gcc gac ctg gtc tcg      1768
Met Leu Lys Asp Asn Ala Ser Asp Lys Asp Leu Ala Asp Leu Val Ser
    505                 510                 515 gag atg gag gtg atg aag ctg atc ggc cga cac aag aac atc atc aac      1816
Glu Met Glu Val Met Lys Leu Ile Gly Arg His Lys Asn Ile Ile Asn
520                 525                 530                 535 ctg ctt ggt gtc tgc acc cag gaa ggg ccc ctg tac gtg atc gtg gag      1864
Leu Leu Gly Val Cys Thr Gln Glu Gly Pro Leu Tyr Val Ile Val Glu
                540                 545                 550 tgc gcc gcc aag gga aac ctg cgg gag ttc ctg cgg gcc cgg cgc ccc      1912
Cys Ala Ala Lys Gly Asn Leu Arg Glu Phe Leu Arg Ala Arg Arg Pro
            555                 560                 565 cca ggc ccc gac ctc agc ccc gac ggt cct cgg agc agt gag ggg ccg      1960
Pro Gly Pro Asp Leu Ser Pro Asp Gly Pro Arg Ser Ser Glu Gly Pro
        570                 575                 580 ctc tcc ttc cca gtc ctg gtc tcc tgc gcc tac cag gtg gcc cga ggc      2008
Leu Ser Phe Pro Val Leu Val Ser Cys Ala Tyr Gln Val Ala Arg Gly
    585                 590                 595 atg cag tat ctg gag tcc cgg aag tgt atc cac cgg gac ctg gct gcc      2056
Met Gln Tyr Leu Glu Ser Arg Lys Cys Ile His Arg Asp Leu Ala Ala
600                 605                 610                 615 cgc aat gtg ctg gtg act gag gac aat gtg atg aag att gct gac ttt      2104
Arg Asn Val Leu Val Thr Glu Asp Asn Val Met Lys Ile Ala Asp Phe
                620                 625                 630 ggg ctg gcc cgc ggc gtc cac cac att gac tac tat aag aaa acc agc      2152
Gly Leu Ala Arg Gly Val His His Ile Asp Tyr Tyr Lys Lys Thr Ser
            635                 640                 645 aac ggc cgc ctg cct gtg aag tgg atg gcg ccc gag gcc ttg ttt gac      2200
Asn Gly Arg Leu Pro Val Lys Trp Met Ala Pro Glu Ala Leu Phe Asp
        650                 655                 660 cgg gtg tac aca cac cag agt gac gtg tgg tct ttt ggg atc ctg cta      2248
Arg Val Tyr Thr His Gln Ser Asp Val Trp Ser Phe Gly Ile Leu Leu
    665                 670                 675 tgg gag atc ttc acc ctc ggg ggc tcc ccg tat cct ggc atc ccg gtg      2296
Trp Glu Ile Phe Thr Leu Gly Gly Ser Pro Tyr Pro Gly Ile Pro Val
680                 685                 690                 695 gag gag ctg ttc tcg ctg ctg cgg gag gga cat cgg atg gac cga ccc      2344
Glu Glu Leu Phe Ser Leu Leu Arg Glu Gly His Arg Met Asp Arg Pro
                700                 705                 710 cca cac tgc ccc cca gag ctg tac ggg ctg atg cgt gag tgc tgg cac      2392
Pro His Cys Pro Pro Glu Leu Tyr Gly Leu Met Arg Glu Cys Trp His
            715                 720                 725 gca gcg ccc tcc cag agg cct acc ttc aag cag ctg gtg gag gcg ctg      2440
Ala Ala Pro Ser Gln Arg Pro Thr Phe Lys Gln Leu Val Glu Ala Leu
        730                 735                 740 gac aag gtc ctg ctg gcc gtc tct gag gag tac ctc gac ctc cgc ctg      2488
```

-continued

```
Asp Lys Val Leu Leu Ala Val Ser Glu Glu Tyr Leu Asp Leu Arg Leu
        745                 750                 755 acc ttc gga ccc tat tcc ccc tct ggt ggg gac gcc agc agc acc tgc    2536
Thr Phe Gly Pro Tyr Ser Pro Ser Gly Gly Asp Ala Ser Ser Thr Cys
760                 765                 770                 775 tcc tcc agc gat tct gtc ttc agc cac gac ccc ctg cca ttg gga tcc    2584
Ser Ser Ser Asp Ser Val Phe Ser His Asp Pro Leu Pro Leu Gly Ser
                780                 785                 790 agc tcc ttc ccc ttc ggg tct ggg gtg cag aca tga gcaaggctca         2630
Ser Ser Phe Pro Phe Gly Ser Gly Val Gln Thr
                795                 800 aggctgtgca ggcacatagg ctggtggcct tgggccttgg ggctcagcca cagcctgaca   2690
cagtgctcga ccttgatagc atggggcccc tgggcccagag ttgctgtgcc gtgtccaagg  2750
gccgtgccct tgcccttgga gctgccgtgc ctgtgtcctg atggcccaaa tgtcagggtt   2810
ctgctcggct tcttggacct tggcgcttag tccccatccc gggtttggct gagcctggct   2870
ggagagctgc tatgctaaac ctcctgcctc ccaataccag caggaggttc tgggcctctg   2930
aacccccttt ccccacacct ccccctgctg ctgctgcccc agcgtcttga cgggagcatt   2990 ggccccctgag cccagagaag ctggaagcct gccgaaaaca ggagcaaatg gcgttttata  3050
aattattttt ttgaaataaa aaaaaaaaa aaaa                                3084
```

<210> SEQ ID NO 2
<211> LENGTH: 802
<212> TYPE: PRT
<213> ORGANISM: Homo sapiens

<400> SEQUENCE: 2

```
Met Arg Leu Leu Leu Ala Leu Leu Gly Val Leu Leu Ser Val Pro Gly
1               5                   10                  15

Pro Pro Val Leu Ser Leu Glu Ala Ser Glu Glu Val Glu Leu Glu Pro
            20                  25                  30

Cys Leu Ala Pro Ser Leu Glu Gln Gln Glu Gln Glu Leu Thr Val Ala
        35                  40                  45

Leu Gly Gln Pro Val Arg Leu Cys Cys Gly Arg Ala Glu Arg Gly Gly
    50                  55                  60

His Trp Tyr Lys Glu Gly Ser Arg Leu Ala Pro Ala Gly Arg Val Arg
65                  70                  75                  80

Gly Trp Arg Gly Arg Leu Glu Ile Ala Ser Phe Leu Pro Glu Asp Ala
                85                  90                  95

Gly Arg Tyr Leu Cys Leu Ala Arg Gly Ser Met Ile Val Leu Gln Asn
            100                 105                 110

Leu Thr Leu Ile Thr Gly Asp Ser Leu Thr Ser Ser Asn Asp Asp Glu
        115                 120                 125

Asp Pro Lys Ser His Arg Asp Pro Ser Asn Arg His Ser Tyr Pro Gln
    130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Pro Thr Pro Thr Ile Arg Trp Leu Lys Asp Gly Gln Ala Phe His
            180                 185                 190

Gly Glu Asn Arg Ile Gly Gly Ile Arg Leu Arg His Gln His Trp Ser
        195                 200                 205

Leu Val Met Glu Ser Val Val Pro Ser Asp Arg Gly Thr Tyr Thr Cys
    210                 215                 220
```

```
Leu Val Glu Asn Ala Val Gly Ser Ile Arg Tyr Asn Tyr Leu Leu Asp
225                 230                 235                 240

Val Leu Glu Arg Ser Pro His Arg Pro Ile Leu Gln Ala Gly Leu Pro
            245                 250                 255

Ala Asn Thr Thr Ala Val Val Gly Ser Asp Val Glu Leu Leu Cys Lys
                260                 265                 270

Val Tyr Ser Asp Ala Gln Pro His Ile Gln Trp Leu Lys His Ile Val
            275                 280                 285

Ile Asn Gly Ser Ser Phe Gly Ala Asp Gly Phe Pro Tyr Val Gln Val
            290                 295                 300

Leu Lys Thr Ala Asp Ile Asn Ser Ser Glu Val Glu Val Leu Tyr Leu
305                 310                 315                 320

Arg Asn Val Ser Ala Glu Asp Ala Gly Glu Tyr Thr Cys Leu Ala Gly
                325                 330                 335

Asn Ser Ile Gly Leu Ser Tyr Gln Ser Ala Trp Leu Thr Val Leu Pro
            340                 345                 350

Glu Glu Asp Pro Thr Trp Thr Ala Ala Pro Glu Ala Arg Tyr Thr
            355                 360                 365

Asp Ile Ile Leu Tyr Ala Ser Gly Ser Leu Ala Leu Ala Val Leu Leu
370                 375                 380

Leu Leu Ala Gly Leu Tyr Arg Gly Gln Ala Leu His Gly Arg His Pro
385                 390                 395                 400

Arg Pro Pro Ala Thr Val Gln Lys Leu Ser Arg Phe Pro Leu Ala Arg
                405                 410                 415

Gln Phe Ser Leu Glu Ser Gly Ser Ser Gly Lys Ser Ser Ser Ser Leu
            420                 425                 430

Val Arg Gly Val Arg Leu Ser Ser Ser Gly Pro Ala Leu Leu Ala Gly
            435                 440                 445

Leu Val Ser Leu Asp Leu Pro Leu Asp Pro Leu Trp Glu Phe Pro Arg
450                 455                 460

Asp Arg Leu Val Leu Gly Lys Pro Leu Gly Glu Gly Cys Phe Gly Gln
465                 470                 475                 480

Val Val Arg Ala Glu Ala Phe Gly Met Asp Pro Ala Arg Pro Asp Gln
                485                 490                 495

Ala Ser Thr Val Ala Val Lys Met Leu Lys Asp Asn Ala Ser Asp Lys
            500                 505                 510

Asp Leu Ala Asp Leu Val Ser Glu Met Glu Val Met Lys Leu Ile Gly
            515                 520                 525

Arg His Lys Asn Ile Ile Asn Leu Leu Gly Val Cys Thr Gln Glu Gly
            530                 535                 540

Pro Leu Tyr Val Ile Val Glu Cys Ala Ala Lys Gly Asn Leu Arg Glu
545                 550                 555                 560

Phe Leu Arg Ala Arg Arg Pro Pro Gly Pro Asp Leu Ser Pro Asp Gly
                565                 570                 575

Pro Arg Ser Ser Glu Gly Pro Leu Ser Phe Pro Val Leu Val Ser Cys
            580                 585                 590

Ala Tyr Gln Val Ala Arg Gly Met Gln Tyr Leu Glu Ser Arg Lys Cys
            595                 600                 605

Ile His Arg Asp Leu Ala Ala Arg Asn Val Leu Val Thr Glu Asp Asn
            610                 615                 620

Val Met Lys Ile Ala Asp Phe Gly Leu Ala Arg Gly Val His His Ile
625                 630                 635                 640

Asp Tyr Tyr Lys Lys Thr Ser Asn Gly Arg Leu Pro Val Lys Trp Met
```

-continued

```
                        645                 650                 655
Ala Pro Glu Ala Leu Phe Asp Arg Val Tyr Thr His Gln Ser Asp Val
            660                 665                 670

Trp Ser Phe Gly Ile Leu Leu Trp Glu Ile Phe Thr Leu Gly Gly Ser
        675                 680                 685

Pro Tyr Pro Gly Ile Pro Val Glu Glu Leu Phe Ser Leu Leu Arg Glu
    690                 695                 700

Gly His Arg Met Asp Arg Pro Pro His Cys Pro Pro Glu Leu Tyr Gly
705                 710                 715                 720

Leu Met Arg Glu Cys Trp His Ala Ala Pro Ser Gln Arg Pro Thr Phe
                725                 730                 735

Lys Gln Leu Val Glu Ala Leu Asp Lys Val Leu Leu Ala Val Ser Glu
            740                 745                 750

Glu Tyr Leu Asp Leu Arg Leu Thr Phe Gly Pro Tyr Ser Pro Ser Gly
        755                 760                 765

Gly Asp Ala Ser Ser Thr Cys Ser Ser Ser Asp Ser Val Phe Ser His
    770                 775                 780

Asp Pro Leu Pro Leu Gly Ser Ser Ser Phe Pro Phe Gly Ser Gly Val
785                 790                 795                 800

Gln Thr

<210> SEQ ID NO 3
<211> LENGTH: 41
<212> TYPE: DNA
<213> ORGANISM: Artificial sequence
<220> FEATURE:
<223> OTHER INFORMATION: Synthetic oligonucleotide primer FGFR4 exon 2
      forward

<400> SEQUENCE: 3
tgtaaaacga cggccagtgg ccacttcctg tctcagtttc c                    41

<210> SEQ ID NO 4
<211> LENGTH: 40
<212> TYPE: DNA
<213> ORGANISM: Artificial sequence
<220> FEATURE:
<223> OTHER INFORMATION: Synthetic oligonucleotide primer FGFR4 exon 2
      reverse

<400> SEQUENCE: 4
caggaaacag ctatgaccct gggcaaggat cctttccagc                      40

<210> SEQ ID NO 5
<211> LENGTH: 40
<212> TYPE: DNA
<213> ORGANISM: Artificial sequence
<220> FEATURE:
<223> OTHER INFORMATION: Synthetic oligonucleotide primer FGFR4 exon 3
      forward

<400> SEQUENCE: 5
tgtaaaacga cggccagtgg tcaaggagtc tacatcaggg                      40

<210> SEQ ID NO 6
<211> LENGTH: 39
<212> TYPE: DNA
<213> ORGANISM: Artificial sequence
<220> FEATURE:
<223> OTHER INFORMATION: Synthetic oligonucleotide primer FGFR4 exon 3
      reverse

<400> SEQUENCE: 6
```
caggaaacag ctatgacccc ttcagcatgc gttgcaaag					39

<210> SEQ ID NO 7
<211> LENGTH: 38
<212> TYPE: DNA
<213> ORGANISM: Artificial sequence
<220> FEATURE:
<223> OTHER INFORMATION: Synthetic oligonucleotide primer FGFR4 exon 4
      forward

<400> SEQUENCE: 7
tgtaaaacga cggccagtct caccttgatt acaggtgg					38

<210> SEQ ID NO 8
<211> LENGTH: 37
<212> TYPE: DNA
<213> ORGANISM: Artificial sequence
<220> FEATURE:
<223> OTHER INFORMATION: Synthetic oligonucleotide primer FGFR4 exon 4
      reverse

<400> SEQUENCE: 8
caggaaacag ctatgaccgt ttcttctcca tgcgctg					37

<210> SEQ ID NO 9
<211> LENGTH: 36
<212> TYPE: DNA
<213> ORGANISM: Artificial sequence
<220> FEATURE:
<223> OTHER INFORMATION: Synthetic oligonucleotide primer FGFR4 exon 5
      forward

<400> SEQUENCE: 9
tgtaaaacga cggccagtca gtaggtctcc aaggac					36

<210> SEQ ID NO 10
<211> LENGTH: 40
<212> TYPE: DNA
<213> ORGANISM: Artificial sequence
<220> FEATURE:
<223> OTHER INFORMATION: Synthetic oligonucleotide primer FGFR4 exon 5
      reverse

<400> SEQUENCE: 10
caggaaacag ctatgacccc gcaatcgctt cactcattcg					40

<210> SEQ ID NO 11
<211> LENGTH: 37
<212> TYPE: DNA
<213> ORGANISM: Artificial sequence
<220> FEATURE:
<223> OTHER INFORMATION: Synthetic oligonucleotide primer FGFR4 exon 6
      forward

<400> SEQUENCE: 11
tgtaaaacga cggccagtgt tctcagggcc tagagag					37

<210> SEQ ID NO 12
<211> LENGTH: 38
<212> TYPE: DNA
<213> ORGANISM: Artificial sequence
<220> FEATURE:
<223> OTHER INFORMATION: Synthetic oligonucleotide primer FGFR4 exon 6
      reverse

<400> SEQUENCE: 12
caggaaacag ctatgaccct caccaagctg cctgactc					38

<210> SEQ ID NO 13
<211> LENGTH: 39
<212> TYPE: DNA
<213> ORGANISM: Artificial sequence
<220> FEATURE:
<223> OTHER INFORMATION: Synthetic oligonucleotide primer FGFR4 exon 7
      forward

<400> SEQUENCE: 13
tgtaaaacga cggccagtga gacagacaag aagctgcag                              39

<210> SEQ ID NO 14
<211> LENGTH: 40
<212> TYPE: DNA
<213> ORGANISM: Artificial sequence
<220> FEATURE:
<223> OTHER INFORMATION: Synthetic oligonucleotide primer FGFR4 exon 7
      reverse

<400> SEQUENCE: 14
caggaaacag ctatgacccc acctctgagc tattgatgtc                             40

<210> SEQ ID NO 15
<211> LENGTH: 38
<212> TYPE: DNA
<213> ORGANISM: Artificial sequence
<220> FEATURE:
<223> OTHER INFORMATION: Synthetic oligonucleotide primer FGFR4 exon 8
      forward

<400> SEQUENCE: 15
tgtaaaacga cggccagtca ttcttctccc accttggg                               38

<210> SEQ ID NO 16
<211> LENGTH: 37
<212> TYPE: DNA
<213> ORGANISM: Artificial sequence
<220> FEATURE:
<223> OTHER INFORMATION: Synthetic oligonucleotide primer FGFR4 exon 8
      reverse

<400> SEQUENCE: 16
caggaaacag ctatgacccc cacaaatcca cacactg                                37

<210> SEQ ID NO 17
<211> LENGTH: 38
<212> TYPE: DNA
<213> ORGANISM: Artificial sequence
<220> FEATURE:
<223> OTHER INFORMATION: Synthetic oligonucleotide primer FGFR4 exon
      9_10 forward

<400> SEQUENCE: 17
tgtaaaacga cggccagtgc tgggagggac tgagttag                               38

<210> SEQ ID NO 18
<211> LENGTH: 38
<212> TYPE: DNA
<213> ORGANISM: Artificial sequence
<220> FEATURE:
<223> OTHER INFORMATION: Synthetic oligonucleotide primer FGFR4 exon
      9_10 reverse

<400> SEQUENCE: 18
caggaaacag ctatgacctg gagaaagtcc agcctcag                               38

```
<210> SEQ ID NO 19
<211> LENGTH: 38
<212> TYPE: DNA
<213> ORGANISM: Artificial sequence
<220> FEATURE:
<223> OTHER INFORMATION: Synthetic oligonucleotide primer FGFR4 exon 11
      forward

<400> SEQUENCE: 19
tgtaaaacga cggccagtct acctctcgac ccactatg                           38

<210> SEQ ID NO 20
<211> LENGTH: 38
<212> TYPE: DNA
<213> ORGANISM: Artificial sequence
<220> FEATURE:
<223> OTHER INFORMATION: Synthetic oligonucleotide primer FGFR4 exon 11
      reverse

<400> SEQUENCE: 20
caggaaacag ctatgaccgt cttgccatgt tgcccagg                           38

<210> SEQ ID NO 21
<211> LENGTH: 38
<212> TYPE: DNA
<213> ORGANISM: Artificial sequence
<220> FEATURE:
<223> OTHER INFORMATION: Synthetic oligonucleotide primer FGFR4 exon 12
      forward

<400> SEQUENCE: 21
tgtaaaacga cggccagtga ttcagcccta gacctacg                           38

<210> SEQ ID NO 22
<211> LENGTH: 36
<212> TYPE: DNA
<213> ORGANISM: Artificial sequence
<220> FEATURE:
<223> OTHER INFORMATION: Synthetic oligonucleotide primer FGFR4 exon 12
      reverse

<400> SEQUENCE: 22
caggaaacag ctatgaccca ctccacgatc acgtac                             36

<210> SEQ ID NO 23
<211> LENGTH: 36
<212> TYPE: DNA
<213> ORGANISM: Artificial sequence
<220> FEATURE:
<223> OTHER INFORMATION: Synthetic oligonucleotide primer FGFR4 exon 13
      forward

<400> SEQUENCE: 23
tgtaaaacga cggccagtca acctgcttgg tgtctg                             36

<210> SEQ ID NO 24
<211> LENGTH: 36
<212> TYPE: DNA
<213> ORGANISM: Artificial sequence
<220> FEATURE:
<223> OTHER INFORMATION: Synthetic oligonucleotide primer FGFR4 exon 13
      reverse

<400> SEQUENCE: 24
caggaaacag ctatgaccgg aaagcgtgaa tgcctg                             36

<210> SEQ ID NO 25
<211> LENGTH: 41
```

```
<212> TYPE: DNA
<213> ORGANISM: Artificial sequence
<220> FEATURE:
<223> OTHER INFORMATION: Synthetic oligonucleotide primer FGFR4 exon 14
      forward

<400> SEQUENCE: 25
tgtaaaacga cggccagtct aacccttgac ctcctcctct g                    41

<210> SEQ ID NO 26
<211> LENGTH: 36
<212> TYPE: DNA
<213> ORGANISM: Artificial sequence
<220> FEATURE:
<223> OTHER INFORMATION: Synthetic oligonucleotide primer FGFR4 exon 14
      reverse

<400> SEQUENCE: 26
caggaaacag ctatgaccca tccacttcac aggcag                          36

<210> SEQ ID NO 27
<211> LENGTH: 38
<212> TYPE: DNA
<213> ORGANISM: Artificial sequence
<220> FEATURE:
<223> OTHER INFORMATION: Synthetic oligonucleotide primer FGFR4 exon 15
      forward

<400> SEQUENCE: 27
tgtaaaacga cggccagtcc agcaacgtga gggagatg                        38

<210> SEQ ID NO 28
<211> LENGTH: 39
<212> TYPE: DNA
<213> ORGANISM: Artificial sequence
<220> FEATURE:
<223> OTHER INFORMATION: Synthetic oligonucleotide primer FGFR4 exon 15
      reverse

<400> SEQUENCE: 28
caggaaacag ctatgacccc aaatctgaag gagccctcg                       39

<210> SEQ ID NO 29
<211> LENGTH: 39
<212> TYPE: DNA
<213> ORGANISM: Artificial sequence
<220> FEATURE:
<223> OTHER INFORMATION: Synthetic oligonucleotide primer FGFR4 exon 16
      forward

<400> SEQUENCE: 29
tgtaaaacga cggccagtgg ctccttcaga tttggtctg                       39

<210> SEQ ID NO 30
<211> LENGTH: 39
<212> TYPE: DNA
<213> ORGANISM: Artificial sequence
<220> FEATURE:
<223> OTHER INFORMATION: Synthetic oligonucleotide primer FGFR4 exon 16
      reverse

<400> SEQUENCE: 30
caggaaacag ctatgaccgt tagtgttgtc cttctggcc                       39

<210> SEQ ID NO 31
<211> LENGTH: 38
<212> TYPE: DNA
<213> ORGANISM: Artificial sequence
```

```
<220> FEATURE:
<223> OTHER INFORMATION: Synthetic oligonucleotide primer FGFR4 exon 17
      forward

<400> SEQUENCE: 31
tgtaaaacga cggccagtct actgatgacc ctcctatc                             38

<210> SEQ ID NO 32
<211> LENGTH: 38
<212> TYPE: DNA
<213> ORGANISM: Artificial sequence
<220> FEATURE:
<223> OTHER INFORMATION: Synthetic oligonucleotide primer FGFR4 exon 17
      reverse

<400> SEQUENCE: 32
caggaaacag ctatgaccga atagggtccg aaggtcag                             38

<210> SEQ ID NO 33
<211> LENGTH: 37
<212> TYPE: DNA
<213> ORGANISM: Artificial sequence
<220> FEATURE:
<223> OTHER INFORMATION: Synthetic oligonucleotide primer FGFR4 exon 18
      forward

<400> SEQUENCE: 33
tgtaaaacga cggccagtgt ctctgaggag gtacagc                              37

<210> SEQ ID NO 34
<211> LENGTH: 38
<212> TYPE: DNA
<213> ORGANISM: Artificial sequence
<220> FEATURE:
<223> OTHER INFORMATION: Synthetic oligonucleotide primer FGFR4 exon 18
      reverse

<400> SEQUENCE: 34
caggaaacag ctatgaccga cacggcacag caactctg                             38

<210> SEQ ID NO 35
<211> LENGTH: 18
<212> TYPE: DNA
<213> ORGANISM: Artificial sequence
<220> FEATURE:
<223> OTHER INFORMATION: Synthetic oligonucleotide primer M13 forward

<400> SEQUENCE: 35
tgtaaaacga cggccagt                                                   18

<210> SEQ ID NO 36
<211> LENGTH: 18
<212> TYPE: DNA
<213> ORGANISM: Artificial sequence
<220> FEATURE:
<223> OTHER INFORMATION: Synthetic oligonucleotide primer M13 reverse

<400> SEQUENCE: 36
caggaaacag ctatgacc                                                   18

<210> SEQ ID NO 37
<211> LENGTH: 23
<212> TYPE: DNA
<213> ORGANISM: Artificial sequence
<220> FEATURE:
<223> OTHER INFORMATION: Synthetic oligonucleotide primer 3' FOXO1

<400> SEQUENCE: 37
```

-continued atgaacttgc tgtgtaggga cag                              23

<210> SEQ ID NO 38
<211> LENGTH: 24
<212> TYPE: DNA
<213> ORGANISM: Artificial sequence
<220> FEATURE:
<223> OTHER INFORMATION: Synthetic oligonucleotide primer FGFR4 exon
      9/10 forward

<400> SEQUENCE: 38
ttgtctgtct gtgtgtgtcc atgt                             24

<210> SEQ ID NO 39
<211> LENGTH: 24
<212> TYPE: DNA
<213> ORGANISM: Artificial sequence
<220> FEATURE:
<223> OTHER INFORMATION: Synthetic oligonucleotide primer FGFR4 exon
      9/10 reverse

<400> SEQUENCE: 39
cgtacaggat gatgtccgta tacc                             24

<210> SEQ ID NO 40
<211> LENGTH: 18
<212> TYPE: DNA
<213> ORGANISM: Artificial sequence
<220> FEATURE:
<223> OTHER INFORMATION: Synthetic oligonucleotide probe FGFR4 exon 9/10

<400> SEQUENCE: 40
cagaggagga ccccacat                                    18

<210> SEQ ID NO 41
<211> LENGTH: 17
<212> TYPE: DNA
<213> ORGANISM: Artificial sequence
<220> FEATURE:
<223> OTHER INFORMATION: Synthetic oligonucleotide primer FGFR4 exon 3/4
      forward

<400> SEQUENCE: 41
tgtggcatcc gcagcat                                     17

<210> SEQ ID NO 42
<211> LENGTH: 21
<212> TYPE: DNA
<213> ORGANISM: Artificial sequence
<220> FEATURE:
<223> OTHER INFORMATION: Synthetic oligonucleotide primer FGFR4 exon 3/4
      reverse

<400> SEQUENCE: 42
ctgaggcagc ctcctgtgta c                                21

<210> SEQ ID NO 43
<211> LENGTH: 16
<212> TYPE: DNA
<213> ORGANISM: Artificial sequence
<220> FEATURE:
<223> OTHER INFORMATION: Synthetic oligonucleotide probe FGFR4 exon 3/4

<400> SEQUENCE: 43
atgtgcggtg tgttct                                      16

<210> SEQ ID NO 44
<211> LENGTH: 62
<212> TYPE: DNA
<213> ORGANISM: Artificial sequence
<220> FEATURE:
<223> OTHER INFORMATION: Synthetic oligonucleotide shRNA FGFR4

<400> SEQUENCE: 44
agctaaaaag ccgtcaagat gctcaaagac tctcttgaag tctttgagca tcttgacggc    60
gg                                                                  62

<210> SEQ ID NO 45
<211> LENGTH: 36
<212> TYPE: PRT
<213> ORGANISM: Artificial sequence
<220> FEATURE:
<223> OTHER INFORMATION: Hypothetical peptide FGFR4 amino acids 524-559

<400> SEQUENCE: 45

Met Lys Leu Ile Gly Arg His Lys Asn Ile Ile Asn Leu Leu Gly Val
 1               5                  10                  15

Cys Thr Gln Glu Gly Pro Leu Tyr Val Ile Val Glu Cys Ala Ala Lys
             20                  25                  30

Gly Asn Leu Arg
         35

<210> SEQ ID NO 46
<211> LENGTH: 36
<212> TYPE: PRT
<213> ORGANISM: Artificial sequence
<220> FEATURE:
<223> OTHER INFORMATION: Hypothetical peptide FGFR1 amino acids 535-570

<400> SEQUENCE: 46

Met Lys Met Ile Gly Lys His Lys Asn Ile Ile Asn Leu Leu Gly Ala
 1               5                  10                  15

Cys Thr Gln Asp Gly Pro Leu Tyr Val Ile Val Glu Tyr Ala Ser Lys
             20                  25                  30

Gly Asn Leu Arg
         35

<210> SEQ ID NO 47
<211> LENGTH: 36
<212> TYPE: PRT
<213> ORGANISM: Artificial sequence
<220> FEATURE:
<223> OTHER INFORMATION: Hypothetical peptide FGFR2 amino acids 538-573

<400> SEQUENCE: 47

Met Lys Met Ile Gly Lys His Lys Asn Ile Ile Asn Leu Leu Gly Ala
 1               5                  10                  15

Cys Thr Gln Asp Gly Pro Leu Tyr Val Ile Val Glu Tyr Ala Ser Lys
             20                  25                  30

Gly Asn Leu Arg
         35

<210> SEQ ID NO 48
<211> LENGTH: 36
<212> TYPE: PRT
<213> ORGANISM: Artificial sequence
<220> FEATURE:
<223> OTHER INFORMATION: Hypothetical peptide FGFR3 amino acids 529-564

<400> SEQUENCE: 48

```
Met Lys Met Ile Gly Lys His Lys Asn Ile Ile Asn Leu Leu Gly Ala
1               5                   10                  15

Cys Thr Gln Gly Gly Pro Leu Tyr Val Leu Val Glu Tyr Ala Ala Lys
            20                  25                  30

Gly Asn Leu Arg
        35

<210> SEQ ID NO 49
<211> LENGTH: 35
<212> TYPE: PRT
<213> ORGANISM: Artificial sequence
<220> FEATURE:
<223> OTHER INFORMATION: Hypothetical peptide RET amino acids 778-813

<400> SEQUENCE: 49

Leu Lys Gln Val Asn His Pro His Val Ile Lys Leu Tyr Gly Ala Cys
1               5                   10                  15

Ser Gln Asp Gly Pro Leu Leu Leu Ile Val Glu Tyr Ala Lys Tyr Gly
            20                  25                  30

Ser Leu Arg
        35
```